United States Patent
Myhren et al.

(10) Patent No.: US 11,744,864 B2
(45) Date of Patent: Sep. 5, 2023

(54) METHOD OF TREATING EYE DISEASES WITH KRILL OIL

(71) Applicants: Aker BioMarine Antarctic AS, Stamsund (NO); The Board of Trustees of the University of Illinois, Urbana, IL (US)

(72) Inventors: Finn Myhren, Stamsund (NO); Petter-Arnt Hals, Stamsund (NO); Nils Hoem, Stamsund (NO); Andreas Berg Storsve, Stamsund (NO); Papasani V. Subbaiah, Darien, IL (US); Poorna Yalagala, Urbana, IL (US); Sugasini Dhavamani, Urbana, IL (US); Leon Tai, Urbana, IL (US)

(73) Assignee: THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 12 days.

(21) Appl. No.: 17/218,760

(22) Filed: Mar. 31, 2021

(65) Prior Publication Data

US 2021/0308193 A1  Oct. 7, 2021

Related U.S. Application Data

(60) Provisional application No. 63/113,908, filed on Nov. 15, 2020, provisional application No. 63/002,425, filed on Mar. 31, 2020.

(51) Int. Cl.

| | |
|---|---|
| A61P 27/02 | (2006.01) |
| A61K 9/00 | (2006.01) |
| A61K 31/047 | (2006.01) |
| A61K 31/122 | (2006.01) |
| A61K 31/685 | (2006.01) |
| C12P 9/00 | (2006.01) |
| A61K 35/612 | (2015.01) |

(52) U.S. Cl.
CPC .......... *A61K 35/612* (2013.01); *A61K 9/0019* (2013.01); *A61K 9/0053* (2013.01); *A61K 31/047* (2013.01); *A61K 31/122* (2013.01); *A61K 31/685* (2013.01); *A61P 27/02* (2018.01); *C12P 9/00* (2013.01)

(58) Field of Classification Search
CPC .. A61K 35/612; A61K 9/0019; A61K 9/0053; A61K 31/047; A61K 31/122; A61K 31/685; A61P 27/02; C12P 9/00
See application file for complete search history.

(56) References Cited

U.S. PATENT DOCUMENTS

| | | | | |
|---|---|---|---|---|
| 10,052,352 | B2* | 8/2018 | Driscoll | A61K 9/107 |
| 10,555,957 | B2* | 2/2020 | Subbaiah | A61P 25/28 |
| 2011/0224450 | A1* | 9/2011 | Sclabos Katevas | A61K 8/553 |
| | | | | 554/8 |
| 2018/0325924 | A1* | 11/2018 | Subbaiah | A61K 9/1075 |
| 2021/0251934 | A1* | 8/2021 | Fliri | A61K 31/155 |

FOREIGN PATENT DOCUMENTS

| | | |
|---|---|---|
| CN | 110564787 | * 12/2019 |
| WO | WO2008068413 | 6/2008 |
| WO | WO 2011/011607 | * 1/2011 |
| WO | WO 2015048554 | 4/2015 |
| WO | WO2018162617 | 9/2018 |
| WO | WO 2019123015 | 6/2019 |
| WO | WO 2020254675 | 12/2020 |

OTHER PUBLICATIONS

Yalagala, P. et al. Lipase Treatment of Dietary Krill Oil, but Not Fish Oil, Enables Enrichment of Brain EPA and DHA. Molecular Nutrition & Food Research 64(12)1-13, Jun. 2020. (Year: 2020).*
Berger, A. Polar Lipids—Phospholipids and Glycolipids—An Enhanced Omega-3 Structure. Qualia Health Oct. 2014. (Year: 2014).*
Colletti A. et al. Advances in Technologies for Highly Active Omega-3 Fatty Acids from Krill Oil. Marine Drugs 19: 1-30, May 2021. (Year: 2021).*
Abcouwer S.F., Gardner T.W. Diabetic retinopathy: Loss of neuroretinal adaptation to the diabetic metabolic environment. *Ann. N. Y. Acad. Sci.* 2014;1311:174-190. doi: 10.1111/nyas.12412.
Anderson R.E., Maude M.B., Bok D. Low docosahexaenoic acid levels in rod outer segment membranes of mice with rds/peripherin and P216L peripherin mutations. *Investig. Ophthalmol. Vis. Sci.* 2001;42:1715-1720.
Arsenault, D., Julien, C., Tremblay, C., and Calon, F. (2011) DHA Improves Cognition and Prevents Dysfunction of Entorhinal Cortex Neurons in 3xTg-AD Mice. PLoS One 6, e17397.

(Continued)

*Primary Examiner* — Aaron J Kosar

(74) *Attorney, Agent, or Firm* — Casimir Jones SC; John Mitchell Jones

(57) ABSTRACT

The present invention provides compositions comprising phosphatidylcholine derived compounds carrying an omega-3 fatty acid for use in prophylaxis or therapy, particularly when administered systemically. This invention further relates to a modified krill oil composition enriched in LPC-DHA and LPC-EPA, methods of making and methods of using to treat neurological and ocular disorders.

19 Claims, 23 Drawing Sheets

(56) References Cited

OTHER PUBLICATIONS

Balakrishnan, J. et al., Structured form of DHA prevents neurodegenerative disorders: A better insight into the pathophysiology and the mechanism of DHA transport to the brain. *Nutrition Research, Elsevier Inc*, vol. 85, Dec. 4, 2020, pp. 119-134.

Barrett, E. C., McBurney, M. I., and Ciappio, E. D. (2014) Omega-3 Fatty Acid Supplementation as a Potential Therapeutic Aid for the Recovery from Mild Traumatic Brain Injury/Concussion. *Advances in Nutrition: An International Review Journal* 5, 268-277.

Bazan, N. G. (2018) Docosanoids and elovanoids from omega-3 fatty acids are pro-homeostatic modulators of inflammatory responses, cell damage and neuroprotection. *Molecular Aspects of Medicine* 64, 18-33.

Bazan, N. G., Molina, M. F., and Gordon, W. C. (2011) Docosahexaenoic acid signalolipidomics in nutrition: significance in aging, neuroinflammation, macular degeneration, Alzheimer's, and other neurodegenerative diseases. *Annu. Rev. Nutr* 31, 321-351.

Bernice H. Wong et al: "Mfsd2a Is a Transporter for the Essential [omega]-3 Fatty Acid Docosahexaenoic Acid (DHA) in Eye and Is Important for Photoreceptor Cell Development", Journal of Biological Chemistry, vol. 291, No. 20, May 13, 2016 (May 13, 2016), pp. 10501-10514.

Bligh, E. G., and Dyer, W. J. (1959) A rapid method of total lipid extraction and purification. *Can. J. Biochem. Physiol* 37, 911-917.

Brindley, D. N. (1993) Hepatic secretion of lysophosphatidylcholine: A novel transport system for polyunsaturated fatty acids and choline. *J. Nutr. Biochem* 4, 442-449.

Chen, A. T., Chibnall, J. T., and Nasrallah, H. A. (2015) A meta-analysis of placebo-controlled trials of omega-3 fatty acid augmentation in schizophrenia: Possible stage-specific effects. *Ann Clin Psychiatry* 27, 289-296.

Chen, C. T., and Bazinet, R. P. (2015) b-oxidation and rapid metabolism, but not uptake regulate brain eicosapentaenoic acid levels. *Prostaglandins Leukotrienes & Essential Fatty Acids* 92, 33-40.

Chew, E. Y., Clemons, T. E., Agrón, E., Launer, L. J., Grodstein, F., Bernstein, P. S., and Group, f. t. A.-R. E. D. S. R. (2015) Effect of Omega-3 Fatty Acids, Lutein/Zeaxanthin, or Other Nutrient Supplementation on Cognitive Function: The AREDS2 Randomized Clinical Trial. *JAMA* 314, 791-801.

Chiu, C. C., Su, K. P., Cheng, T. C., Liu, H. C., Chang, C. J., Dewey, M. E., Stewart, R., and Huang, S. Y. (2008) The effects of omega-3 fatty acids monotherapy in Alzheimer's disease and mild cognitive impairment: A preliminary randomized double-blind placebo-controlled study. *Progress in Neuro-Psychopharmacology and Biological Psychiatry* 32, 1538-1544.

Connor K.M., SanGiovanni J.P., Lofqvist C., Aderman C.M., Chen J., Higuchi A., Hong S., Pravda E.A., Majchrzak S., Carper D., et al. Increased dietary intake of -ë-3-polyunsaturated fatty acids reduces pathological retinal angiogenesis. *Nat. Med.* 2007;13:868. doi: 10.1038/nm1591.

Croset, M., Brossard, N., Polette, A., and Lagarde, M. (2000) Characterization of plasma unsaturated lysophosphatidylcholines in human and rat. Biochemical Journal 345, 61-67.

Cruz-Hernandez, C., Thakkar, S. K., Moulin, J., Oliveira, M., Masserey-Elmelegy, I., Dionisi, F., and Destaillats, F. (2012) Benefits of structured and free monoacylglycerols to deliver eicosapentaenoic (EPA) in a model of lipid malabsorption. *Nutrients* 4, 1781-1793.

Cunnane, S. C., Chouinard-Watkins, R., Castellano, C. A., and Barberger-Gateau, P. (2013) Docosahexaenoic acid homeostasis, brain aging and Alzheimer's disease: Can we reconcile the evidence? *Prostaglandins Leukotrienes & Essential Fatty Acids* 88, 61-70.

Deinema et al. "A Randomized, Double-Masked, Pacebo-Controlled Clinical Trial of Two Forms of Moega-3 Supplements for Treating Dry Eye Disease" Ophthalmology. Jan. 2017;124(1):43-52.

Faiq M.A., Wollstein G., Schuman J.S., Chan K.C. Cholinergic nervous system and glaucoma: From basic science to clinical applications. *Prog. Retin. Eye Res.* 2019;72:100767. doi: 10.1016/j.preteyeres.2019.06.003.

Ferreira, J. J., Rosser, A., Craufurd, D., Squitieri, F., Mallard, N., and Landwehrmeyer, B. (2015) Ethyl-eicosapentaenoic acid treatment in Huntington's disease: A placebo-controlled clinical trial. *Movement Disorders* 30, 1426-1429.

Futterman S., Sturtevant R., Kupfer C. Effect of alloxan diabetes on the fatty acid composition of the retina. *Investig. Ophtalmol. Vis. Sci.* 1969;8:542-544.

Gong J., Rosner B., Rees D.G., Berson E.L., Weigel-DiFranco C.A., Schaefer E.J. Plasma docosahexaenoic acid levels in various genetic forms of retinitis pigmentosa. *Investig. Ophthalmol. Vis. Sci.* 1992;33:2596-2602.

Green P., Glozman S., Weiner L., Yavin E. Enhanced free radical scavenging and decreased lipid peroxidation in the rat fetal brain after treatment with ethyl docosahexaenoate. *Biochim. Biophys. Acta Mol. Cell Biol. Lipids.* 2001;1532:203-212. doi: 10.1016/S1388-1981(01)00132-9.

Hachem M., Geloen A., Van A., Foumaux B., Fenart L., Gosselet F., Da Silva P., Breton G., Lagarde M., Picq M., et al. Efficient docosahexaenoic acid uptake by the brain from a structured phospholipid. *Mol. Neurobiol.* 2015 doi: 10.1007/s12035-015-9228-9.

Harauma, A., Saito, J., Watanabe, Y., and Moriguchi, T. (2014) Potential for daily supplementation of n-3 fatty acids to reverse symptoms of dry eye in mice. *Prostaglandins, Leukotrienes and Essential Fatty Acids* 90, 207-213.

Hashimoto M., Hossain S., Al Mamun A., Matsuzaki K., Arai H. Docosahexaenoic acid: One molecule diverse functions. *Crit. Rev. Biotechnol.* 2017;37:579-597. doi: 10.1080/07388551.2016.1207153.

Hegde K.R., Varma S.D. Electron impact mass spectroscopic studies on mouse retinal fatty acids: Effect of diabetes. *Ophthalmic Res.* 2009;42:9-14. doi: 10.1159/000219679.

Hoffman D.R., Hughbanks-Wheaton D.K., Pearson N.S., Fish G.E., Spencer R., Takacs A., Klein M., Locke K.G., Birch D.G. Four-year placebo-controlled trial of docosahexaenoic acid in X-linked retinitis pigmentosa (DHAX trial): A randomized clinical trial. *JAMA Ophthalmol.* 2014;132:866-873. doi: 10.1001/jamaophthalmol.2014.1634.

Hong, S. H., Belayev, L., Khoutorova, L., Obenaus, A., and Bazan, N. G. (2014) Docosahexaenoic acid confers enduring neuroprotection in experimental stroke. J Neurol. Sci 338, 135-141.

International Search Report & Written Opinion based on PCT/US2021/025110; dated Dec. 23, 2021; 26 pages.

Ivanova, P. T., Milne, S. B., Byrne, M. O., Xiang, Y., and Brown, H. A. (2007) Glycerophospholipid identification and quantitation by electrospray ionization mass spectrometry. *Methods Enzymol* 432, 21-57.

Jasani B., Simmer K., Patole S.K., Rao S.C. Long chain polyunsaturated fatty acid supplementation in infants born at term. *Cochr. Database Syst. Rev.* 2017;3:CD000376. doi: 10.1002/14651858.CD000376.pub4.

Jump, D. B., Depner, C. M., Tripathy, S., and Lytle, K. A. (2015) Potential for Dietary ω-3 Fatty Acids to Prevent Nonalcoholic Fatty Liver Disease and Reduce the Risk of Primary Liver Cancer. *Advances in Nutrition* 6, 694-702.

Jun B., Mukherjee P.K., Asatryan A., Kautzmann M.A., Heap J., Gordon W.C., Bhattacharjee S., Yang R., Petasis N.A., Bazan N.G. Elovanoids are novel cell-specific lipid mediators necessary for neuroprotective signaling for photoreceptor cell integrity. *Sci. Rep.* 2017;7:5279. doi: 10.1038/s41598-017-05433-7.

Kalogerou M., Kolovos P., Prokopiou E., Papagregoriou G., Deltas C., Malas S., Georgiou T. Omega-3 fatty acids protect retinal neurons in the DBA/2J hereditary glaucoma mouse model. *Exp. Eye Res.* 2018;167:128-139. doi: 10.1016/j.exer.2017.12.005.

Kaur G., Molero J.C., Weisinger H.S., Sinclair A.J. Orally administered [14C] DPA and [14C] DHA are metabolised differently to [14C] EPA in rats. *Br. J. Nutr.* 2013;109:441-448. doi: 10.1017/S0007114512001419.

Kaur, G., Begg, D. P., Barr, D., Garg, M., Cameron-Smith, D., and Sinclair, A. J. (2010) Short-term docosapentaenoic acid (22:5 n-3)

(56) References Cited

OTHER PUBLICATIONS supplementation increases tissue docosapentaenoic acid, DHA and EPA concentrations in rats. *Br J Nutr* 103, 32-37.

Kelley, N. S. (2016) Treatment of Nonalcoholic Fatty Liver Disease with Long-Chain n-3 Polyunsaturated Fatty Acids in Humans. *Metab Syndr Relat Disord* 14, 417-430.

Lee, T. K. M., Clandinin, M. T., Hébert, M., and MacDonald, I. M. (2010) Effect of docosahexaenoic acid supplementation on the macular function of patients with Best vitelliform macular dystrophy: randomized clinical trial. *Canadian Journal of Ophthalmology* 45, 514-519.

Lim, S. Y., and Suzuki, H. (2001) Changes in Maze Behavior of Mice Occur after Sufficient Accumulation of Docosahexaenoic Acid in Brain. *Journal of Nutrition* 131, 319-324.

Lima Giacobbo, B., Doorduin, J., Klein, H. C., Dierckx, R. A. J. O., Bromberg, E., and de Vries, E. F. J. (2019) Brain-Derived Neurotrophic Factor in Brain Disorders: Focus on Neuroinflammation. *Molecular Neurobiology* 56, 3295-3312.

Lobanova E.S., Schuhmann K., Finkelstein S., Lewis T.R., Cady M.A., Hao Y., Keuthan C., Ash J.D., Burns M.E., Shevchenko A., et al. Disrupted blood-retina lysophosphatidylcholine transport impairs photoreceptor health but not visual signal transduction. *J. Neurosci.* 2019;39:9689-9701. doi: 10.1523/JNEUROSCI.1142-19.2019.

Martinez M. Severe deficiency of docosahexaenoic acid in peroxisomal disorders: A defect of delta 4 desaturation? *Neurology*. 1990;40:1292-1298. doi: 10.1212/WNL.40.8.1292.

Martins, J. G. (2009) EPA but not DHA appears to be responsible for the efficacy of omega-3 long chain polyunsaturated fatty acid supplementation in depression: evidence from a meta-analysis of randomized controlled trials. *J Am Coll. Nutr* 28, 525-542.

McCusker M.M., Durrani K., Payette M.J., Suchecki J. An eye on nutrition: The role of vitamins, essential fatty acids, and antioxidants in age-related macular degeneration, dry eye syndrome, and cataract. *Clin. Dermatol.* 2016;34:276-285. doi: 10.1016/j.clindermatol. 2015.11.009.

Nair A.B., Jacob S. A simple practice guide for dose conversion between animals and human. *J. Basic Clin. Pharm.* 2016;7:27-31. doi: 10.4103/0976-0105.177703.

Nguyen, L. N., Ma, D., Shui, G., Wong, P., Cazenave-Gassiot, A., Zhang, X., Wenk, M. R., Goh, E. L. K., and Silver, D. L. (2014) Mfsd2a is a transporter for the essential omega-3 fatty acid docosahexaenoic acid. *Nature* 509, 503-506.

Nishizawa, Wang, Sekine, and Saito. (2003) Effect of Dietary DHA on DHA Levels in Retinal Rod Outer Segments in Young versus Mature Rats. *International Journal for Vitamin and Nutrition Research* 73, 259-265.

P. Heinrich Stahl, Camille G. Wermuth (Eds.), Handbook of pharmaceutical salts properties, Selection, and Use; 2002.

Perez, S. E., Berg, B. M., Moore, K. A., He, B., Counts, S. E., Fritz, J. J., Hu, Y. S., Lazarov, O., Lah, J. J., and Mufson, E. J. (2010) DHA diet reduces AD pathology in young APPswe/PS1delta E9 transgenic mice: Possible Gender Effects. *J Neurosci Res* 88, 1026-1040.

Petursdottir, A. L., Farr, S. A., Morley, J. E., Banks, W. A., and Skuladottir, G. V. (2008) Effect of Dietary n-3 Polyunsaturated Fatty Acids on Brain Lipid Fatty Acid Composition, Learning Ability, and Memory of Senescence-Accelerated Mouse. Journals of Gerontology. Series A, Biological Sciences and Medical Sciences 63, 1153-1160.

Phillips, M. A., Childs, C. E., Calder, P. C., and Rogers, P. J. (2015) No. Effect of Omega-3 Fatty Acid Supplementation on Cognition and Mood in Individuals with Cognitive Impairment and Probable Alzheimer's Disease: A Randomised Controlled Trial. International Journal of Molecular Sciences 16, 24600-24613.

Prokopiou E., Kolovos P., Georgiou C., Kalogerou M., Potamiti L., Sokratous K., Kyriacou K., Georgiou T. Omega-3 fatty acids supplementation protects the retina from age-associated degeneration in aged C57BL/6J mice. *BMJ Open Ophthalmol.* 2019;4:e000326. doi: 10.1136/bmjophth-2019-000326.

Prokopiou E., Kolovos P., Kalogerou M., Neokleous A., Nicolaou O., Sokratous K., Kyriacou K., Georgiou T. Omega-3 fatty acids supplementation: Therapeutic potential in a mouse model of stargardt disease. *Investig. Ophthalmol. Vis. Sci.* 2018;59:2757-2767. doi: 10.1167/iovs.17-23523.

Qiu, S., Wei, Y., Zhou, X., Jiang, Z., Zhang, T., Jiang, X., and Zhang, S. (2017) Intravitreal injection of docosahexaenoic acid attenuated photoreceptor cell injury in a NaIO3-induced age-related macular degeneration rat model. *Neuroscience Letters* 657, 53-61.

Querques, G., Forte, R. and Souied, E.H. (2011) Retina and Omega-3. *Journal of Nutrition and Metabolism* 2011.

Quinn, J. F., Raman, R., and Thomas, R. G. (2010) Docosahexaenoic acid supplementation and cognitive decline in alzheimer disease: A randomized trial. *JAMA* 304, 1903-1911.

Ramprasath, V. R., Eyal, I., Zchut, S., and Jones, P. J. H. (2013) Enhanced increase of omega-3 index in healthy individuals with response to 4-week n-3 fatty acid supplementation from krill oil versus fish oil. *Lipids in Health and Disease* 12, 178.

Rodrigues, P. O., Martins, S. V., Lopes, P. A., Miguueis, S., Alfaia, C. M., Pinto, R. M. A., Rolo, E. A., Bispo, P., Batista, I., Bandarra, N. M., and Prates, J. A. M. (2014) Influence of feeding graded levels of canned sardines on the inflammatory markers and tissue fatty acid composition of Wistar rats. *British Journal of Nutrition* 112, 309-319.

Ross, B. M. (2008) The Emerging Role of Eicosapentaenoic Acid as an Important Psychoactive Natural Product: Some Answers but a Lot more Questions. *Lipid Insights* 2, 89-97.

Rossino M.G., Casini G. Nutraceuticals for the treatment of diabetic retinopathy. Nutrients. 2019;11:771. doi: 10.3390/nu11040771.

Salem, N., and Kuratko, C. N. (2014) A reexamination of krill oil bioavailability studies. *Lipids in Health and Disease* 13, 137.

SanGiovanni J.P., Chew E.Y. The role of omega-3 long-chain polyunsaturated fatty acids in health and disease of the retina. *Progress Retin. Eye Res.* 2005;24:87-138. doi: 10.1016/j.preteyeres. 2004.06.002.

Sapieha P., Chen J., Stahl A., Seaward M.R., Favazza T.L., Juan A.M., Hatton C.J., Joyal J.S., Krah N.M., Dennison R.J., et al. Omega-3 polyunsaturated fatty acids preserve retinal function in type 2 diabetic mice. *Nutr. Diabet.* 2012;2:e36. doi: 10.1038/nutd. 2012.10.

Schaefer E.J., Robins S.J., Patton G.M., Sandberg M.A., Weigel-DiFranco C.A., Rosner B., Berson E.L. Red blood cell membrane phosphatidylethanolamine fatty acid content in various forms of retinitis pigmentosa. *J. Lipid Res.* 1995;36:1427-1433.

Schnebelen C., Viau S., Grégoire S., Joffre C., Creuzot-Garcher C.P., Bron A.M., Bretillon L., Acar N. Nutrition for the eye: Different susceptibility of the retina and the lacrimal gland to dietary omega-6 and omega-3 polyunsaturated fatty acid incorporation. Ophthalmic Res. 2009;41:216-224. doi: 10.1159/000217726.

Schuchardt, J. P., Schneider, I., Meyer, H., Neubronner, J., von Schacky, C., and Hahn, A. (2011) Incorporation of EPA and DHA into plasma phospholipids in response to different omega-3 fatty acid formulations—a comparative bioavailability study of fish oil vs. krill oil. *Lipids Health Dis* 10, 145-145.

Sekas, G., Patton, G. M., Lincoln, E. C., and Robins, S. J. (1985) Origin of plasma lysophosphatidylcholine: evidence for direct hepatic secretion in the rat. *J Lab Clin Med* 105, 190-194.

Sethom, M. M., Fares, S., Bouaziz, N., Melki, W., Jemaa, R., Feki, M., Hechmi, Z., and Kaabachi, N. (2010) Polyunsaturated fatty acids deficits are associated with psychotic state and negative symptoms in patients with schizophrenia. *Prostaglandins Leukotrienes & Essential Fatty Acids* 83, 131-136.

Sona, C., Kumar, A., Dogra, S., Kumar, B. A., Umrao, D., and Yadav, P. N. (2018) Docosahexaenoic acid modulates brain-derived neurotrophic factor via GPR40 in the brain and alleviates diabesity-associated learning and memory deficits in mice. *Neurobiol Dis* 118, 94-107.

Song, C., Shieh, C. H., Wu, Y. S., Kalueff, A., Gaikwad, S., and Su, K. P. (2016) The role of omega-3 polyunsaturated fatty acids eicosapentaenoic and docosahexaenoic acids in the treatment of major depression and Alzheimer's disease: Acting separately or synergistically? *Prog Lipid Res* 62, 41-54.

(56) References Cited

OTHER PUBLICATIONS

Souied, E. H., Aslam, T., Garcia-Layana, A., Holz, F. G., Leys, A., Silva, R., and Delcourt, C. (2016) Omega-3 Fatty Acids and Age-Related Macular Degeneration. *Ophthalmic Research* 55, 62-69.
Stinson A.M., Wiegand R.D., Anderson R.E. Recycling of docosahexaenoic acid in rat retinas during n-3 fatty acid deficiency. *J. Lipid Res*. 1991;32:2009-2017.
Subbaiah, P. V., Dammanahalli, K. J., Yang, P., Bi, J., and O'Donnell, J. M. (2016) Enhanced incorporation of dietary DHA into lymph phospholipids by altering its molecular carrier. *Biochim Biophys Acta* 1861, 723-729.
Sugasini D et al. Efficient enrichment of retinal DHA with dietary lysophosphatidylcholine-DHA: potential application for retinopathies; *Nutrients* vol. 12, No. 10, Oct. 1, 2020, p. 3114.
Sugasini, D., and Subbaiah, P. V. (2017) Rate of acyl migration in lysophosphatidylcholine (LPC) is dependent upon the nature of the acyl group. Greater stability of sn-2 docosahexaenoyl LPC compared to the more saturated LPC species. *PLoS One* 12, e0187826.
Sugasini, D., Thomas, R., Yalagala, P. C. R., Tai, L. M., and Subbaiah, P. V. (2017) Dietary docosahexaenoic acid (DHA) as lysophosphatidylcholine, but not as free acid, enriches brain DHA and improves memory in adult mice. *Scientific Reports* 7, 11263.
Sugasini, D., Yalagala, P. C. R., Goggin, A., Tai, L. M., and Subbaiah, P. V. (2019) Enrichment of brain docosahexaenoic acid (DHA) is highly dependent upon the molecular carrier of dietary DHA: Lysophosphatidylcholine is more efficient than either phosphatidylcholine or triacylglycerol. The Journal of Nutritional Biochemistry, 108231.
Suh M., Clandinin M.T. 20:5n-3 but not 22:6n-3 is a preferred substrate for synthesis of n-3 very-long-chain fatty acids (C24-C36) in retina. *Curr. Eye Res*. 2005;30:959-968. doi: 10.1080/02713680500246957.
Suh M., Sauvé Y., Merrells K.J., Kang J.X., Ma D.W.L. Supranormal electroretinogram in F at-1 mice with retinas enriched in docosahexaenoic acid and n-3 very long chain fatty acids (C24-C36) Investig. Ophthalmol. Vis. Sci. 2009;50:4394-4401. doi: 10.1167/iovs.08-2565.
Sun, G. Y., Simonyi, A., Fritsche, K. L., Chuang, D. Y., Hannink, M., Gu, Z., Greenlief, C. M., Yao, J. K., Lee, J. C., and Beversdorf, D. Q. (2018) Docosahexaenoic acid (DHA): An essential nutrient and a nutraceutical for brain health and diseases. *Prostaglandins Leukotrienes & Essential Fatty Acids* 136, 3-13.
Tachikawa M., Akanuma S.I., Imai T., Okayasu S., Tomohiro T., Hatanaka Y., Hosoya K.I. Multiple cellular transport and binding processes of unesterified docosahexaenoic acid in outer blood-retinal barrier retinal pigment epithelial cells. *Biol. Pharm. Bull*. 2018;41:1384-1392. doi: 10.1248/bpb.b18-00185.
Tanito M., Brush R.S., Elliott M.H., Wicker L.D., Henry K.R., Anderson R.E. High levels of retinal membrane docosahexaenoic acid increase susceptibility to stress-induced degeneration. *J. Lipid Res*. 2009;50:807-819. doi: 10.1194/jlr.M800170-JLR200.

Thies F., Delachambre M.C., Bentejac M., Lagarde M., Lecerf J. Lyso-sn 1 Phosphatidylcholine Bound to Albumin: A Preferential Form for Rat Brain Uptake of Unsaturated Fatty Acids Compared to the Unesterified Form?; Proceedings of the 32nd International Conference on Biochemistry of Lipids; Granada, Spain. Sep. 18-21, 1991; p. 3.
Tikhonenko, M., Lydic, T. A., Opreanu, M., Li Calzi, S., Bozack, S., McSorley, K. M., Sochacki, A. L., Faber, M. S., Hazra, S., Duclos, S., Guberski, D., Reid, G. E., Grant, M. B., and Busik, J. V. (2013) N-3 Polyunsaturated Fatty Acids Prevent Diabetic Retinopathy by Inhibition of Retinal Vascular Damage and Enhanced Endothelial Progenitor Cell Reparative Function. *PLOS One* 8, e55177.
Tou, J., Altman, S., Gigliotti, J., Benedito, V., and Cordonier, E. (2011) Different sources of omega-3 polyunsaturated fatty acids affects apparent digestibility, tissue deposition, and tissue oxidative stability in growing female rats. *Lipids in Health and Disease* 10, 179.
Uauy R., Hoffman D.R., Peirano P., Birch D.G., Birch E.E. Essential fatty acids in visual and brain development. *Lipids*. 2001;36:885-895. doi: 10.1007/s11745-001-0798-1.
Valenzuela A. et al. Supplementing female rates with DHA-lysophosphatidylcholine increases docosahexaenoic acid and acetylcholine contents in the brain and improves the memory and learning capabilities of the pups. *Grases y Aceites*, val. 61, No. 1, Mar. 30, 2010.
Wong B.H., Chan J.P., Cazenave-Gassiot A., Poh R.W., Foo J.C., Galam D.L., Ghosh S., Nguyen L.N., Barathi V.A., Yeo S.W., et al. Mfsd2a is a transporter for the essential omega-3 fatty acid docosahexaenoic acid (DHA) in eye and is important for photoreceptor cell development. *J. Biol. Chem*. 2016;291:10501-10514. doi: 10.1074/jbc.M116.721340.
Yalagala P.C.R., Sugasini D., Zaldua S.B., Tai L.M., Subbaiah P.V. Lipase treatment of dietary krill oil, but not fish oil, enables enrichment of brain eicosapentaenoic acid (EPA) and docosahexaenoic acid (DHA) *Mol. Nutr. Food Res*. 2020;64 doi: 10.1002/mnfr.202000059.
Yalagala, P. C. R., Sugasini, D., Dasarathi, S., Pahan, K., and Subbaiah, P. V. (2019) Dietary lysophosphatidylcholine-EPA enriches both EPA and DHA in the brain: potential treatment for depression. *Journal of Lipid Research* 60, 566-578.
Yang S.P., Morita I., Murota S.I. Eicosapentaenoic acid attenuates vascular endothelial growth factor-induced proliferation via inhibiting Flk-1 receptor expression in bovine carotid artery endothelial cells. *J. Cell Physiol*. 1998;176:342-349. doi: 10.1002/(SICI)1097-4652(199808)176:2<342::AID-JCP12>3.0.CO;2-5.
Yee P., Weymouth A.E., Fletcher E.L., Vingrys A.J. A Role for Omega-3 Polyunsaturated Fatty Acid Supplements in Diabetic Neuropathy. *Investig. Ophthalmol. Vis. Sci*. 2010;51:1755-1764. doi: 10.1167/iovs.09-3792.
Yu M., Benham A., Logan S., Brush R.S., Mandal M.N., Anderson R.E., Agbaga M.P. ELOVL4 protein preferentially elongates 20:5n3 to very long chain PUFAs over 20:4n6 and 22:6n3. *J. Lipid Res*. 2012;53:494-504. doi: 10.1194/jlr.M021386.

\* cited by examiner

METHOD OF TREATING EYE DISEASES WITH KRILL OIL

CROSS REFERENCE TO RELATED APPLICATIONS

This application claims the benefit of U.S. Prov. Appl. 63/002,425, filed Mar. 31, 2020 and U.S. Prov. Appl. 63/113,908 filed Nov. 15, 2020, both of which are incorporated by reference herein in their entirety.

FIELD OF THE INVENTION

The present invention provides compositions comprising phosphatidylcholine derived compounds carrying an omega-3 fatty acid for use in prophylaxis or therapy, particularly when administered systemically. This invention further relates to a modified krill oil composition enriched in LPC-DHA and LPC-EPA, methods of making and methods of using to treat neurological and ocular disorders.

BACKGROUND OF THE INVENTION

The brain contains very high concentration of the omega 3 fatty acid DHA, which plays a significant role in the development and function of the brain. Deficiency of brain DHA has been associated with several neurological diseases, including Alzheimer's, Parkinson's, schizophrenia, and depression (1-3). DHA has also been shown to be protective against complications of stroke (4) and traumatic brain injury (5). Although the beneficial effects of dietary DHA has been reported in various animal models of neurodegenerative diseases (6-9), clinical trials employing the currently available supplements (fish oil, algal oil, krill oil, ethyl esters) have provided disappointing results in patients with Alzheimer's disease (10-12), Huntington's disease (13), and schizophrenia (14). It has been proposed that the failure of these trials is due to the inability of these supplements to enrich brain DHA, because DHA from them is absorbed mainly in the form of triacylglycerol (TAG), whereas the transporter at the BBB requires a lysophosphatidylcholine form of DHA (LPC-DHA) (15). Indeed it has been recently demonstrated that feeding DHA in the form of LPC increased brain DHA by up to 100% in normal adult mice, whereas free DHA at the same dose had no effect (16). It was also shown that LPC-DHA is superior to either PC-DHA or TAG-DHA in the enrichment of brain DHA in rats (17). In contrast to DHA, the brain contains very little EPA, and supplements rich in EPA do not increase brain EPA content significantly (18-21), although dietary EPA has been shown to be more beneficial than DHA for the prevention and treatment of depression (22-24). It has been proposed that the lack of EPA enrichment of the brain is due to its rapid oxidation in the brain (25). However, it has been demonstrated that brain EPA can indeed be increased by up to 100-fold by providing dietary EPA in the form of LPC (26), indicating that the low levels of EPA is mainly due to the low levels of LPC-EPA in plasma.

Additionally, the retina has the highest concentration of DHA in the body. It also has a large percentage of very long chain fatty acids derived from EPA and DHA (32-36 n-3) and contains phospholipids containing omega 3 fatty acids at both sn-1 and sn-2 positions. These fatty acids and unique phospholipids perform vital functions in maintaining the photoreceptor cell integrity (41).

DHA has anti-inflammatory, anti-angiogenic, and pro-homeostatic roles in the retina, and deficiency of DHA is associated with macular degeneration, and other retinopathies (42). Several epidemiologic studies showed a beneficial effect of omega 3 fatty acid intake in the prevention of various retinopathies (42) (43). Furthermore, Tikhonenkho et al (44) reported that diabetic retinopathy could be prevented in experimental animals by providing DHA in the diet. DHA has also been shown to be protective against dry eye disease (45) and age-related macular degeneration (46) in animal models. Despite the positive results from the epidemiologic and experimental studies, however, intervention studies in patients using dietary supplements showed no apparent benefit (47) (48), most probably because of inefficient uptake of conventional DHA supplements by retina. It is of interest to note that Nishizawa et al (49) reported that while the retinal DHA can be increased in growing rats, the DHA content of adult retinal membranes cannot be increased even with high DHA dose (8.5% calories). This could be the explanation for the failure of the previous clinical trials.

Ocular infections and inflammations include a wide range of pathologic conditions, that can be primary or secondary to a primary illness.

One example is dry eye disease (DED), a highly prevalent, multifactorial disease of the tear film and ocular surface that results in eye pain and impaired vision. The mainstay of DED therapy, involving instillation of lubricant eye drops to provide temporary symptomatic relief, is supportive rather than therapeutic. Inflammation is a core mechanism in the pathogenesis of DED, where tear hyperosmolarity and instability, contribute to the inflammatory response. This underwrites the chronic irritation and pain experienced by DED sufferers. Topical anti-inflammatory agents, such as corticosteroids, are currently used to manage DED, but potential long-term adverse effects limit their use.

The omega-3 (n-3) long-chain polyunsaturated fatty acids (LC-PUFA), eicosapentaenoic (EPA, 20:5n-3) and docosahexaenoic (DHA, 22:6n-3) acids, are well accepted as being essential components of a healthy, balanced diet, having beneficial effects on development and in mitigating a range of pathological conditions, including ocular pathologies such as for example retinal diseases and age-related macular degeneration (AMD).

As reviewed by Querques et al, the retina has the highest concentration of DHA in the body, and several studies suggest that omega-3 polyunsaturated fatty acids could have a protective role in reducing the onset and progression of retinal diseases (Querques et al., J Nutr Metab. 2011; 2011: 748361). The high concentration of DHA is suggested to optimize fluidity of photoreceptor membranes, retinal integrity, and visual function. Furthermore, many studies demonstrated that DHA has a protective, for example antiapoptotic, role in the retina. In contrast to DHA, the brain, nervous tissue and retina contains very little eicosapentaenoic acid (EPA), but there are indications that EPA may have a protective role in preventing neurodegeneration (Yalagala et al J Lipid Res. 2019 March; 60(3):566-578. doi: 10.1194/jlr.M090464. Epub 2018 Dec. 10). From a nutritional point of view, it is known that western populations, particularly aged individuals, have a higher than optimal omega-6/omega-3 ratio and should enrich their diet with more omega-3 polyunsaturated fatty acids to improve inflammation-related pathogenesis.

Dry eye is a common eye disease. It affects 5-34% of people to some degree depending on the population looked at. Among older people it affects up to 70%. Although dietary omega-3 supplements have been suggested for the prevention and treatment of several ocular disease, one clinical trial with omega-3 from fish oils and phospholipid rich krill oil for treating DED did not demonstrate a significantly change in the frequency of lubricating eye drop utilization (Deinema et al. Ophthalmology. 2017 January; 124(1):43-52).

In spite of the efforts in the field, the problem of dry eye remains very extended and unsolved being an unmet medical need. Thus, it would be desirable to provide new improved treatments for dry eye.

It would be preferred if such treatments could provide both symptomatic and therapeutic relief.

In particular, it would be preferable if such improved treatments could prevent ocular pathologies, such as glaucoma, AMD, diabetic retinopathy and neuropathies, by protecting against degeneration in ocular tissue and retina.

SUMMARY OF THE INVENTION

Deficiency of brain DHA is associated with several neurodegenerative diseases, but the current supplements do not enrich brain DHA because of the requirement of the transporter at blood brain barrier for lysophosphatidylcholine (LPC-DHA). Krill oil phospholipids contain DHA and EPA at sn-2 position, but do not generate LPC-DHA and LPC-EPA since pancreatic phospholipase $A_2$ releases them as free acids.

However, the inventors have discovered that if dietary krill oil is pre-treated with sn-1 specific lipase, LPC-DHA and LPC-EPA are generated and should therefore enrich brain DHA and EPA. We tested this hypothesis by feeding untreated (UTKO) and lipase-treated (LTKO) krill oil to normal mice and determining the fatty acid composition of brain and other tissues. Whereas UTKO increased brain DHA and EPA modestly, LTKO was 5- and 70-fold more effective in enriching brain DHA and EPA respectively, and increased brain BDNF. In contrast, fish oil (which contains no phospholipid) had no effect on brain DHA or EPA whether lipase-treated or not. LTKO was also more efficient in enriching liver DHA and EPA, but less efficient than fish oil or UTKO in enriching adipose tissue and heart. These results provide a novel strategy to target dietary DHA and EPA to the brain for prevention and treatment of neurological diseases such as Alzheimer's.

Accordingly, in a first aspect the present invention relates to a method for treating, preventing and/or relieving one or more symptoms and/or signs of a disease or condition of the eye comprising administering to a subject in need thereof an effective amount of a formulation comprising a lysophosphatidylcholine (LPC) composition comprising a LPC-compound selected from the group consisting of any one of formula 1 to 8, and any combination thereof so that the symptoms of the disease or condition are improved, controlled, reduced or alleviated:

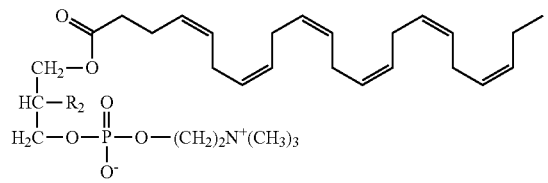

Formula 1

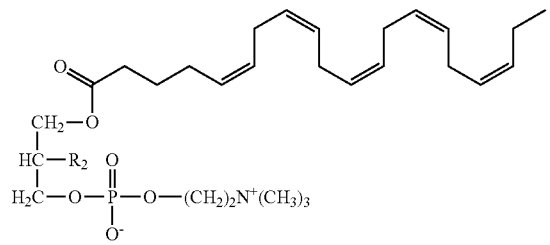

Formula 2

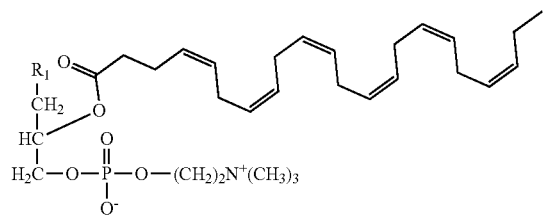

Formula 3

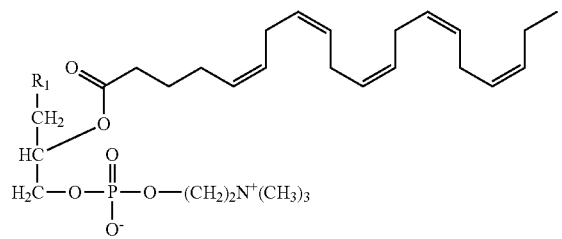

Formula 4

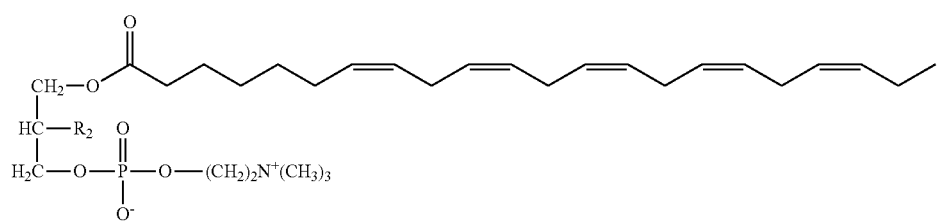

Formula 5

Formula 6

$$CH_2-O-C(O)-CH_2CH_2CH_2CH_2CH=CH-CH_2-CH=CH-CH_2-CH=CH-CH_2-CH=CH-CH_2CH_2CH_3$$
$$HC-R_2$$
$$H_2C-O-P(O)(O^-)-O-(CH_2)_2N^+(CH_3)_3$$

Formula 7

$$R_1-CH_2-O-C(O)-(CH_2)_{n}-CH=CH-...$$
$$HC-O$$
$$H_2C-O-P(O)(O^-)-O-(CH_2)_2N^+(CH_3)_3$$

Formula 8

$$R_1-CH_2-O-C(O)-(CH_2)_{n}-CH=CH-...$$
$$HC-O$$
$$H_2C-O-P(O)(O^-)-O-(CH_2)_2N^+(CH_3)_3$$

wherein $R_1$ is OH or $-OC(O)(CH_2)_nCH_3$
$R_2$ is OH or $-OC(O)(CH_2)_nCH_3$ and
n is 0, 1 or 2.

In one embodiment of the first aspect the $R_1$ is OH and $R_2$ is OH.

In one embodiment of the first aspect the, with the proviso that: if the LPC composition comprises i) a compound according to formula 1, wherein $R_2$ is OH; and/or ii) a compound according to formula 3, wherein $R_1$ is OH; then the LPC composition further comprises at least one of the other LPC-compounds referred to in the first aspect.

In one embodiment of the first aspect, the one or more LPC-compound is:
  a compound according to formula 1; and/or a compound according to formula 3; and
  a compound according to formula 2; and/or a compound according to formula 4.

In one embodiment of the first aspect the,
$R_1$ and $R_2$ are OH; and
molar ratio of lysoPC-DHA:lysoPC-EPA is in the range 1:1 to 3:1; or molar ratio of lysoPC-EPA:lysoPC-DHA is in the range 1:1 to 5:1; with the proviso that i) the number of moles of lysoPC-EPA is the number of moles 1-lysoPC-EPA+the number of moles 2-lysoPC-EPA; and ii) the number of moles of lysoPC-DHA is the number of moles 1-lysoPC-DHA+the number of moles 2-lysoPC-DHA.

In one embodiment of the first aspect, the disease or condition is dry eye, such as dry eye disease selected from the group consisting of inflammation of the eye, corneal nerve abnormalities and abrasions on the surface of the eye.

In one embodiment of the first aspect, the disease or condition is a neurodegenerative disease of the eye.

In one embodiment of the first aspect, the neurodegenerative disease of the eye is selected from the group consisting of age-related macular degeneration, diabetic retinopathy, Non-Proliferative Retinopathy, Proliferative Retinopathy, Diabetic macular edema, Retinitis pigmentosa, Central vein occlusion and glaucoma.

In one embodiment of the first aspect, the administering is by a mode selected from the group consisting of oral administration and intravascular or intravenous administration.

In one embodiment of the first aspect, the mode of administration is oral administration.

In one embodiment of the first aspect, the mode of administration is intravascular or intravenous administration.

In one embodiment of the first aspect, the LPC composition in the formulation comprises a LPC-compound selected from the group consisting of any one of formula 1 to 8, and wherein the LPC composition comprises an amount of total LPC corresponding to from 10-100% by weight of the LPC-composition.

In one embodiment of the first aspect, the LPC composition further comprises a lipid different from LPC.

In one embodiment of the first aspect, the LPC composition comprises from 5% to 12% by weight of DHA, wherein the DHA is a free fatty acid or ethyl ester or lipid in the LPC-composition.

In one embodiment of the first aspect, the LPC composition comprises from 10% to 24% by weight of EPA, wherein the EPA is a free fatty acid or a ethyl ester or bound to any lipid in the LPC-composition.

In one embodiment of the first aspect, the LPC composition further comprises palmitoleic acid and/or palmitic acid.

In one embodiment of the first aspect, the LPC composition comprises from 2% to 5% by weight of palmitoleic acid, wherein the palmitoleic acid is bound to any lipid in the LPC-composition.

In one embodiment of the first aspect, the LPC composition comprises from 10% to 15% by weight of palmitic acid, wherein the palmitic acid is bound to any lipid in the LPC-composition.

In one embodiment of the first aspect, the lipid different from LPC is selected from the group consisting of triglycerides, ethyl esters, free fatty acids and phospholipids such as phosphatidylethanolamine and phosphatidylcholine.

In one embodiment of the first aspect, the LPC composition comprises an amount of total phospholipids corresponding to at least 35% by weight of the LPC-composition.

In one embodiment of the first aspect, the LPC composition comprises an amount of total LPC corresponding to at least 23% by weight of the LPC-composition.

In one embodiment of the first aspect, the LPC composition comprises an amount of total LPC corresponding to at least 40% by weight of the LPC-composition.

In one embodiment of the first aspect, the LPC composition comprises an amount of total LPC corresponding to at least 60% by weight of the LPC-composition.

In one embodiment of the first aspect, the LPC composition comprises an amount of total LPC corresponding to at least 90% by weight of the LPC-composition.

In one embodiment of the first aspect, the LPC composition comprises an amount of total LPC corresponding to from 90-98% by weight of the LPC-composition.

In one embodiment of the first aspect, the LPC composition comprises an amount of total LPC corresponding to at least 95% by weight of the LPC-composition.

In one embodiment of the first aspect, the formulation comprises from 1% to 35% by weight of the LPC-composition.

In one embodiment of the first aspect, the formulation comprises from 25% by weight of the LPC-composition.

In one embodiment of the first aspect, the formulation comprises from 40% by weight of the LPC-composition.

In one embodiment of the first aspect, the LPC composition comprises a predominant amount of the LPC-compound compared to an amount of phosphatidylcholine.

In one embodiment of the first aspect, the LPC-compound is selected from LPC-EPA, LPC-DHA and any combination thereof.

In one embodiment of the first aspect, the LPC composition comprises a predominant amount of the LPC-compound compared to an amount of phosphatidylcholine.

In one embodiment of the first aspect, the formulation further comprises a component selected from the group consisting of lutein, astaxanthin, zeaxanthin and any combinations thereof.

In one embodiment of the first aspect, the subject is a mammalian subject.

In one embodiment of the first aspect, the subject is a human subject.

In a second aspect the present invention relates to methods of preparing a krill oil composition enriched in LPC-DHA and LPC-EPA comprising treating krill oil with a lipase specific for the sn-1 position of DHA- and EPA-containing phospholipids in said krill oil.

In one embodiment of the second aspect, this invention is a krill oil composition enriched in LPC-DHA and LPC-EPA prepared by treating krill oil with a lipase specific for the sn-1 position of DHA- and EPA-containing phospholipids in said krill oil.

In one embodiment of the second aspect, the lipase comprises lipase from *Mucor meihei*. In another embodiment, the lipase comprises immobilized lipase from *Mucor meihei*. In another embodiment, the krill oil composition comprises lysophosphatidylcholine comprising greater than about 80 percent by weight LPC-DHA and LPC-EPA.

In one embodiment of the second aspect, the krill oil composition comprising lysophosphatidylcholine comprises greater than about 80 percent by weight LPC-DHA and LPC-EPA.

In one embodiment of the second aspect, the krill oil composition comprising lysophosphatidylcholine comprises greater than about 70 percent by weight LPC-DHA and LPC-EPA.

In one embodiment of the second aspect, the krill oil composition comprising lysophosphatidylcholine comprises greater than about 60 percent by weight LPC-DHA and LPC-EPA.

In one embodiment of the second aspect, the krill oil composition comprising lysophosphatidylcholine comprises greater than about 50 percent by weight LPC-DHA and LPC-EPA.

In one embodiment of the second aspect, the krill oil composition comprising lysophosphatidylcholine comprises greater than about 40 percent by weight LPC-DHA and LPC-EPA.

In one embodiment of the second aspect, the krill oil composition comprising lysophosphatidylcholine comprises greater than about 30 percent by weight LPC-DHA and LPC-EPA.

In one embodiment of the second aspect, the krill oil composition comprising lysophosphatidylcholine comprises greater than about 20 percent by weight LPC-DHA and LPC-EPA.

In one embodiment of the second aspect, the krill oil composition comprising lysophosphatidylcholine comprises greater than about 10 percent by weight LPC-DHA and LPC-EPA.

In one embodiment of the second aspect, is the present invention provides a nutraceutical composition comprising a krill oil composition as described above.

In one embodiment of the second aspect, is the present invention provides a pharmaceutical composition comprising a krill oil composition as described above.

In a third aspect the present invention relates to methods of treating or preventing a neurological disease or disorder in a subject comprising administering to the subject an effective amount of a krill oil composition enriched in LPC-DHA and LPC-EPA. In certain embodiments, the neurological disease or disorder is selected from Parkinson's, schizophrenia, traumatic brain injury, stroke and Alzheimer's. In a particular embodiment, the neurological disease or disorder is Alzheimer's.

The inventors have further discovered that feeding a krill oil composition enriched in LPC-DHA and LPC-EPA according to the invention to normal mice resulted in significant increase in retinal EPA and DHA. Similar treatment of fish oil, which contains EPA and DHA only in triglyceride form, had no effect on retinal EPA or DHA.

Accordingly, in another aspect the present invention relates to methods of treating or preventing a retinal disease or disorder in a subject comprising administering to the subject an effective amount of a krill oil composition enriched in LPC-DHA and LPC-EPA. In certain embodiments, the retinal disease or disorder is selected from age-related macular degeneration, diabetic retinopathy and dry eye disease.

In addition, since lipase-treated krill oil is superior to fish oil untreated krill oil in enriching liver omega 3 fatty acids, compositions of this invention may be useful in treating liver diseases such as non-alcoholic fatty liver (NAFLD) and non-alcoholic steatohepatitis (NASH), which are known to be mitigated by DHA enrichment of the liver.

Accordingly, in another aspect the present invention relates to methods of treating or preventing a liver disease mitigated by DHA enrichment of the liver comprising administering to a subject in need of treatment an effective amount of a krill oil composition enriched in LPC-DHA and LPC-EPA. In certain embodiments, the liver disease is selected from non-alcoholic fatty liver (NAFLD) and non-alcoholic steatohepatitis (NASH).

DEFINITIONS

Figure 1:
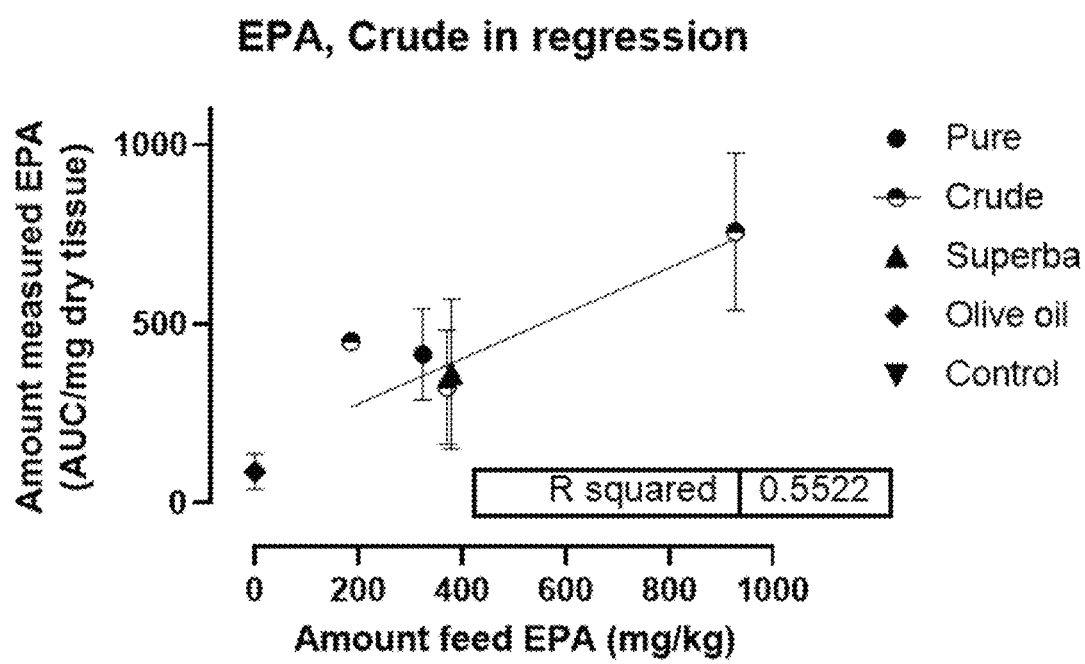
FIG. 1 shows retina EPA contents (AUC/mg dry tissue) at the conclusion of the study.

Throughout the present disclosure relevant terms are to be understood consistently with their typical meanings established in the relevant art, i.e. the art of pharmaceutical chemistry, medicine, biology, biochemistry and physiology.

However, further clarifications and descriptions are provided for certain terms as set forth below.

The following abbreviations shall have the indicated meaning: ARA: Arachidonic acid (20:4, n-6); BBB: Blood brain barrier; BDNF: Brain derived neurotrophic factor; DHA: Docosahexaenoic acid (22:6, n-3); DPA: Docosapentaenoic acid (22:5, n-3); EPA: Eicosapentaenoic acid (20:5, n-3); FA: Fatty acid(s); FO: Fish oil; GC/MS: Gas chromatography/mass spectroscopy; KO: Krill oil; LC/MS/MS: Liquid chromatography/tandem mass spectroscopy; LPC: Lysophosphatidylcholine; PC: Phosphatidylcholine, TAG: Triacylglycerol.

"Krill oil" refers to an extract prepared from a species of Antarctic krill, *Euphausia superba*. Two of the most important components in krill oil are omega-3 fatty acids in the form of DHA and EPA, and phospholipid-derived fatty acids (PLFA), mainly phosphatidylcholine (alternatively referred to as marine lecithin). Krill oil is available commercially.

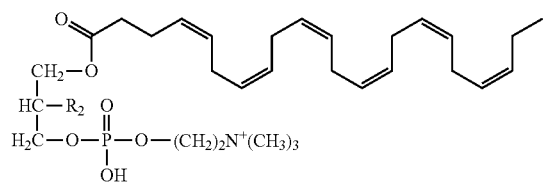

Formula 1

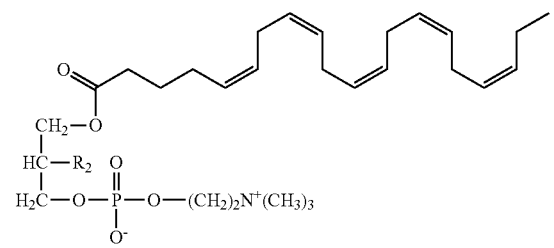

Formula 2

-continued

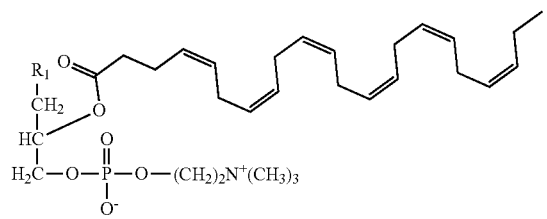

Formula 3

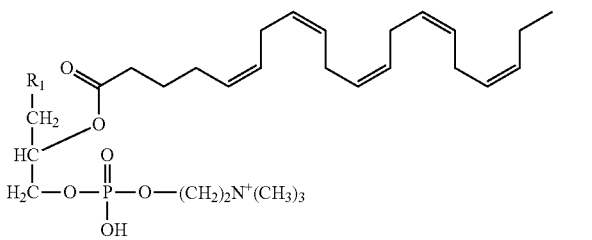

Formula 4

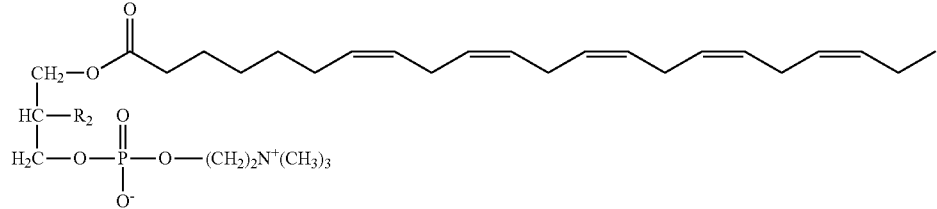

Formula 5

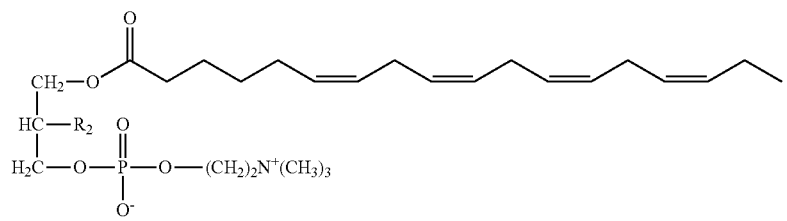

Formula 6

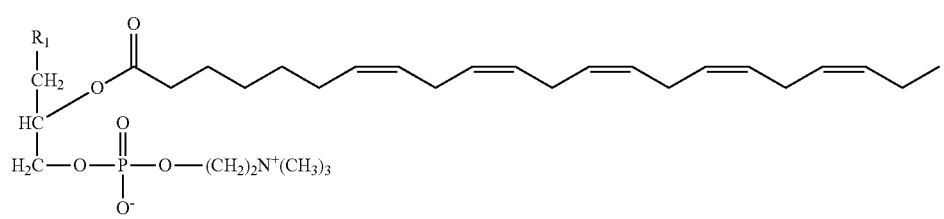

Formula 7

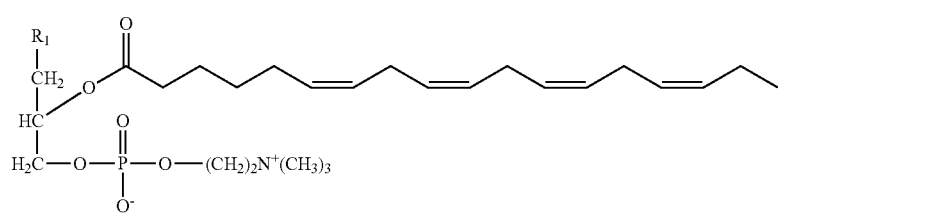

Formula 8

The terms "2-lysoPC-DHA" and "2-LPC-DHA" are used interchangeably herein and refer to a compound according to formula 1, wherein $R_2$ is OH.

The terms "2-lysoPC-EPA" and "2-LPC-EPA" are used interchangeably herein and refer to a compound according to formula 2, wherein $R_2$ is OH.

The terms "2-lysoPC-DPA" and "2-LPC-DPA" are used interchangeably herein and refer to a compound according to formula 5, wherein $R_2$ is OH.

The terms "2-lysoPC-SDA" and "2-LPC-SDA" are used interchangeably herein and refer to a compound according to formula 6, wherein $R_2$ is OH.

The terms "1-lysoPC-DHA" and "1-LPC-DHA" are used interchangeably herein and refer to a compound according to formula 3, wherein $R_1$ is OH.

The terms "1-lysoPC-EPA" and "1-LPC-EPA" are used interchangeably herein and refer to a compound according to formula 4, wherein $R_1$ is OH.

The terms "1-lysoPC-DPA" and "1-LPC-DPA" are used interchangeably herein and refer to a compound according to formula 7, wherein $R_1$ is OH.

The terms "1-lysoPC-SDA" and "1-LPC-SDA" are used interchangeably herein and refer to a compound according to formula 8, wherein $R_1$ is OH.

The terms "lysoPC-DHA" and "LPC-DHA" are used interchangeably herein and includes both 1-lysoPC-DHA and 2-lysoPC-DHA.

The terms "lysoPC-EPA" and "LPC-EPA" are used interchangeably herein and includes both 1-lysoPC-EPA and 2-lysoPC-EPA.

The terms "lysoPC-DPA" and "LPC-DPA" are used interchangeably herein and includes both 1-lysoPC-DPA and 2-lysoPC-DPA.

The terms "lysoPC-SDA" and "LPC-SDA" are used interchangeably herein and includes both 1-lysoPC-SDA and 2-lysoPC-SDA.

The term "EPA" refers to eicosapentaenoic acid.

The term "DHA" refers to docosahexaenoic acid.

The term "DPA" refers to n3-docosapentaenoic acid. The term "n3" specifying that the compound is an omega-3 fatty acid.

The term "SDA" refers to stearidonic acid.

EPA, DHA, DPA, SDA, as used herein in connection with the compositions of the invention, refers to the fatty acid chain that can be bound to a lipid backbone, such as to phospholipids, lysophospholipids, triacylglycerides, diacylglyceride, monoacylglyceride or any other lipid backbone, or it can exist in the compositions as a free fatty acid or ethyl ester.

The term "total LPC" is used herein to describe the total content of lysophosphatidylcholine in a composition.

The term "total phospholipids" is used herein to describe the total content of phospholipids, including lysophospholipids, in a composition.

The term "intravenous administration" as used herein refers to a mode of administration where a liquid substance is delivered directly into a vein. The intravenous route of administration can be used for injections (with a syringe at higher pressures) or infusions (typically using only the pressure supplied by gravity).

The term "pharmaceutically acceptable excipients" refer to substances different from the components of the LPC-compositions referred to in the claims and which are commonly used with oily pharmaceuticals. Such excipients include, but are not limited to triolein, soybean oil, safflower oil, sesame oil, castor oil, coconut oil, triglycerides, tributyrin, tricaproin, tricaprylin, vitamin E, antioxidants, α-tocopherol, ascorbic acid, deferoxamine mesylate, thioglycolic acid, emulsifiers, lecithin, polysorbate 80, methylcellulose, gelatin, serum albumin, sorbitan lauraute, sorbitan oleate, sorbitan trioleate, polyethylene glycol (PEG), PEG 400, polyethylene glycol-modified phosphatidylethanolamine (PEG-PE), poloxamers, glycerin, sorbitol, Xylitol, pH adjustment agents; sodium hydroxide, antimicrobial agents EDTA, sodium benzoate, benzyl alcohol and proteins such as albumin. The pharmaceutically acceptable excipients must be acceptable in the sense of being compatible with the other ingredients of the composition and not deleterious to the recipient thereof.

Used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of pharmaceutical salts properties, Selection, and Use; 2002.

The term "prophylaxis" means measures taken to prevent, rather than treat, diseases or conditions.

The term "effective amount" refers to the amount of a disclosed compound or composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

The term "therapeutically effective amount" is an art-recognized term. In certain embodiments, the term refers to an amount of the composition disclosed herein that produces some desired effect at a reasonable benefit/risk ratio applicable to the medical treatment. In certain embodiments, the term refers to that amount necessary or sufficient to eliminate, reduce or alleviate medical symptoms for a period of time. The effective amount may vary depending on such factors as the disease or condition being treated, the particular composition being administered, the size of the subject, or the severity of the disease or condition. One of ordinary skill in the art may empirically determine the effective amount of a particular composition without necessitating undue experimentation.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance may be found in the literature for appropriate dosages for given classes of pharmaceutical products.

The term "treating" is art-recognized and includes preventing a disease, disorder or condition from occurring in a subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating dry eye disease selected from inflammation of the eye, corneal nerve abnormalities and abrasions on the surface of the eye or neurodegenerative disease of the eye selected from age-related macular degeneration, diabetic retinopathy, Non-Proliferative Retinopathy, Proliferative Retinopathy, Diabetic macular edema, Retinitis pigmentosa, Central vein occlusion and glaucoma and other related diseases or any other medical condition, is well understood in the art, and includes administration of a composition which reduces the frequency of, or delays the onset of, symptoms of a medical condition in a subject relative to a subject which does not receive the composition.

DETAILED DESCRIPTION OF THE INVENTION

Unless specifically defined herein, all technical and scientific terms used have the same meaning as commonly understood by a skilled artisan in the fields of medicine, pharmacology, pharmaceutical chemistry, biology, biochemistry and physiology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail.

Where a numerical limit or range is stated herein, the endpoints are included. Also, all values and sub ranges within a numerical limit or range are specifically included as if explicitly written out.

As previously discussed, there are a number of medical conditions including dry eye disease (DED) (Deinema et al., American Academy of Ophthalmology 2016, ISSN 0161-6420) that are either associated with low retinal omega-3 levels or which would benefit from increased levels of retinal long-chain omega-3 levels. DHA, EPA, DPA and SDA are omega-3 fatty acids of particular interest in this respect.

Thus, there is a need for means to increase the levels of omega-3 fatty acids in the retina, and in particular to increase the levels of DHA, EPA, DPA and/or SDA in the retina.

Unlike other tissues, the uptake of omega-3 does not occur through the lipoprotein receptors in the retina. Previous studies in animal models have reported that DHA in the form of LPC passes through the blood retinal barrier via Mfsd2a, the sodium-dependent lysophosphatidylcholine (LPC) symporter that transports LPCs containing DHA and other long-chain fatty acids.

Eye photoreceptor membrane discs in outer rod segments are highly enriched in the visual pigment rhodopsin and the omega3 fatty acid docosahexaenoic acid (DHA). The eye acquires DHA from blood, and it has been demonstrated LPC transport via Mfsd2a as an important pathway for DHA uptake in eye and for development of photoreceptor membrane discs. Further it has been demonstrated that Mfsd2a is highly expressed in retinal pigment epithelium in embryonic eye, before the development of photoreceptors, and is the primary site of Mfsd2a expression in the eye.

As reviewed by Querques et al, the retina has the highest concentration of DHA in the body, and several studies suggest that omega-3 polyunsaturated fatty acids could have a protective role in reducing the onset and progression of retinal diseases (Querques et al., J Nutr Metab. 2011; 2011: 748361). The high concentration of DHA is suggested to optimize fluidity of photoreceptor membranes, retinal integrity, and visual function. Furthermore, many studies demonstrated that DHA has a protective, for example antiapoptotic, role in the retina. In this review, it is disclosed that dietary uptake of omega-3 affects the incidence of AMD. Furthermore, a study with krill oil supplements have demonstrated that a moderate daily dose of omega-3 EFA in a predominantly phospholipid form (as in krill oil), for 3 months, resulted in reduced tear osmolarity and increased tear stability in people with DED. It was also demonstrated that the phospholipids from kill oil may confer additional therapeutic benefit, with improvements in DED symptoms and lower basal tear levels of interleukin 17A, relative to placebo (Deinema et al, 2017).

Even though dietary supplements containing omega-3 EFA in general seems to both influence the prevalence of ocular diseases and have a potential in the treatment of such diseases, it seems like the uptake and effects is influenced by in which form the omega-3's are delivered. This is demonstrated in the examples. For instance, example 4 describes that both the EPA and DHA content of the retina is more enriched from lipase-treated krill oil than with EPA and DHA from ordinary krill oil and fish oil. In view of the results, one object of the present invention is to provide compositions that will increase the uptake of EPA and DHA in the ocular tissue and retina, as well as optimizing the omega-6/omega-3 ratio in ocular tissue. Without being bound by theory, it is believed that increased uptake of Omega-3 essential fatty acids will alter the inflammatory status of the eye through modulating cytokine production, thus aid in treatment and prevention of inflammation. As most eicosanoids derived from the omega-6 fatty acid pathway are proinflammatory, omega-3 EFAs bias prostaglandin metabolism toward the production of anti-inflammatory eicosanoids, which limit and resolve inflammation.

A length of 14 carbon atoms or more have been indicted in the prior art to be essential for transport across the blood brain barrier (BBB) or the blood retinal barrier (BRB) by the Mfsd2a transporter. DHA, EPA, SDA and DPA are considered to be of high importance with respect to positive health effects in humans, and all of these have more than 14 carbon atoms. Thus, based on the information we have at date, each and all of these fatty acids should be transported efficiently across the blood retinal barrier when bound to LPC. LPC-DHA and LPC-EPA were therefore selected as model molecules in the present study (Example 2-4), but all data provided herein regarding uptake into the eye are also believed to indicate expected uptake profiles of the other two omega-3 fatty acids rereferred to above, i.e. SDA and DPA.

LPC-DHA and LPC-EPA were to be administered by both oral and intravenous administration in the study. For the intravenous administration, it was decided to mix the LPC-DHA and LPC-EPA with one or more pharmaceutically acceptable excipients. Intralipid (IV) provided by Sigma Aldrich is compatible with oily substances and was therefore selected as the one or more pharmaceutically acceptable excipients. Reference is made to example 1 for further details to the pharmaceutical composition that was used in Examples 2 to 4.

32 male Sprague Dawley rats received either an oral administration or a single intravenous administration of either LPC-DHA or LPC-EPA. The intravenous dose was administered directly into a tail vein as a slow bolus over 30 seconds. A single rat was euthanized by overdose of carbon dioxide gas at each of the following times: 0.5, 3, 8, 24, 72, 96, 168 and 336 hours post-dose. Each carcass was snap frozen in a hexane/solid carbon dioxide mixture immediately after collection and were then stored at approximately −20° C., pending further analysis. The frozen carcasses were subjected to quantitative ocular autoradiography, as detailed in example 2, to study the uptake of DHA and EPA into the ocular tissues at 0.5, 3, 8, 24, 72, 96, 168 and 336 hours post-dose.

Figure 8:
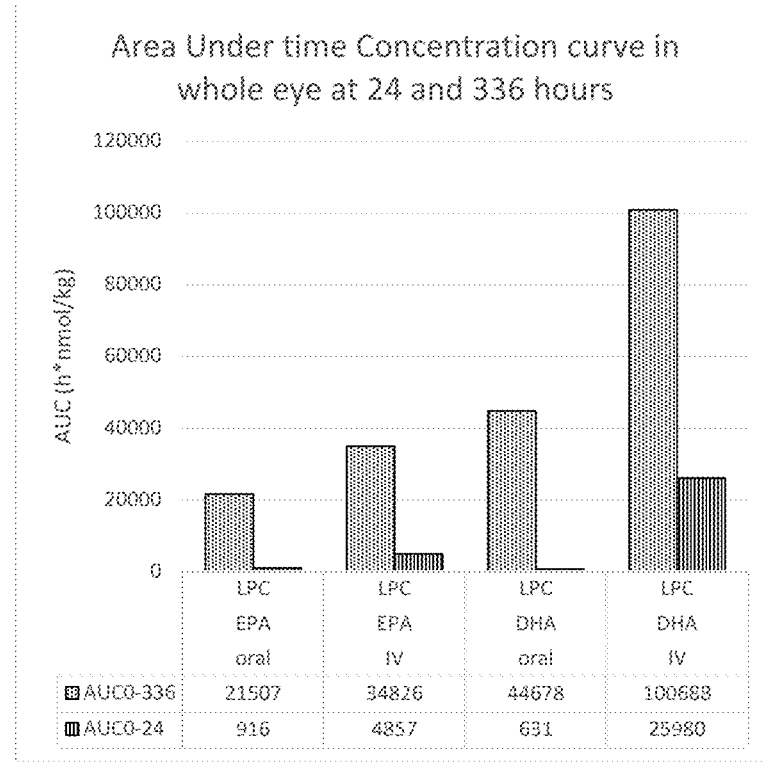
FIG. 8 shows area under time concentration curve of ocular tissue after oral and i.v. administration.
Figure 9:
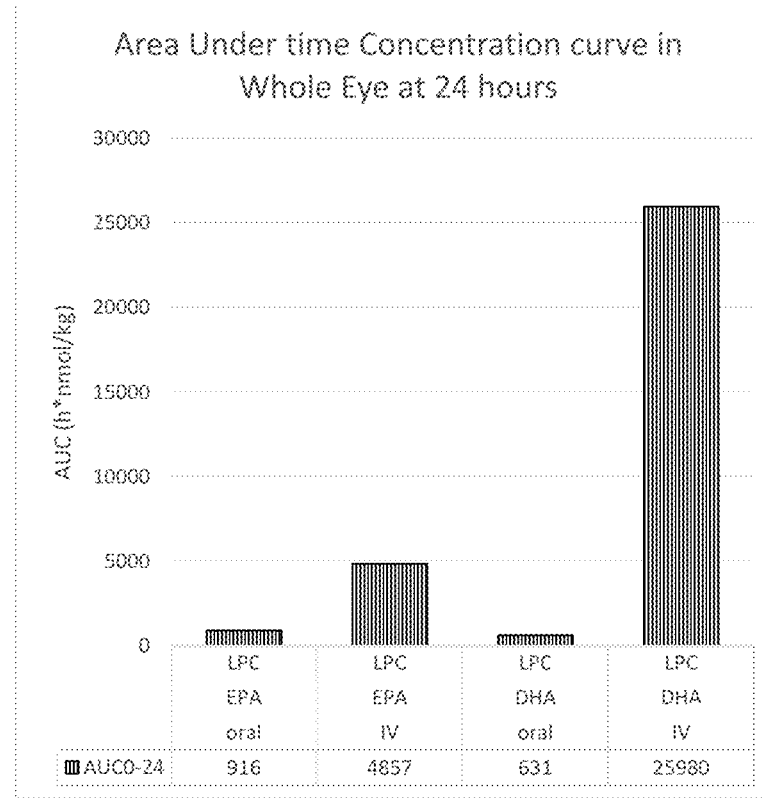
FIG. 9 shows area under time concentration curve of ocular tissue (whole eye) after oral and i.v. administration of LPC-EPA and LPC-DHA for the first 24 hours.
Figure 10:
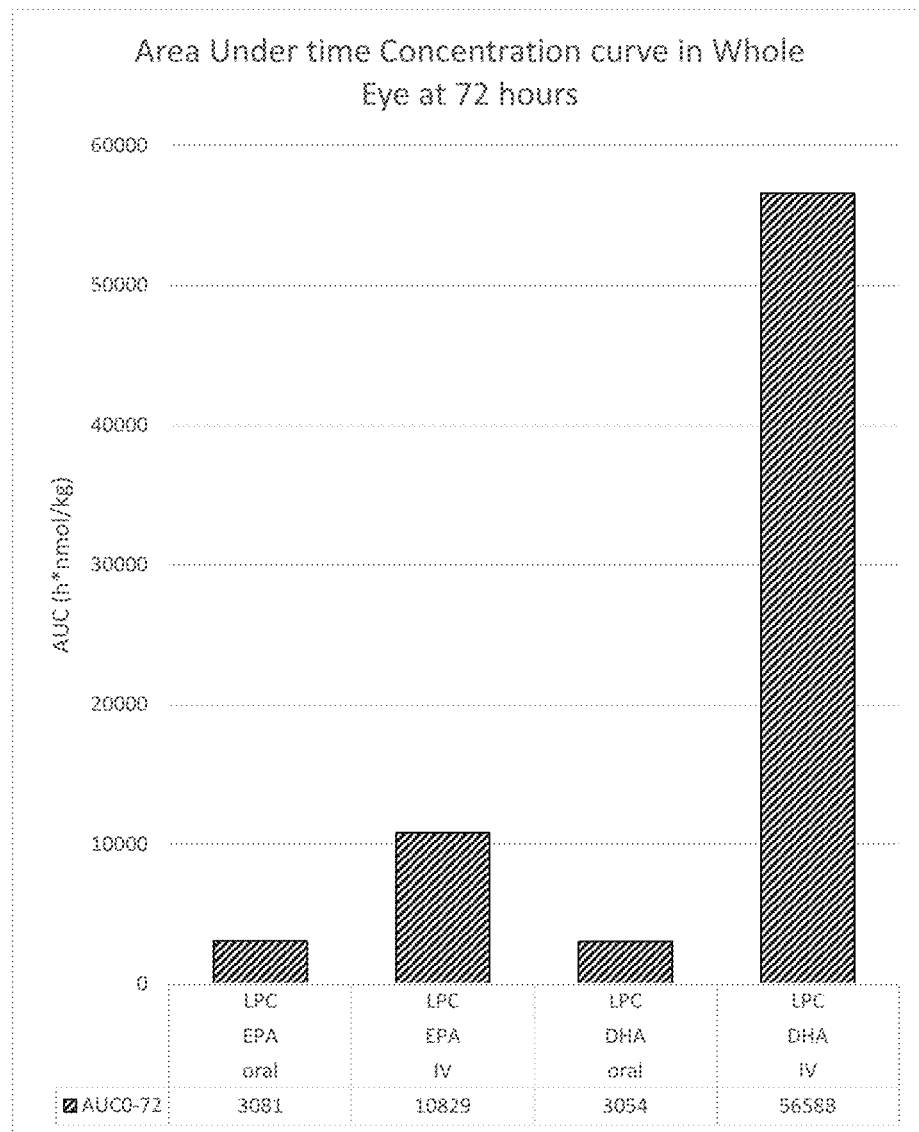
FIG. 10 shows area under time concentration curve of ocular tissue (whole eye) after oral and i.v. administration of LPC-EPA and LPC-DHA for the first 72 hours.

The final results of LPC-DHA are presented in example 2, table 1a and 1b. The final results of LPC-EPA are presented in example 3, table 2a and 2b. The data are also illustrated in FIGS. 8-10.

When administered intravascularly to avoid first exposure to the gut, DHA and surprisingly also EPA in its LPC form (as measured by their respective 14C radiolabelled carboxylic acid residues) exhibit very rapid and persistent uptake and massive accumulation into ocular tissue. For LPC-EPA given as a short intra vascular (i.v.) bolus the area under the concentration time curve (AUC) for the first 24 hours was demonstrated to be more than 5 times higher than the equivalent measure for the oral dose LPC. For LPC-DHA given as a short intra vascular (i.v.) bolus the area under the concentration time curve (AUC) for the first 24 hours was demonstrated to be more than 40 times higher than the equivalent measure for the oral dose LPC-DHA. This demonstrates that an administration route that can avoid first exposure to the gut results in a very rapid and persistent uptake of LPC-EPA and LPC-DHA into ocular tissue.

Example 3 provides data from a three-week daily dosing with different krill oil lysophospholipid compositions containing LPC-EPA and LPC-DHA. Twenty-four male rats were divided into groups and received daily oral gavage for 3 weeks, containing olive oil, different doses of LPC-compositions and Superba Boost krill oil. Retina FAs were extracted and analyzed.

Figure 2:
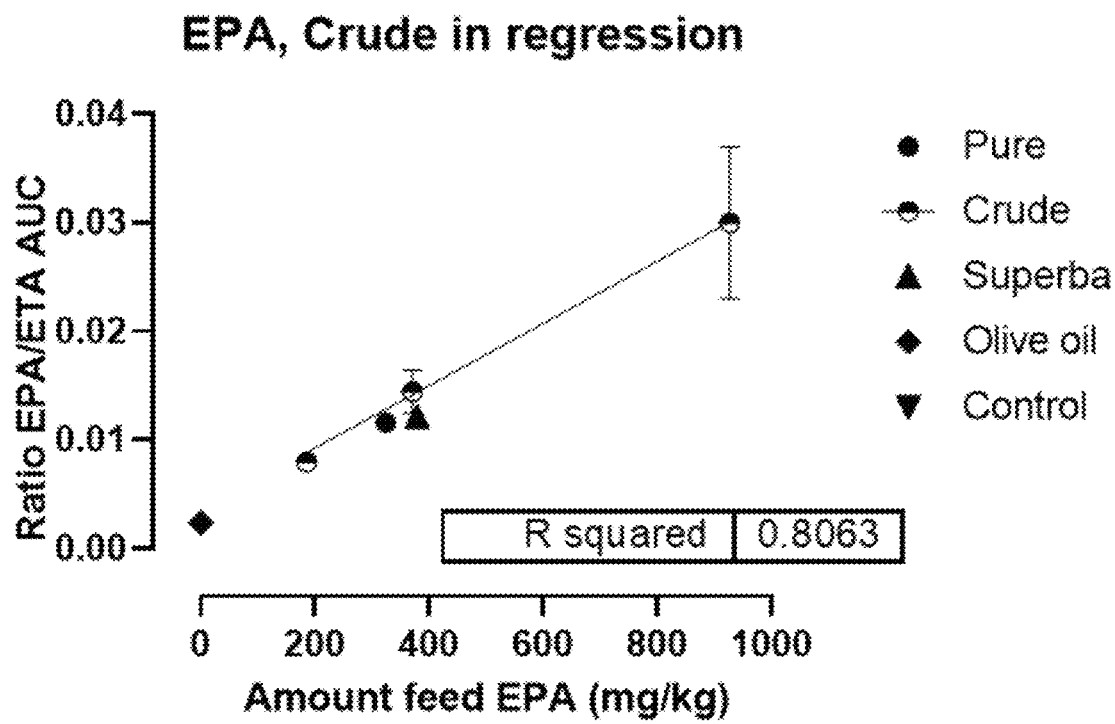
FIG. 2 shows retina EPA/ETA ratio at the conclusion of the study.
Figure 15:
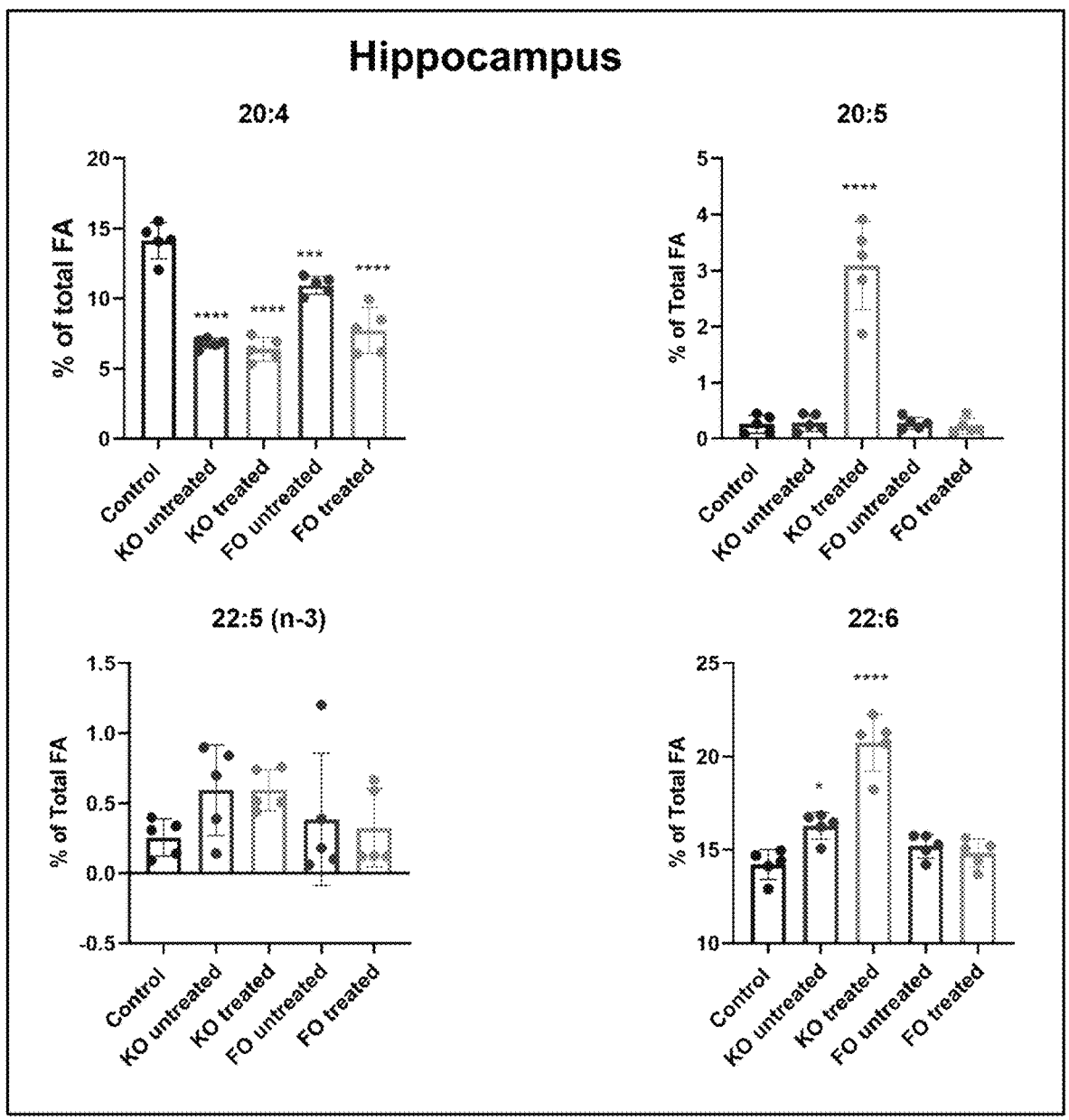
FIG. 15 shows the PUFA composition of hippocampus. The fatty acid composition was analyzed as described in the text. The values shown are mean±SD of 5 animals in each group. The symbols for statistical significance are the same as under FIG. 12.

FIGS. 1 and 2 show the results for EPA. It is demonstrated a strong dose-response relationship, where higher doses of EPA are associated with higher retina EPA concentrations (FIG. 1) and increases in the EPA/ETA (20:4) ratio (FIG. 2). One isomer of eicosatetraenoic acid (ETA) is arachidonic acid, an omega-6 fatty acid. The EPA/ETA ratio is an indicator of the omega-3/omega-6 shift that are occurring with enhanced uptake of omega-3 PUFAs. As explained, this is believed to positively affect the inflammatory status of the eyes. As described in the introduction omega-6 fatty acids have been linked to inflammation while the omega-3 fatty acids such as EPA and DHA have been linked to anti-inflammation signals. As can be seen by FIG. 15, rats fed with crude lysophospholipid compositions show a higher retina EPA/ETA ratio than rats fed with Superba Boost krill oil at similar doses. This implies that rats fed the LPC composition show a more favorable EPA profile in the retina as compared to rats fed Superba Boost krill oil and olive oil, and, furthermore, that higher doses of the lysophospholipid composition are associated with a more favorable EPA profile in the retina.

Figure 3:
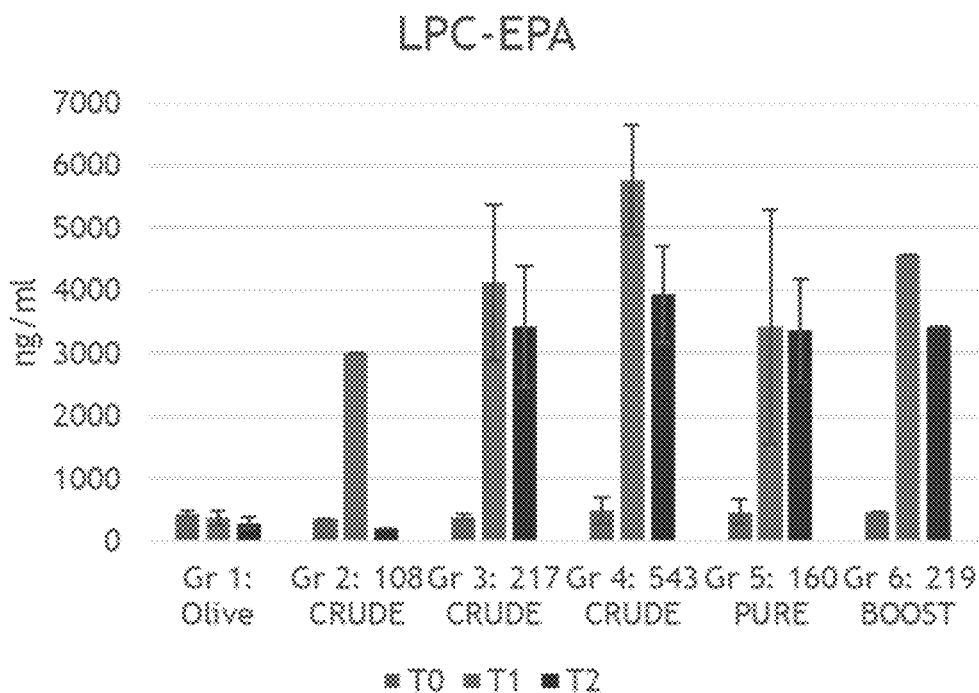
FIG. 3 shows plasma LPC-EPA (ng/ml) taken after 0 weeks (T0, baseline), 2 weeks (T1) and 3 weeks (T2) of oral gavage.

Inspection of FIG. 3 suggests that improvement in retina EPA profile is likely related to higher amounts of LPC-EPA being present in plasma and subsequent increased EPA uptake retina via mfsd2a. The crude for example provided in a high dose (Group 4) showing both the highest levels of LPC-EPA in plasma as well as the highest retina EPA content and an improved EPA to ETA ratio.

Figure 4:
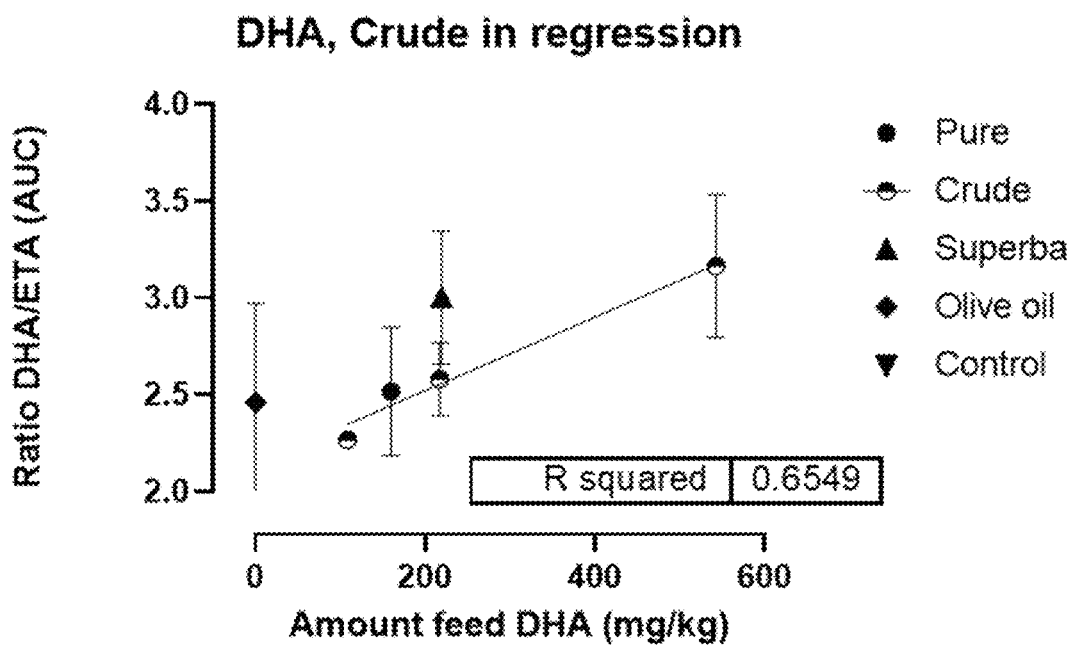
FIG. 4 shows retina DHA/ETA ratio at the conclusion of the study.
Figure 5:
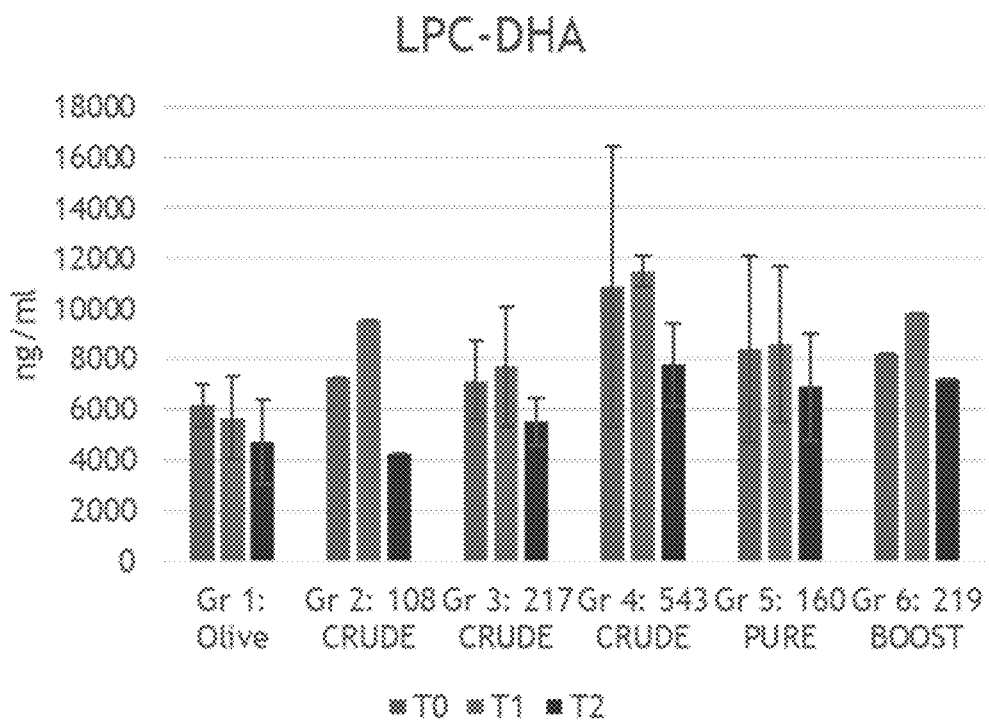
FIG. 5 shows plasma LPC-DHA (ng/ml) taken after 0 weeks (T0, baseline), 2 weeks (T1) and 3 weeks (T2) of oral gavage.

FIGS. 4 and 5 are related to results for DHA. For DHA it is also demonstrate a strong dose-response relationship, with higher doses of the lysophospholipid compositions being associated with a higher DHA/ETA ratio and a particularly pronounced increase in DHA/ETA ratio in the crude high dose group. This suggests that DHA is dose-dependently taken up into the retina from the lysophospholipid compositions irrespective in differences in lysophospholipid product purity.

FIG. 5 further depicts that the crude high dose group (Group 4) shows the highest levels of LPC-DHA at the end of the study period (T2), which supports the notion that DHA uptake across the blood-retina-barrier occurs via Mfsd2a.

Figure 6:
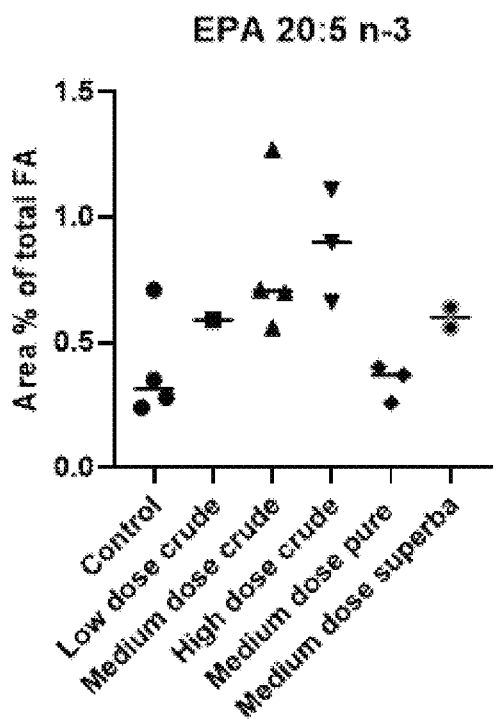
FIG. 6 shows retina concentration of EPA expressed as % of Total Fatty Acids for the six experimental groups.

FIG. 6 demonstrates eye EPA concentrations in relation to total fatty acids. As can be seen from FIG. 6, higher doses of the "crude" lysophospholipid composition is associated with higher retina EPA concentrations relative to total fatty acids.

Figure 7:
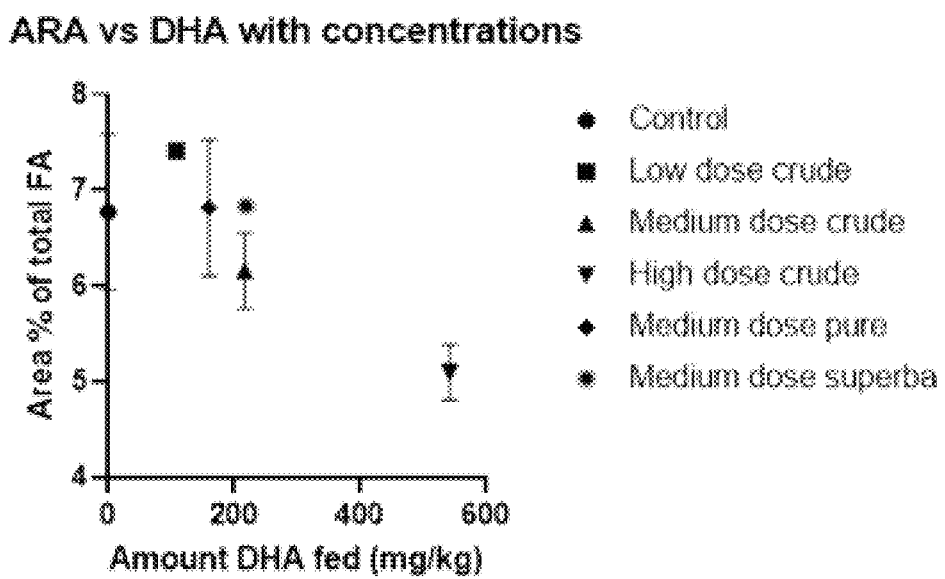
FIG. 7 shows the relationship between retina ARA (20:4 n-6) concentration and DHA dose for each of the six experimental groups.

FIG. 7 shows the relationship between Arachidonic acid (ARA; 20:4 n-6), DHA dose and test product. FIG. 7 shows that higher doses of the "crude" DHA/EPA lysophospholipid composition was associated with lower levels of retina ARA concentration relative to total fatty acids, and the crude lysophospholipid composition showed a more pronounced ARA decrease as compared to Superba Boost at comparable doses. This again suggests that increasing doses of the lysophospholipid composition is associated with a more beneficial fatty acid profile in the retina.

Accordingly, example 3 demonstrates that an oral administration route can result in a favourable fatty acid content of the retina, which will have a positive effect on the inflammatory status of the retina. Based on these results, the inventors propose an oral dietary supplement comprising the LPC-composition as described herein for use in therapy, such as prophylactic therapy, for eye diseases as disclosed herein.

Thus, in a first aspect the present invention relates to method for treating, preventing and/or relieving one or more symptoms and/or signs of a disease or condition of the eye comprising administering to a subject in need thereof an effective amount of a formulation comprising a lysophosphatidylcholine (LPC) composition comprising a LPC-compound selected from the group consisting of any one of formula 1 to 8, and any combination thereof so that the symptoms of the disease or condition are improved, controlled, reduced or alleviated:

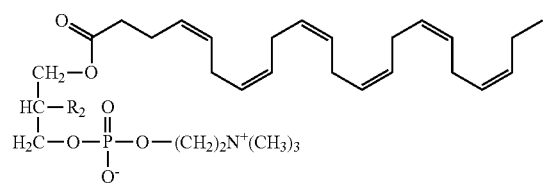

Formula 1

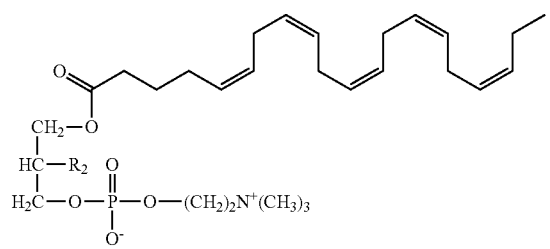

Formula 2

-continued

Formula 3
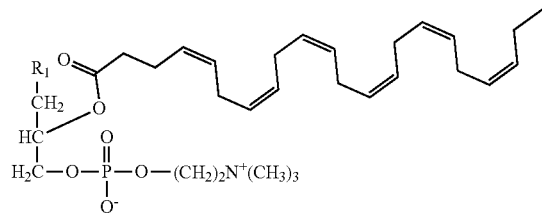

Formula 4
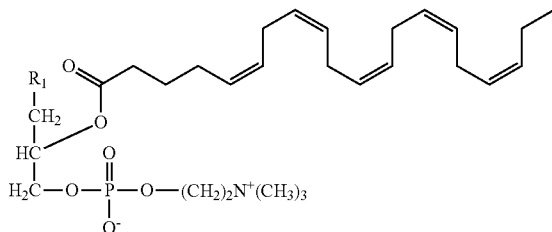

Formula 5
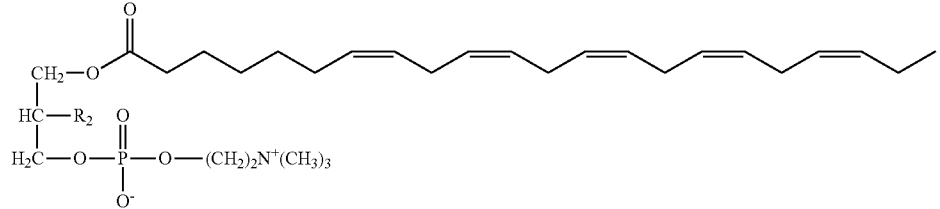

Formula 6
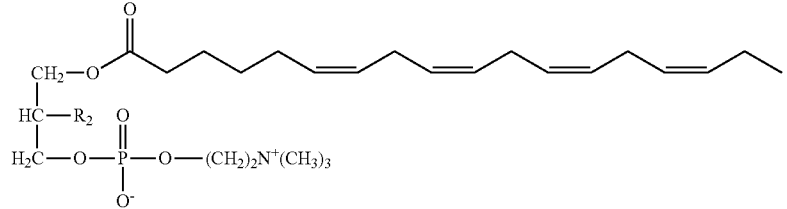

Formula 7
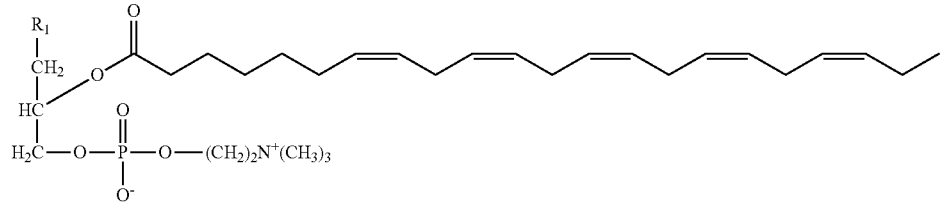

Formula 8
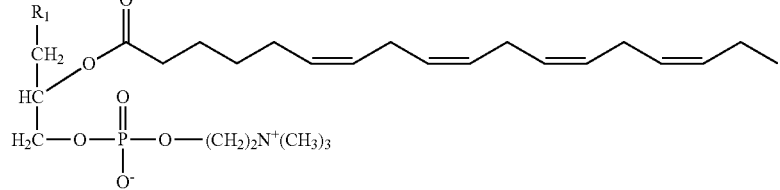

wherein
$R_1$ is OH or —OC(O)(CH$_2$)$_n$CH$_3$;
$R_2$ is OH or —OC(O)(CH$_2$)$_n$CH$_3$; and
n is 0, 1 or 2.

In one embodiment according to the present invention, $R_1$ is OH and $R_2$ is OH.

An alternative aspect according to the present invention relates to the first aspect of the present invention wherein $R_1$ is OH or a protecting group and $R_2$ is OH or a protecting group. One example of a protective group being —OC(O)(CH$_2$)$_n$CH$_3$, wherein n is 0, 1 or 2.

The protecting group is preferably a group which do not interfere with binding to the Mfsd2a transporter and at the same time it blocks migration of the omega-3 (i.e. DHA, EPA, SDA and DPA) acyl group. If the omega-3 fatty acid moiety (e.g. DHA moiety, EPA moiety, SDA moiety and DPA moiety) is positioned on the sn-1 position of the glycerol backbone, the protecting group will typically block migration of the omega-3 fatty acid moiety from the sn-1 position to the sn-2 position. If the omega-3 fatty acid moiety (e.g. DHA moiety) is positioned on the sn-2 position of the glycerol backbone, the protecting group will typically block migration of the omega-3 fatty acid moiety from the sn-2 position to the sn-1 position.

Formula 1 and 3 refers to a compound with an attached DHA moiety. Formula 2 and 4 refers to a compound with an attached EPA moiety. Formula 5 and 7 refers to a compound with an attached n-3 DPA moiety. Formula 6 and 8 refers to a compound with an attached SDA moiety. In practice, the DHA, EPA, DPA and SDA moieties may in principle be replaced by any omega-3 fatty acid as long as the omega-3 fatty acid has 14 or more C-atoms. However, DHA, EPA, DPA and SDA are believed to be of most relevance with respect to human eye health.

An alternative aspect according to the present invention relates to the first aspect of the present invention, wherein the DHA, EPA, DPA and SDA moieties are replaced by any omega-3 moiety; at least i) any omega-3 moiety which has 14 or more C-atoms in its chain or ii) any omega-3 moiety which has a length corresponding to a chain length of 14 or more C-atoms.

An alternative aspect according to the present invention relates to the first aspect of the present invention, wherein the DHA, EPA, DPA and SDA moieties are replaced by DHA, EPA, DPA, ALA and SDA moieties.

Throughout this application the term LPC-compound and the term "active component"/"active ingredient" all refers to compounds of formula 1 to 8.

The one or more active components referred to in the first aspect of the present invention, wherein $R_1$ is OH and $R_2$ is OH are all LPC molecules having either a DHA, an EPA, a DPA or a SDA molecule attached to the triacylglycerol moiety of LPC. Technical effect has been demonstrated for LPC-DHA and LPC-EPA. Based on the data presented in WO2018162617 and WO2008068413 it is also believed that similar effects would be obtained for the one or more active components referred to in the first aspect of the present invention where $R_1$ is —OC(O)(CH$_2$)$_n$CH$_3$; and $R_2$ is —OC(O)(CH$_2$)$_n$CH$_3$; and n is 0, 1 or 2, and in particular n=0.

Even though the results presented herein are impressive for i.v. administration of a formulation comprising an LPC-composition, the effect may be even further improved e.g. by including a pharmaceutically acceptable carrier. Liposomes may e.g. be suitable carriers for the oily constituents of the present invention by providing a hydrophobic interior for the oily substance and a hydrophilic exterior facing the hydrophilic environment. Further, it is also known that LPC is typically associated to proteins, such as albumin, in the blood to reduce the effective concentration of LPC.

The formulation comprising the LPC composition of the present invention may or may not comprise one or more solvents, such as ethanol and/or water. If the composition comprises one or more solvents, the amount of the one or more active components in the composition may be referred to as % by dry-weight of the composition. However, if the composition does not comprise one or more solvents, the amount of the one or more active components in the composition may be referred to as % by weight of the composition.

In one embodiment according to the present invention, the formulation comprising the LPC composition may comprise a combination of two or more of the one or more active components. One of the active components may have a DHA moiety attached to the glycerol backbone and another active component may have an EPA moiety attached to the glycerol backbone.

Thus, in one embodiment according to the present invention, the formulation comprising the LPC composition comprises a combination of two or more of the one or more active components. One of the active components having a DHA moiety attached to the glycerol backbone and the other active component having an EPA moiety attached to the glycerol backbone. In a preferred embodiment, there is a specific molar ratio of the active components having a DHA moiety attached to the glycerol backbone and the active components having an EPA moiety attached to the glycerol backbone. The molar ratio of the active components having a DHA moiety attached to the glycerol backbone: the active components having a EPA moiety attached to the glycerol backbone preferably being in the range 1:1 to 10:1, such as in the range 1:1 to 7:1, or in the range 1:1 to 5:1, or in the range 1:1 to 3:1. In another embodiment according to the present invention, the molar ratio of the active components having a EPA moiety attached to the glycerol backbone: the active components having a DHA moiety attached to the glycerol backbone preferably being in the range 1:1 to 10:1, such as in the range 1:1 to 7:1, or in the range 1:1 to 5:1, or in the range 1:1 to 3:1.

Reference is made to the following example illustrating how the molar ratio is to be calculated. If a composition comprises 10 mol LPC-DHA and 2 mol LPC-EPA, then the molar ratio of the active components having a DHA moiety attached to the glycerol backbone and the active components having a EPA moiety attached to the glycerol backbone is 10:2, i.e. 5:1. If not specified otherwise, the number of moles of LPC-EPA is the number of moles 1-LPC-EPA+the number of moles 2-LPC-EPA and the number of moles of LPC-DHA is the number of moles 1-LPC-DHA+the number of moles 2-LPC-DHA.

It has previously been discussed that the position of the omega-3 fatty acid moiety on the glycerol backbone may affect the uptake of that fatty acid into the eye. Thus, in one embodiment according to the present invention, the listed omega-3 fatty acid moieties are bond to sn1 position of the glycerol backbone. In another embodiment according to the present invention, the listed omega-3 fatty acid moieties are bond to sn2 position of the glycerol backbone. In an alternative embodiment according to the present invention, there is a specific molar ratio of the active components having an omega-3 fatty acid moiety bound to sn1 position of the glycerol backbone and the active components having an omega-3 fatty acid moiety bound to sn1 position of the glycerol backbone. The molar ratio of the active components having an omega-3 fatty acid moiety bound to sn2 position of the glycerol backbone: the active components having an omega-3 fatty acid moiety bound to sn1 position of the glycerol backbone preferably being in the range 1:8 to 18:1, such as in the range 1:8 to 15:1 or in the range 1:8 to 10:1.

Reference is made to the following example illustrating how the molar ratio is to be calculated. If a composition comprises 5 mol 2-LPC-DHA, 5 mol 2-LPC-EPA and 2 mol 1-LPC-DHA, then the molar ratio of the active components having an omega-3 fatty acid moiety bound to sn1 position of the glycerol backbone: the active components having an omega-3 fatty acid moiety bound to sn2 position of the glycerol backbone is 10:2, i.e. 5:1.

Figure 11:
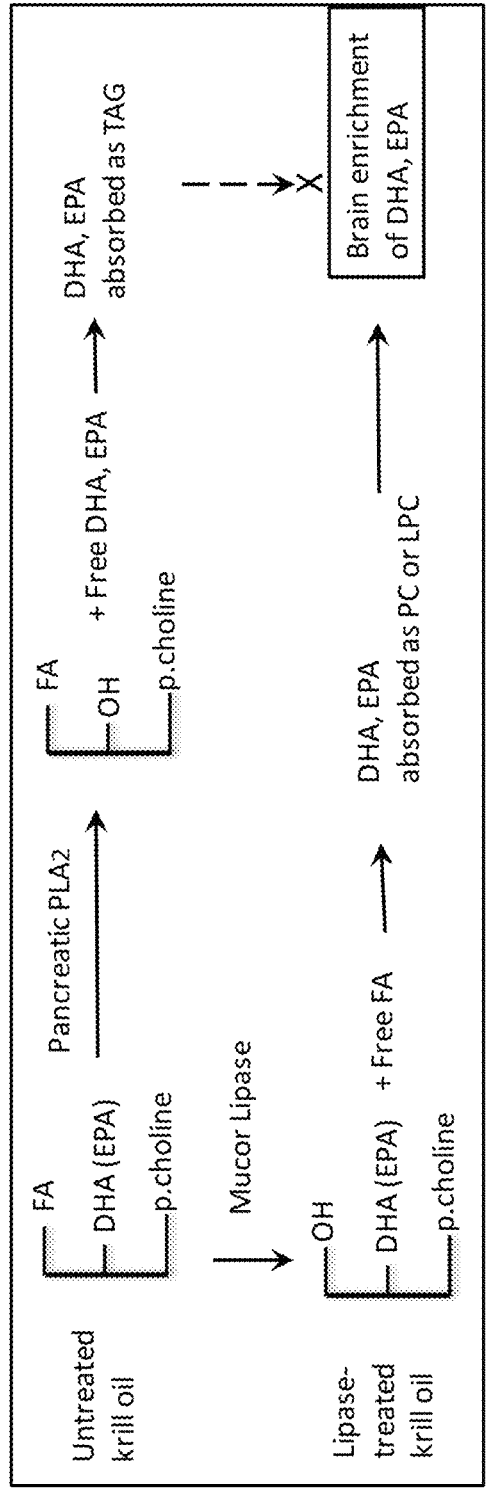
FIG. 11 shows that Krill oil contains EPA and DHA in the sn-2 position of PC, and are therefore released as free fatty acids during digestion by the pancreatic phospholipase $A_2$. The released EPA and DHA are then absorbed as TAG, which does not generate LPC-EPA or LPC-DHA required for transport into the brain. Therefore, feeding krill oil does not result in significant enrichment of EPA and DHA in the brain. However, if we pre-treat krill oil with a lipase which is specific for the sn-1 ester bond, LPC-EPA and LPC-DHA would be generated. Feeding this modified krill oil should result in the absorption of EPA and DHA in the phospholipid form, leading to their enrichment in the brain. Lipase treatment of fish oil, on the other hand, will not generate LPC-EPA or LPC-DHA, and therefore would not result in brain enrichment of EPA and DHA (not shown).

A second aspect of the present invention relates to krill oil compositions enriched in LPC-DHA and LPC-EPA. Although krill oil contains significant amounts of EPA and DHA in the form of phospholipids, these fatty acids are in the sn-2 position of the phospholipids, and are released by the pancreatic PLA$_2$ as free acids during digestion, then absorbed as TAG, and therefore are not efficiently transported into the brain (16). However, if we pre-treat the krill oil with a lipase which is specific for the sn-1 position, the EPA and DHA is released as LPC, which would then be absorbed as phospholipids and would be more likely to be incorporated into the brain (FIG. 11).

On the other hand, since fish oil contains no phospholipid, its treatment with the lipase would not generate LPC-EPA or LPC-DHA, but releases the omega 3 fatty acid either as free acid or as monoacylglycerol, which are absorbed as TAG and would therefore not enrich brain omega 3 fatty acids. In this study we compared the ability of fish oil and krill oil before and after treatment with a lipase to enrich brain omega 3 fatty acids in normal mice. The results clearly show that lipase treatment of krill oil results in enrichment of brain EPA and DHA, whereas lipase treatment of fish oil showed no effect on its ability to increase brain EPA or DHA.

The krill oil compositions of some further embodiments of the invention are prepared by hydrolyzing krill oil in the presence of an excess of a lipase specific for the sn-1 position of krill oil phospholipids under an inert atmosphere at a temperature of about 40° C. to about 50° C. for an amount of time sufficient to ensure substantially complete hydrolysis of the sn-1 ester bond. Suitable lipases include lipase from *Mucor meihei*, *Rhizopus oryzae* lipase, Novozyme 435 (from *Candida* sp) and Lipozyme TLIM (from *Thermomyces* sp), and the like. In some embodiments, the lipase comprises lipase from *Mucor meihei*. In some embodiments, the krill oil is hydrolyzed using up to a 50 percent excess by weight of lipase. In some embodiments, the lipase is immobilized.

In a particular embodiment, a solution of krill oil in 95% ethanol is treated with 1.33× by weight of immobilized lipase from *Mucor meihei* at 40° C. with agitation for about 72 hours followed by evaporation of the ethanol to provide the lipase-treated krill oil composition.

The lipase-treated krill oil prepared as described herein may be further purified for use as a food additive or incorporation into a nutraceutical or pharmaceutical composition. Methods for purifying krill oil compositions are known in the art and may include solvent extraction, chromatography, and the like. Chromatographic purification typically involves loading the lipid extract on to a silica gel column and eluting with solvents of increasing polarity. After removal of neutral lipids and unreacted phospholipids, the lyso PC was eluted with methanol to yield pure compound containing about 85% EPA and DHA.

Also disclosed herein are compositions comprising the lipase-treated krill oil of the invention. The formulations, compositions, or substances of this invention may be prepared in a number of ways, including as a dry powder, as a capsule, as a ready to drink juice or as a food additive. Alternatively, the formulation may also be brewed, fermented, boiled to create a compote, prepared as an alcohol or water extract. In general, any formulation using an extract as described herein in any manner will be within the spirit of the invention.

In an embodiment, the lipase-treated krill oil composition may be packaged and sold as a powder. The powder may then be reconstituted with water or blended with foods and thereby be ingested for medicinal, preventive, nutritional, or otherwise health related purposes. Alternatively the powder may be encapsulated. The capsule may then be swallowed, or broken open to be used as the powder described above. Finally, the powder can be formed into a solid pill. The solid pill can be dissolved in water for intake, crushed into a powder as described above, or it can be swallowed.

The lipase-treated krill oil may be incorporated into solid compositions. Solid compositions may include conventional nontoxic solid carriers including, for example, pharmaceutical grades of mannitol, lactose, starch, magnesium stearate, sodium saccharin, talc, cellulose, glucose, sucrose, magnesium carbonate, and the like.

Liquid compositions can, for example, be prepared by dissolving, dispersing, and the like, the lipase-treated krill oil as described herein and optional adjuvants in an excipient, such as, for example, water, saline, aqueous dextrose, glycerol, ethanol, and the like, to thereby form a solution or suspension. If desired, the liquid composition can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

Other embodiments include the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, hypromellose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Formulations for buccal administration include tablets, lozenges, gels and the like. Alternatively, buccal administration can be effected using a transmucosal delivery system as known to those skilled in the art. The extracts of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one aspect, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

The lipase-treated krill oil may be formulated as an ointment or cream. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Another aspect of the present invention provides a food composition including the lipase-treated krill oil of the invention. In certain embodiments, the lipase-treated krill oil according to the present invention may be used as an active ingredient in a health functional food or a general food. The food composition of the present invention may be used to prevent or treat neurological diseases such as Alzheimer's. In this case, lipase-treated krill oil of the present invention may be added without further processing or may be used together with other foods or food ingredients in accordance with methods known in the art. The amount of the active ingredient may be suitably determined according to its intended purpose, such as prophylactic, health care or therapeutic purpose. The food composition of the present invention may further contain one or more additives selected from nutrients, vitamins, electrolytes, flavoring agents, coloring agents, pectic acid and its salts, alginic acid and its salts, organic acids, protective colloidal thickeners, pH adjusting agents, stabilizers, preservatives, glycerin, alcohols, and carbonating agents for carbonated drinks. The food composition of the present invention may further contain flesh or vegetative pulp for the production of natural fruit juices, fruit juice beverages, and vegetable beverages. Such ingredients may be used independently or as a mixture thereof. The proportions of such additives are not limited but are typically selected from the range of 0.01 to 0.1 parts by weight, based on 100 parts by weight of the composition of the present invention.

When it is intended to produce a food or beverage, the lipase-treated krill oil of the invention is typically added in an amount of 15 parts by weight or less, preferably 10 parts by weight or less, based on 100 parts by weight of the raw materials of the food or beverage. In the case where the food or beverage is taken for a long time for the purpose of health and hygiene or health care, the amount of the broccoli or extract may be adjusted to less than the lower limit defined above. The food composition of the present invention is free from problems associated with safety because it uses the natural product or broccoli plant extracts consisting solely of naturally-occurring chemicals. Accordingly, the broccoli or extract may also be used in an amount exceeding the upper limit defined above.

There is no particular restriction on the kind of the food. Examples of foods that may be added with the lipase-treated krill oil include all common foods, such as meats, sausages, breads, chocolates, candies, snacks, cookies, pizzas, instant noodles, other noodles, chewing gums, dairy products including ice creams, soups, beverages, teas, drinks, alcoholic beverages, and vitamin complexes.

Beverages may contain one or more additional ingredients, such as flavoring agents or natural carbohydrates, like general beverages. The natural carbohydrates may be monosaccharides, such as glucose and fructose, disaccharides, such as maltose and sucrose, polysaccharides, such as dextrin and cyclodextrin, and sugar alcohols, such as xylitol, sorbitol, and erythritol. The beverage may contain one or more sweetening agents. As the sweetening agents, there may be used, for example, natural sweetening agents, such as thaumatin and *stevia* extract, and synthetic sweetening agents, saccharine and aspartame.

A third aspect of the present invention relates to a formulation comprising a LPC composition according to the first or second aspect of the present invention for use in prophylaxis and/or therapy. In some preferred embodiments, the formulation is to be administered orally or intravascularly.

The ocular surface may be subject to specific disorders, such as dry eye (1) and corneal lesions (2).

The correct hygiene of the periocular area (3) is essential for the health of the ocular surface and of the eye as a whole.

In a preferred embodiment according to the fourth aspect of the present invention, the condition which would benefit from increased levels of retinal DHA and/or EPA levels is ocular surface disorders.

Dry Eye Disease (DED) is one of the most common eye conditions worldwide and a primary reason for visits to the eye doctor.

DED is a multifactorial disease that affects the tear film and the ocular surface and causes symptoms of discomfort, visual disturbances and instability of the tear film, with potential damage to the ocular surface, accompanied by an increase in tear film osmolarity and ocular surface inflammation (definition by DEWS II—2017).

In a preferred embodiment according to the fourth aspect of the present invention, the condition which would benefit from increased levels of retinal DHA and/or EPA levels is dry eye disease.

Corneal Lesions

The cornea is the transparent membrane, located in front of the iris, which works as the most powerful converging lens of the human eye.

Lesions affecting the cornea are quite frequent and are usually associated with the following development of inflammation.

Corneal injuries include abrasions (such as scratches or scrapes limited to the eye surface), chemical damages (caused by fluids that get into the eye), lesions due to contact lenses or foreign bodies.

There are also the corneal lesions due to surgical treatments involving the anterior segment of the eye.

Glaucoma is a chronic degenerative disease that affects the optic nerve, characterized by damage to the nerve fibers that constitute it and the consequent loss of the visual field. If left untreated, the progressive reduction of the visual field may lead to blindness.

Glaucoma is a major social problem: it is the second leading cause of blindness worldwide and affects about 60 million people, making more than 8 million blind. In addition, approximately 50% of subjects with glaucoma are unaware of suffering from it.

It is an insidious disease because we often discover the disease when vision changes are already very advanced while we do not notice any symptom before. However, if diagnosed early and treated appropriately, it can be controlled effectively, allowing good vision for the rest of the patient's life.

There are many risk factors associated with the onset of the disease. The main ones are:
high intraocular pressure (TOP),
old age,
familiar predisposition.

The TOP value is determined by a liquid that circulates inside the eye, the aqueous humour.

In a healthy eye, the ratio between the aqueous humour produced and that eliminated is such to maintain a constant intraocular pressure, typically between 11 and 20 mmHg. While in the presence of glaucoma, this ratio is altered due to a reduction in the elimination outflow of the aqueous humour which occurs at the level of the trabecular meshwork (a structure that allows the outflow of this fluid from the eye).

Glaucoma can be classified in several ways:
according to etiology, glaucoma can be primary, when it occurs in the absence of other eye or systemic diseases, or secondary, when combined with pre-existing conditions;
according to the alteration of the outflow of aqueous humour, we distinguish the open angle glaucoma, due to an increased outflow resistance at the level of the trabecular meshwork and angle closure glaucoma, where there are anatomical problems that prevent the arrival of the aqueous humour to the trabecular meshwork;
based on the value of the main risk factor, the IOP, we distinguish high pressure glaucoma and normal pressure glaucoma.

Then, there are congenital or acquired glaucoma, if the IOP is higher than normal since birth, and infantile glaucoma if it arises during the first few years of life.

In a preferred embodiment of the present invention, the formulation comprising a LPC composition according to the first or second aspect is provided for use to inhibit, prevent, or treat glaucoma.

Retinal Disorder

A healthy retina is essential for vision because retinal specialized photoreceptors, cones and rods, convert light stimuli into electrical impulses, transmitted through the optic nerve to the brain, where the processing and perception of the visual image happens.

Many serious pathologies can affect the retina such as:
Age-related Macular Degeneration (AMD) that causes progressive damage to the macula, the central and most vital area of the retina, leading to the gradual loss of central vision.
Diabetic Retinopathy (DRP): the main and most common ocular complication of diabetes. DRP is characterized by lesions affecting the retinal capillaries in patients suffering from both type 1 or type 2 Diabetes Mellitus (DM). It can cause blindness if left undiagnosed and untreated.
Diabetic Macular Edema (DME) is one of the major complications of Diabetes, together with DRP, and if untreated can seriously hinder central vision. The chances to develop DME increase together with the length and severity of Diabetes: around 30% of patients suffering from DM for more than 20 years develop DME.

In a preferred embodiment according to any of the above aspect, the condition which would benefit from increased levels of retinal DHA and/or EPA levels is dry eye disease such as inflammation of the eye, corneal nerve abnormalities and abrasions on the surface of the eye.

In some embodiments, the inflammatory diseases of the eye including corneal dystrophy, trachoma, onchocerciasis, uveitis, sympathetic ophthalmitis and endophthalmitis.

In an alternative embodiment according to any of the above aspects the condition which would benefit from increased levels of retinal DHA and/or EPA levels is a neurodegenerative disease of the eye selected from the group consisting of age-related macular degeneration, diabetic retinopathy, Non-Proliferative Retinopathy, Proliferative Retinopathy, Diabetic macular edema, Retinitis pigmentosa, Central vein occlusion and glaucoma.

The LPC Composition

In some preferred embodiments, the LPC compositions are analyzed according to the methods as described in WO 2019/123015, incorporated by reference herein in its entirety.

In some embodiments according to any of the above aspects the LPC composition comprises at least one of the LPC compounds of formulas 1 to 8, and any combination thereof:

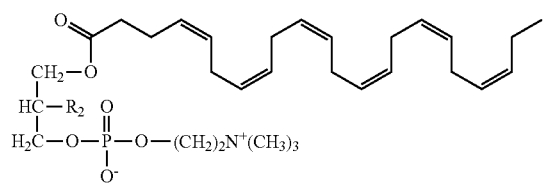

Formula 1

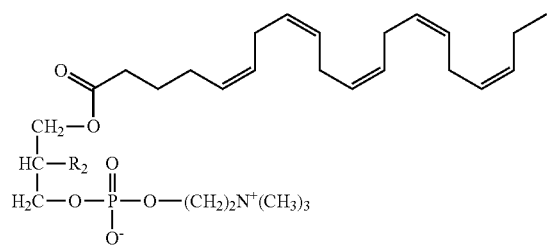

Formula 2

-continued

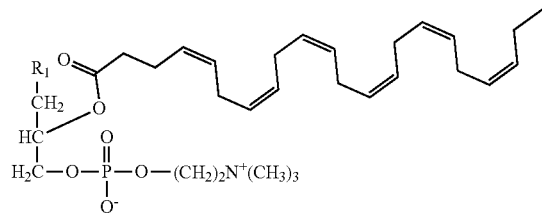
Formula 3

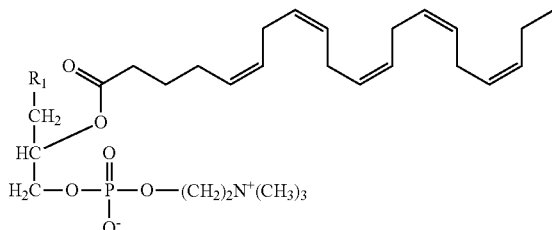
Formula 4

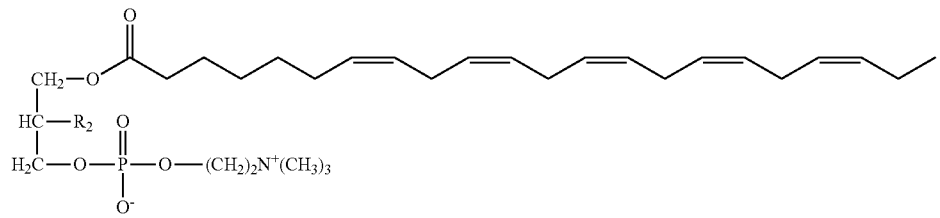
Formula 5

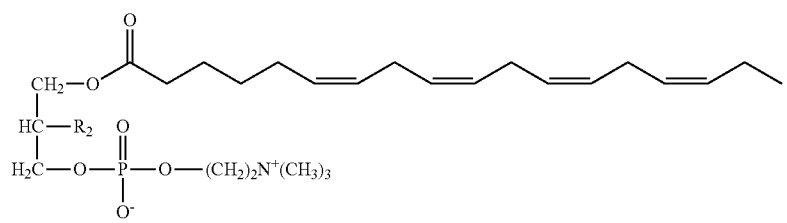
Formula 6

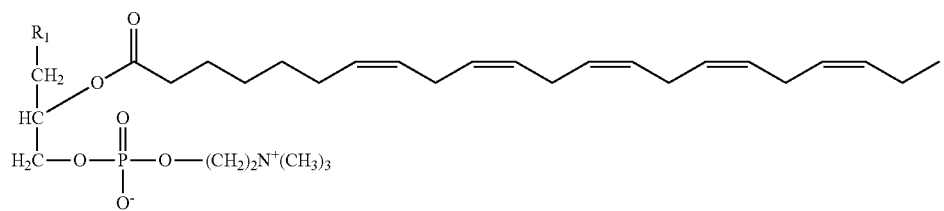
Formula 7

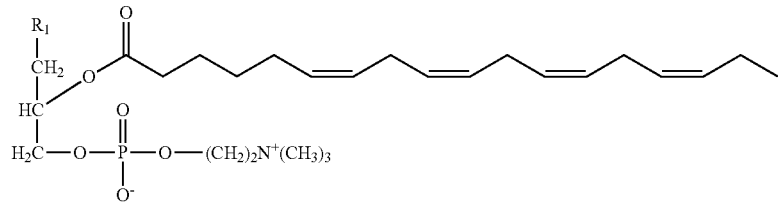
Formula 8

In some embodiments, the LPC composition further comprises a lipid different from LPC, selected from the group consisting of triglycerides, ethyl esters, free fatty acids and phospholipids such as phosphatidylethanolamine and phosphatidylcholine. In some embodiments, the lipid different from the LPC is from a different source, such as a non-krill source.

In some embodiments, the LPC composition comprises an amount of total LPC corresponding to from 10-100% by weight of the LPC composition, such as from 10% to 100% by weight, preferably 15% to 100% by weight, more preferably 20% to 100% by weight, further preferably 30% to 100% by weight, most preferably 50% to 100% by weight of the LPC composition.

In some embodiments, the LPC composition comprises a fatty acid profile wherein the amount of DHA corresponds to from 5% to 12% by weight of the composition, wherein the DHA is as free fatty acid or as ethyl ester or bound to any lipid in the LPC composition.

In one embodiment, the LPC composition comprises a fatty acid profile wherein the amount of EPA corresponds to from 10% to 24% by weight of the composition, wherein the EPA is as free fatty acid or as ethyl ester or bound to any lipid in the LPC composition.

In one embodiment, the LPC composition further comprises palmitoleic acid and/or palmitic acid.

In one embodiment, the LPC composition comprises a fatty acid profile wherein the amount of palmitoleic acid corresponds to from 2% to 5% by weight of the composition, wherein the palmitoleic acid is as free fatty acid or as ethyl ester or bound to any lipid in the LPC composition.

In one embodiment, the LPC composition comprises a fatty acid profile wherein the amount of from 10% to 15% by weight of the composition, wherein the palmitic acid is as free fatty acids or as ethyl esters or bound to any lipid in the LPC composition.

In one embodiment, the LPC composition comprises an amount of total phospholipids corresponding to at least 35% by weight of the LPC composition.

In further embodiments, the LPC composition comprises a predominant amount or a major portion of at least one LPC compound according to the invention compared to an amount of phosphatidylcholine.

In one embodiment, the LPC composition comprises an amount of total LPC corresponding to at least 23, 24, 25, 26, 27 or 28% by weight of the LPC composition.

In one embodiment, the LPC composition comprises an amount of total LPC corresponding to at least 60% by weight of the LPC composition.

In one embodiment of the first aspect, the LPC composition comprises an amount of total LPC corresponding to at least 90% by weight of the LPC composition.

In one embodiment of the first aspect, the LPC composition comprises an amount of total LPC corresponding to from 90% to 98% by weight of the LPC composition.

In one embodiment of the first aspect, the LPC composition comprises an amount of total LPC corresponding to about 95% by weight of the LPC composition.

For instance, in one embodiment the LPC composition comprises from 60% to 100% by weight of total LPC, such as about 60% to 95% by weight of total LPC.

In some embodiments of the invention, the LPC compound is any krill-derived processed phospholipid product containing a predominant amount of LPC compared to PC manufactured by Aker Biomarine.

In a further embodiment of any of the above aspect the LPC compound is selected from LPC-EPA, LPC-DHA and any combination thereof.

In further embodiments of any of the above aspects, the LPC composition is a krill oil LPC composition. In some preferred embodiments, the krill oil LPC composition is enriched for LPC-EPA and LPC-DHA. In some preferred embodiments, the krill oil composition is lipase-treated krill oil. In some embodiments, the lipase treated krill oil is made as described in Example 4. In some preferred embodiments, the lipase-treated krill oil comprises at least 80% by weight LPC-DHA and LPC-EPA. In some preferred embodiments, the lipase is a lipase from *Mucor meihei*. In some preferred embodiments, the lipase is immobilized.

Other Therapeutic Uses

In a sixth aspect, the present invention relates to use of the compositions and formulations described in the first and second aspects above to treat neurological disorders. In some embodiments, the neurological disorder is selected from Parkinson's, schizophrenia, traumatic brain injury, stroke and Alzheimer's. In some particularly preferred embodiments, the neurological disorder is Alzheimer's disease.

In a seventh aspect, the present invention relates to use of the compositions and formulations described in the first and second aspects above to treat a liver disease mitigated by DHA enrichment of the liver. In some preferred embodiments, the liver disease is selected from non-alcoholic fatty liver (NAFLD) and non-alcoholic steatohepatitis (NASH).

Having generally described this invention, a further understanding can be obtained by reference to certain specific examples, which are provided herein for purposes of illustration only, and are not intended to be limiting unless otherwise specified.

EXPERIMENTAL

Example 1: Preparation of Oral and Intravenous Formulations Used in Examples 2 to 4

Materials

| Intralipid (IV dose) | |
|---|---|
| Source/supplier | Sigma Aldrich |
| CAS number | 68890-65-3 |
| Physical form/appearance | White liquid |
| Constituents/concentrations | 20% fat emulsion |

| LPC - Modified krill oil solution (oral dose) | |
|---|---|
| Source/supplier | Aker BioMarine |
| Batch/lot number | LS:ABM_9C0 |
| Physical form/appearance | Red oil |
| Constituents/concentrations | 950 mg/g |

| [$^{14}$C]-LPC-EPA | |
|---|---|

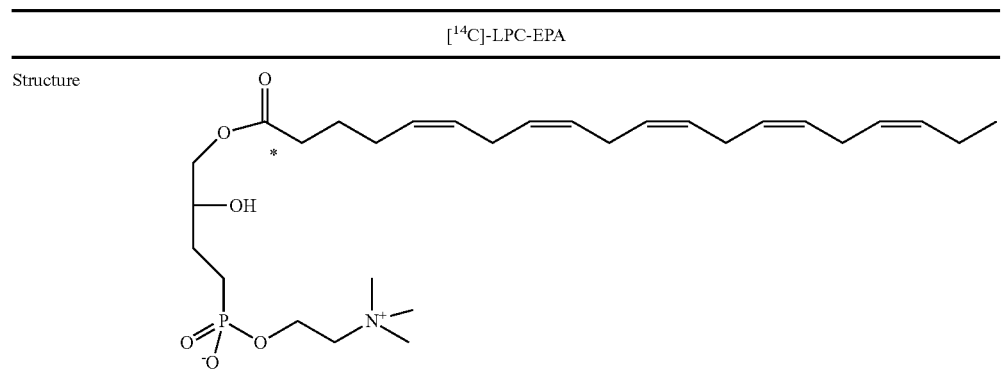

| | |
|---|---|
| Source/supplier | Pharmaron UK |
| Physical form/appearance | Ethanolic solution |
| | 3 mCi/g [2.361 mCi/mL accounting for specific gravity of ethanol (0.787)] |
| Molecular weight | 543.5 |
| Specific activity | 57 mCi/mmol (2.11 GBq/mmol) |
| Radiochemical purity | 96.3% |

| [14C]-LPC-DHA | |
|---|---|
| Structure | 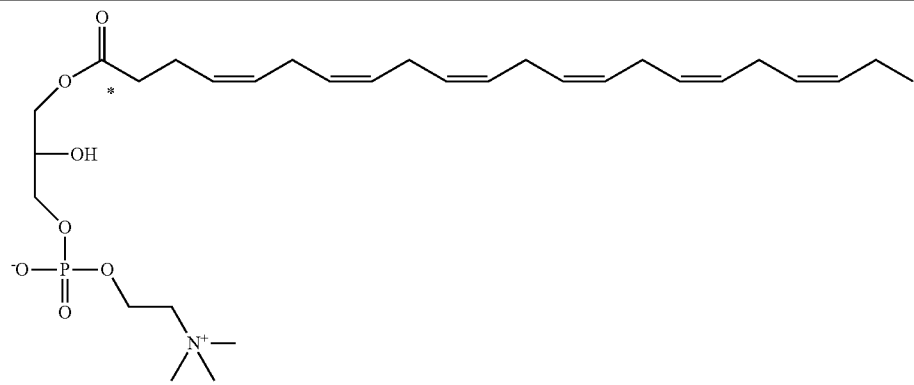 |
| Source/supplier | Pharmaron UK |
| Physical form/appearance | Ethanolic solution |
| | 3 mCi/g [2.361 mCi/mL accounting for specific gravity of ethanol (0.787)] |
| Molecular weight | 569.6 |
| Specific activity | 58 mCi/mmol (2.15 GBq/mmol) |
| Radiochemical purity | 98.0% |

[$^{14}$C]-LPC-DHA Formulation, Herein Referred to as Formulation A

The formulation that was later administered intravenously was prepared according to the following target specifications:

| Dose regimen and route | Single IV |
|---|---|
| Dose level | About 1.5 mg/kg radiolabeled compound + 190 mg/kg of intralipid |
| Radioactive dose | 155 µCi/kg |
| Dose volume | 1 mL/kg |
| Dose concentration | 190 mg/mL @ 5:95 ethanolic [$^{14}$C]-LPC-DHA:intralipid (20%) v/v |
| Dose vehicle | 5:95 v/v ethanol:injectable intralipid (20% emulsion) |
| Formulation specific radioactivity | 3 mCi/g |
| Dose formulation radioactive concentration | 1.5215 mg/mL |

The [$^{14}$C]-LPC-DHA was mixed with the intralipid formulation to yield a dose formulation containing phospholipids at a final concentration of 190 mg/kg and the [$^{14}$C]-LPC-DHA at a concentration of about 1.5 mg/kg (155 µCi/kg) as follows:

0.394 mL of ethanolic [$^{14}$C]-LPC-DHA (2361 µCi/mL) was dispensed into a 20 mL glass vial and reduced to a final volume of approximately 0.30 mL under a flow of nitrogen at ambient temperature. 5.70 mL of 20% intralipid was added to the concentrated ethanolic [$^{14}$C]-LPC-DHA solution and gently vortex mixed to ensure homogeneity.

[$^{14}$C]-LPC-EPA Formulation, Herein Referred to as Formulation B

The formulation that was later administered intravenously was prepared according to the following target specifications:

| Dose regimen and route | Single IV |
|---|---|
| Dose level | About 1.5 mg/kg radiolabeled compound + 190 mg/kg of intralipid |
| Radioactive dose | 155 µCi/kg |
| Dose volume | 1 mL/kg |
| Dose concentration | 190 mg/mL @ 5:95 ethanolic [$^{14}$C]-LPC-EPA:intralipid (20%) v/v |
| Dose vehicle | 5:95 v/v ethanol:injectable intralipid (20% emulsion) |
| Formulation specific radioactivity | 3 mCi/g |
| Dose formulation radioactive concentration: | 1.4773 mg/mL |

The [$^{14}$C]-LPC-EPA was mixed with the intralipid formulation to yield a dose formulation containing phospholipids at a final concentration of 190 mg/kg and the [$^{14}$C]-LPC-EPA at a concentration of about 1.5 mg/kg (155 µCi/kg) as follows:

0.394 mL of ethanolic [$^{14}$C]-LPC-EPA (2361 µCi/mL) was dispensed into a 20 mL glass vial and reduced to a final volume of approximately 0.30 mL under a flow of nitrogen at ambient temperature. 5.70 mL of 20% intralipid was added to the concentrated ethanolic [$^{14}$C]-LPC-EPA solution and gently vortex mixed to ensure homogeneity.

Oral Dose Formulations of [$^{14}$C]-LPC-EPA and [$^{14}$C]-LPC-DHA

Oral dose formulations of [$^{14}$C]-LPC-EPA and [$^{14}$C]-LPC-DHA were prepared by spiking ethanolic solutions of each radiolabeled compound into a modified krill oil LPC-formulations at a concentration ratio of 10:90 v/v radiolabeled ethanol:modified krill oil.

Each formulation that was later administered orally was prepared according to the following target specifications:

| Dose regimen and route | Single oral |
|---|---|
| Dose level | About 1.7 mg/kg radiolabeled material + 855 mg/kg of modified krill oil (LS-ABM_9C0) |
| Dose formulation radioactive concentration | [$^{14}$C]-LPC-EPA:1,6759 mg/kg<br>[$^{14}$C]-LPC-DHA:1,6914 mg/kg |
| Radioactive dose | 155 µCi/kg |
| Dose volume | 1 mL/kg |
| Dose concentration | 855 mg/g @ 10:90 ethanolic [$^{14}$C]-LPC-EPA:modified krill oil v/v |

The [$^{14}$C]-LPC-EPA was mixed with the phospholipid formulation to yield a dose formulation containing phospholipids at a final concentration of 855 mg/mL and the [$^{14}$C]-LPC-EPA at a final concentration of ca. 1.5 mg/kg (155 µCi/kg) as follows:

The final overall concentrations of ethanol in the formulation were approximately 10%.

0.328 mL of ethanolic [$^{14}$C]-LPC-EPA (2361 µCi/mL) was dispensed into a 20 mL glass vial. 0.172 mL of ethanol was added (to make up to 10% in volume). 4.5 mL of the modified krill oil LPC-formulation (at a temperature of 37° C.) was added to the concentrated ethanolic [$^{14}$C]-LPC-EPA solution and mixed by vortex mixer and vigorous pipetting to ensure homogeneity.

The [$^{14}$C]-LPC-DHA formulation was spiked into the phospholipid formulation, as described for [$^{14}$C]-LPC-EPA above.

Example 2: Uptake of LPC in Ocular Tissue—Oral and Intravenous Administration 32 male Sprague Dawley rats, in the weight range of 213-289 g and approximately 7-8 weeks old at the time of dose administration were housed in polypropylene cages and remained therein except for a short period during dosing. The room in which the animals were located was thermostatically monitored and data recorded continually (generally the temperature range was 21±2° C.; humidity range 55±10%) and exposed to 12 hours fluorescent lighting and 12 hours dark per day. Animals were equilibrated under standard animal house conditions for a minimum of 3 days prior to use. The health status of the animals was monitored throughout this period and the suitability of each animal for experimental use was confirmed before use.

A pellet diet (RM1 (E) SQC, Special Diets Services, Witham, Essex, UK) and water (from the domestic water supply) was available ad libitum throughout the holding, acclimatization and post-dose periods.

16 rats received a single intravenous administration of either formulation A or formulation B (eight per formulation) according to the dosage specification specified in example 1. Each rat was weighed prior to dose administration and the individual doses administered were calculated based on the bodyweight and the specified dose volume.

The 16 rats selected for oral administration were fasted overnight, and the dose was administered 1 hour after reintroduction of diet. Dose utensils for oral administration consisted of a syringe and gavage tube. During dose administration, the gavage was fed down the oesophagus to enable the formulation to be dispensed directly into the stomach.

Dose utensils for intravenous administration consisted of a hypodermic syringe and needle. The dose was administered directly into a tail vein as a slow bolus over 30 seconds.

After administration of the formulations to the male rats, a single rat was euthanized by overdose of carbon dioxide gas at each of the following times: 0.5, 3, 8, 24, 72, 96, 168 and 336 hours post-dose.

Each carcass was snap frozen in a hexane/solid carbon dioxide mixture immediately after collection and were then stored at approximately −20° C., pending analysis by QWBA (Quantitative whole body autoradiography).

The frozen carcasses were subjected to QWBA using procedures based on the work of Ullberg (Acta. Radiol. Suppl 118, 22 31, 1954). Sections were presented at up to five different levels of the rat body to include between 30 and 40 tissues (subject to presence of sufficient radioactivity) of which the uptake in brain, blood, kidney and spleen are disclosed herein.

The freeze-dried whole-body autoradiography sections were exposed to phosphor-storage imaging plates and incubated at ambient temperature in the dark for a minimum of five days.

A series of calibrated auto radiographic [$^{14}$C] microscales containing known amounts of radioactivity (nCi/g, produced by Perkin Elmer) were exposed alongside the animal sections on each plate.

Distribution of radioactivity was determined in ocular samples and microscales and quantified using a Fuji FLA-5100 fluorescent image analysing system and associated Tina (version 2.09) and SeeScan (version 2.0) software.

A representative background radioactivity measurement was taken for each exposure plate used. The limit of accurate quantification was considered to be the lowest [14C] microscale visible. A standard curve was produced from the microscales using Seescan and from which tissue concentrations of radioactivity were determined (nCi/g). For calculation of the weight equivalent/g data, the nCi/g data was divided by the relevant specific activity (nCi/m).

Table 1a shows total amounts of radioactivity in ocular tissue following a single intravenous administration averaging 1.5510 mg/kg [14]-LPC-DHA to male albino rats.

Table 1b presents the same data as in 1a but in molar concentrations and standardized to a dose of 2.80 micro mol/kg (1.5949 mg/kg)

Table 2a shows the total amounts of radioactivity in ocular following a single intravenous administration averaging 1.4968 mg/kg [14C]-LPC-EPA to male albino rats.

Table 2b presents the same data as in 2a but in molar concentrations and standardized to a dose of 2.80 micro mol/kg (1.5218 mg/kg)

Table 3a shows total amounts of radioactivity in ocular following a single oral dose averaging 1.6914 mg/kg [14]-LPC-DHA to male albino rats.

Table 3b presents the same data as in 3a but in molar concentrations and standardized to a dose of 2.80 micro mol/kg (1.5949 mg/kg)

Table 4a shows total amounts of radioactivity in ocular following a single oral dose averaging 1.6759 mg/kg [$^{14}$C]-LPC-EPA to male albino rats.

Table 4b presents the same data as in 4a but in molar concentrations and standardized to a dose of 2.80 micro mol/kg (1.5218 mg/kg)

The results are also presented in FIG. 8-10.

TABLE 1a

Concentration of radioactivity in ocular tissue (expressed as μg DHA equivalents/g) following a single intravenous administration averaging 1.5510 mg/kg [$^{14}$C]-LPC-DHA to male albino rats.

| Tissue type | Tissue | Animal no:<br>Time-point: | 48M<br>0.5 h | 49M<br>3 h | 50M<br>8 h | 51M<br>24 h | 52M<br>72 h | 45M<br>96 h | 46M<br>168 h | 47M<br>336 h |
|---|---|---|---|---|---|---|---|---|---|---|
| Ocular | Eye: Lens | | BLQ | BLQ | BLQ | 0.031 | 0.031 | 0.045 | 0.019 | 0.019 |
| | Eye: Whole | | 0.649 | 0.274 | 0.451 | 0.426 | 0.072 | 0.127 | 0.033 | 0.075 |

†Above limit of accurate quantification (>5.31 μg equivalents/g)
BLQ Below limit of accurate quantification (<0.004 μg equivalents/g)
NS No sample-tissue not sectioned

TABLE 1b

Data as presented in table 1a but expressed as nano mol equivalents/kg and normalized to a standard dose of 2.80 micro mol (1.5949 mg) LPC-DHA/kg

| Tissue type | Tissue | Animal no:<br>Time-point: | 48M<br>0.5 h | 49M<br>3 h | 50M<br>8 h | 51M<br>24 h | 52M<br>72 h | 45M<br>96 h | 46M<br>168 h | 47M<br>336 h |
|---|---|---|---|---|---|---|---|---|---|---|
| Ocular | Eye: Lens | | BLQ | BLQ | BLQ | 56.0 | 56.0 | 81.2 | 34.3 | 34.3 |
| | Eye: Whole | | 1171.6 | 494.6 | 814.2 | 769.1 | 130.0 | 229.3 | 59.6 | 135.4 |

†Above limit of accurate quantification (>5.31 μg equivalents/g)
BLQ Below limit of accurate quantification (<0.004 μg equivalents/g)
NS No sample-tissue not sectioned

TABLE 2a

Concentration of radioactivity in all ocular tissue (expressed as μg EPA equivalents/g) following a single intravenous administration averaging 1.4968 mg/kg [$^{14}$C]-LPC-EPA to male albino rats.

| Tissue type | Tissue | Animal no:<br>Time-point: | 32M<br>0.5 h | 33M<br>3 h | 34M<br>8 h | 35M<br>24 h | 36M<br>72 h | 29M<br>96 h | 30M<br>168 h | 31M<br>336 h |
|---|---|---|---|---|---|---|---|---|---|---|
| Ocular | Eye: Lens | | 0.038 | 0.034 | 0.033 | 0.033 | 0.036 | 0.014 | 0.017 | 0.047 |
| | Eye: Whole | | 0.353 | 0.116 | 0.112 | 0.057 | 0.076 | 0.070 | 0.030 | 0.059 |

†Above limit of accurate quantification (>4.96 μg equivalents/g)
BLQ Below limit of accurate quantification (<0.004 μg equivalents/g)
NS No sample-tissue not sectioned

TABLE 2b

Data as presented in table 1a but expressed as nano mol equivalents/kg and normalized to a sandard dose of 2.80 micro mol (1.5218 mg) LPC-EPA/kg

| Tissue type | Tissue | Animal no:<br>Time-point: | 32M<br>0.5 h | 33M<br>3 h | 34M<br>8 h | 35M<br>24 h | 36M<br>72 h | 29M<br>96 h | 30M<br>168 h | 31M<br>336 h |
|---|---|---|---|---|---|---|---|---|---|---|
| Ocular | Eye: Lens | | 71.1 | 63.6 | 61.7 | 61.7 | 67.3 | 26.2 | 31.8 | 87.9 |
| | Eye: Whole | | 660.4 | 217.0 | 209.5 | 106.6 | 142.2 | 131.0 | 56.1 | 110.4 |

†Above limit of accurate quantification (>4.96 μg equivalents/g)
BLQ Below limit of accurate quantification (<0.004 μg equivalents/g)
NS No sample-tissue not sectioned TABLE 3a Concentration of radioactivity in ocular tissue (expressed as μg DHA equivalents/g) following a single oral dose averaging 1.6914 mg/kg [$^{14}$C]-LPC-DHA to male albino rats.

| | | | LPC-EPA μg equivalents/g | | | | | | | |
|---|---|---|---|---|---|---|---|---|---|---|
| Tissue type | Tissue | Animal no: Time-point: | 40M 0.5 h | 41M 3 h | 42M 8 h | 43M 24 h | 44M 72 h | 37M 96 h | 38M 168 h | 39M 336 h |
| Ocular | Eye: Lens | | BLQ | 0.009 | BLQ | BLQ | 0.007 | 0.026 | 0.019 | 0.024 |
| | Eye: Whole | | BLQ | 0.020 | 0.007 | 0.015 | 0.028 | 0.103 | 0.068 | 0.051 |

†Above limit of accurate quantification (>6.11 μg equivalents/g)
BLQ Below limit of accurate quantification (<0.004 μg equivalents/g)
NS No sample-tissue not sectioned TABLE 3b Data as presented in table 1a but expressed as nano mol equivalents/kg and normalized to a standard dose of 2.80 micro mol (1.5949 mg) LPC-DHA/kg

| Tissue type | Tissue | Animal no: Time-point: | 40M 0.5 h | 41M 3 h | 42M 8 h | 43M 24 h | 44M 72 h | 37M 96 h | 38M 168 h | 39M 336 h |
|---|---|---|---|---|---|---|---|---|---|---|
| Ocular | Eye: Lens | | BLQ | 14.9 | 0.0 | 0.0 | 11.6 | 43.0 | 31.5 | 39.7 |
| | Eye: Whole | | BLQ | 33.1 | 11.6 | 24.8 | 46.4 | 170.5 | 112.6 | 84.4 |

†Above limit of accurate quantification (>6.11 μg equivalents/g)
BLQ Below limit of accurate quantification (<0.004 μg equivalents/g)
NS No sample-tissue not sectioned TABLE 4a Concentration of radioactivity in ocular tissue (expressed as μg EPA equivalents/g) following a single oral dose averaging 1.6759 mg/kg [$^{14}$C]-LPC-EPA to male albino rats.

| | | | LPC-EPA μg equivalents/g | | | | | | | |
|---|---|---|---|---|---|---|---|---|---|---|
| Tissue type | Tissue | Animal no: Time-point: | 24M 0.5 h | 25M 3 h | 26M 8 h | 27M 24 h | 28M 72 h | 21M 96 h | 22M 168 h | 23M 336 h |
| Ocular | Eye: Lens | | BLQ | 0.015 | 0.030 | 0.009 | 0.010 | 0.028 | 0.044 | 0.050 |
| | Eye: Whole | | BLQ | 0.023 | 0.028 | 0.021 | 0.033 | 0.051 | 0.043 | 0.036 |

†Above limit of accurate quantification (>5.70 μg equivalents/g)
BLQ Below limit of accurate quantification (<0.004 μg equivalents/g)
NS No sample-tissue not sectioned TABLE 4b Data as presented in table 1a but expressed as nano mol equivalents/kg and normalized to a standard dose of 2.80 micro mol (1.5218 mg) LPC-EPA/kg

| | | | LPC-EPA μg equivalents/g | | | | | | | |
|---|---|---|---|---|---|---|---|---|---|---|
| Tissue type | Tissue | Animal no: Time-point: | 24M 0.5 h | 25M 3 h | 26M 8 h | 27M 24 h | 28M 72 h | 21M 96 h | 22M 168 h | 23M 336 h |
| Ocular | Eye: Lens | | BLQ | 25.1 | 50.1 | 15.0 | 16.7 | 46.8 | 73.5 | 83.5 |
| | Eye: Whole | | BLQ | 38.4 | 46.8 | 35.1 | 55.1 | 85.2 | 71.8 | 60.1 |

†Above limit of accurate quantification (>5.70 μg equivalents/g)
BLQ Below limit of accurate quantification (<0.004 μg equivalents/g)
NS No sample-tissue not sectioned When administered extra-orally to avoid first exposure and degradation in the mouth and gut, DHA and surprisingly also EPA in its LPC form (as measured by their respective $^{14}$C radiolabelled carboxylic acid residues) exhibit very rapid and persistent uptake and massive accumulation into ocular tissue as illustrated in tables 1 to 4 and FIGS. 8 to 10.

For LPC-EPA given as a short intra vascular (i.v.) bolus the area under the concentration time curve (AUC) for the first 24 hours was demonstrated to be more than 5 times larger than the equivalent measure for the oral dose LPC (FIG. 9)

For LPC-DHA given as a short intra vascular (i.v.) bolus the area under the concentration time curve (AUC) for the first 24 hours was demonstrated to be more than 40 times higher than the equivalent measure for the oral dose LPC-DHA (FIG. 9).

Example 3: Effects of Composition Comprising a Combination of LPC EPA and LPC DHA This example provides data from three weeks daily dosing with different krill oil lysophospholipid compositions containing LPC-EPA and LPC-DHA. It was of interest to investigate whether krill oil lysophospholipid compositions cause an increase retina EPA and DHA content. The EPA, DHA and total omega-3 contents of these oils are given in Table 5 below. Krill oil lysophospholipid compositions of various purities and production of these have previously been described in detail (WO2019/123015).

TABLE 5

EPA, DHA and total omega-3 contents in test products.

| Batch A100588-20190924 | FA contents in oil (g/100 g) | | | Phospholipid-bound | |
|---|---|---|---|---|---|
| | EPA | DHA | Total Omega-3 | EPA | DHA |
| Olive oil | 0 | 0 | 0 | 0 | 0 |
| Boost | 17.3 | 10.0 | 35.2 | 11.1 | 6.3 |
| Crude (27% LPC) | 16.9 | 9.9 | 34.7 | 10.6 | 6.7 |
| Pure (89% LPC) | 23.7 | 11.7 | 44.0 | 23.2 | 11.3 |

Twenty-four male rats were divided into six groups and received daily oral gavage for 3 weeks, containing: Group 1) Olive oil (0 mg/kg/day EPA and 0 mg/kg/day DHA); Group 2) Crude (27% LPC), low dose (185 mg/kg/day EPA and 108 mg/kg/day DHA), 3) Crude (27% LPC), medium dose (370 mg/kg/day EPA and 217 mg/kg/day DHA), 4) Crude (27% LPC), high dose (926 mg/kg/day EPA and 543 mg/kg/day DHA), 5) Pure (89% LPC), medium dose (324 mg/kg/day EPA and 160 mg/kg/day DHA), 6) Superba Boost krill oil, medium dose (379 mg/kg/day EPA and 219 mg/kg/day DHA).

Following homogenization of tissue, retina FAs were extracted and analyzed by HPLC. As can be seen in FIGS. 1 and 2, there is a strong dose-response relationship, with higher doses of EPA being associated with higher retina EPA concentrations (FIG. 1) and increases in the EPA/ETA (20:4) ratio (FIG. 2). Surprisingly, FIG. 1 does not show a difference in retina EPA concentration between the "crude" and "pure" krill oil lysophospholipid compositions. However, rats fed with crude lysophospholipid compositions show a higher retina EPA/ETA ratio than rats fed with Superba Boost krill oil at similar doses. This implies that rats fed the LPC composition show a more favorable EPA profile in the retina as compared to rats fed Superba Boost krill oil and olive oil, and, furthermore, that higher doses of the lysophospholipid composition are associated with a more favorable EPA profile in the retina. Inspection of FIG. 3 suggests that improvement in retina EPA profile is likely related to higher amounts of LPC-EPA being present in plasma (and subsequent increased EPA uptake via mfsd2a), with the crude high dose showing both the highest levels of LPC-EPA in plasma as well as the highest retina EPA content and EPA/ETA ratio.

FIG. 4 shows a strong dose-response relationship, with higher doses of the lysophospholipid compositions being associated with a higher DHA/ETA ratio and a particularly pronounced increase in DHA/ETA ratio in the crude high dose group. This suggests that DHA is dose-dependently taken up into the retina from the lysophospholipid compositions irrespective in differences in lysophospholipid product purity. FIG. 5 further shows that the crude high dose group shows the highest levels of LPC-DHA at the end of the study period (T2), which supports the notion that DHA uptake across the blood-retina-barrier occurs via Mfsd2a.

Analysis of Fatty Acid Methyl Esters (FAME) by GC-FID was used to further assess brain EPA concentrations in relation to total fatty acids (FIG. 6) as well as the relationship between Arachidonic acid (ARA; 20:4 n-6), DHA dose and test product (FIG. 7). GC-fid further supported the HPLC data, with higher doses of the "crude" lysophospholipid composition being associated with higher retina EPA concentrations relative to total fatty acids (FIG. 6). Furthermore, FIG. 7 shows that higher doses of the "crude" DHA/EPA lysophospholipid composition was associated with lower levels of retina ARA concentration relative to total fatty acids, and the crude lysophospholipid composition showed a more pronounced ARA decrease as compared to Superba Boost at comparable doses. This again suggests that increasing doses of the lysophospholipid composition is associated with a more beneficial fatty acid profile in the retina.

Example 4: Use of Krill Lysophospholipid Composition to Deliver EPA and DHA to the Brain, Retina and the Liver Materials and Methods Krill oil and fish oil were generous gifts from Bioriginal Food & Science Corporation, Saskatoon, Canada. Antibody for BDNF was obtained from Abcam, Cambridge, Mass.). Standards of 17:0 LPC, 22:6 LPC were purchased from Avanti Polar Lipids (Alabaster, Ala.). Immobilized lipase from *Mucor meihei* was purchased from Creative enzyme (Shirley, N.Y.). Krill oil and fish oil were treated with lipase as follows: The oil (15 g) was dissolved in 300 mL of 95% ethanol in water (v/v) and 20 g of immobilized lipase was added. The reaction mixture was shaken in an orbital incubator at 175 rpm at 40° C. in the dark for 72 h, under nitrogen. The ethanol was evaporated under vacuum, and the samples were analyzed for the lipid and fatty acid composition by TLC and GC/MS. Samples of control and lipase-treated krill oil were analyzed by TLC with the solvent system of chloroform:methanol: water (65: 25: 4 by vol). Spots corresponding to LPC, PC, and PE were scraped and analyzed for the fatty acid composition by GC/MS. The control and lipase-treated fish oil sample was separated on TLC plates with the solvent system of hexane: diethyl ether: acetic acid (90:10:1 by vol) and the spots corresponding to MAG, DAG, free fatty acid, and TAG were analyzed by GC/MS.

Diets and treatment. The treated and untreated krill oil and fish oil containing comparable amounts of total EPA and DHA (~1.2 μmol/g diet) were mixed with corn oil to make up to 7% total fat in the diet, blended with AIN93G rodent diet and pelleted and vacuum sealed by Diets Inc. The control diet contained only corn oil The diets were stored at −20° C., and were thawed weekly before use. The fatty acid composition of the dietary oils (including the mixed corn oil) is shown in Table 6. As expected, the lipase treatment resulted in the generation of EPA- and DHA-rich LPC. The percentage of EPA+DHA in LPC of untreated krill oil was 18%, whereas it was >80% in the lipase-treated krill oil. Table 7 shows the distribution of omega 3 fatty acids (EPA+DHA) among the major lipid fractions of the dietary oils. PC contained the largest percentage of total EPA+DHA in the untreated krill oil, whereas LPC contained the largest percentage in the lipase-treated krill oil. Lipase treatment of fish oil resulted in the shifting of EPA and DHA to free fatty acids and MAG from TAG.

All experiments were conducted with ethical approval from UIC Institutional Animal Care and Use Committee protocols. Male C57BL/6 mice (age, 2 months) were purchased from Jackson Laboratories (Bar Harbor, Me.). Mice were randomly divided into 5 groups of 5 animals each and were fed the diets ad lib for 30 days. Body weights were measured weekly. After the 30-day period, the mice were anesthetized with ketamine (90 mg/ml) and xylazine (10 mg/ml). Blood was drawn by cardiac puncture using heparinized syringes, and plasma prepared by centrifugation at 1500×g for 15 min. The mice were then perfused transcardially with ice-cold 100 mM PBS (pH 7.4), and liver, heart, brain, and adipose tissues were harvested. The brain was further dissected to separate pre-frontal cortex, hippocampus, striatum, and cerebellum. All samples were flash-frozen in liquid nitrogen and stored at 80° C. until analysis.

Statistics Statistical analyses were performed using GraphPad Prism 8.0 software (La Jolla, Calif.). Significance between treatments was determined by one-way ANOVA with post hoc Tukey multiple comparison test.

Lipid extraction and fatty acid analysis Plasma samples for LC/MS analysis of LPC species and isomers were extracted essentially as described by Ivanova et al (27). Plasma samples (100 μl) were deproteinized with 900 μl acidified methanol (0.01 N HCl, pH 4.0) after adding the internal standard of 17:0 LPC (10 μg). The sample was sonicated for 3 min in Branson sonifier and centrifuged at 21,500×g for 10 min at 4° C. the supernatant was collected, and 10 μl injected into HPLC system. The analysis of LPC isomers was carried out as described earlier (28), using Atlantis (Waters Corp., Milford, Mass.) HILIC column, and by multiple reaction monitoring in positive mode electrospray mass spectrometry. Quantification of LPC species was performed with the internal standard of 17:0, and a correction factor of (x 0.233) was applied to account for the differences in ion intensity of 17:0 LPC and 22:6 LPC species, which was determined separately with known standards. Our previous studies did not include this correction factor, and therefore the plasma values for omega 3 LPC species reported previously (16, 17, 29) were about 4-fold higher than reported here.

For the fatty acid analysis, the lipids were extracted by the Bligh and Dyer procedure (30), fatty acid methyl esters were prepared with methanolic HCl, and analyzed by GC/MS as described previously (16).

Western blot analysis The BDNF levels in brain fractions were determined by Western blot analysis. Briefly, the tissue was homogenized in lysis buffer (50 mM Tris, pH 8.0, 25 mM KCl, 0.5 mM EDTA, Nonidet P-40, 0.1 mM EGTA, 10 μL/mL aprotinin, 1 mM $MgCl_2$, 1 mM $CaCl_2$), 1 mM $Na_4P_2O_7$, 1 mM $Na_4MO_4$, 1% protease inhibitor cocktail, 1 mM phenyl sulfonyl fluoride, 10 mM NaF, 1 mM NaV) and the suspension was left on ice for 30 min and centrifuged at 13000×g at 4° C. for 10 min. The supernatant (20 μg protein) was subjected to electrophoresis on 10% SDS gel at 80 V for 2 h. The separated proteins were transferred to methanol-rinsed polyvinylidene difluoride membranes (Millipore, Burlington, Mass.) and the membranes were blocked with 5% (w/v) non-fat dried milk in Tris buffered saline containing 0.1% tween-20 (TBST) for 1 h at 4° C. The membranes were probed with primary antibody (BDNF, EPR1292, Abcam, Cambridge, Mass.) in TBST overnight at 4° C. The membranes were washed with TBST by 3 times and incubated with horseradish peroxidase conjugated anti-rabbit IgG (Cell Signaling Technologies, Danvers, Mass.) at room temperature for 1h. Finally, the membranes were washed with TBST 3 times and developed with enhanced chemiluminescent (ECL) detection kits (Bio-Rad, Hercules, Calif.) for 1 min, the respective proteins were quantified by Bio-Rad ChemiDoc MP Imaging System, and the results were expressed as ratios of BDNF/β-actin.

Results

There were no significant differences in the food intake or body weights of mice treated with different diets (results not shown).

Figure 12:
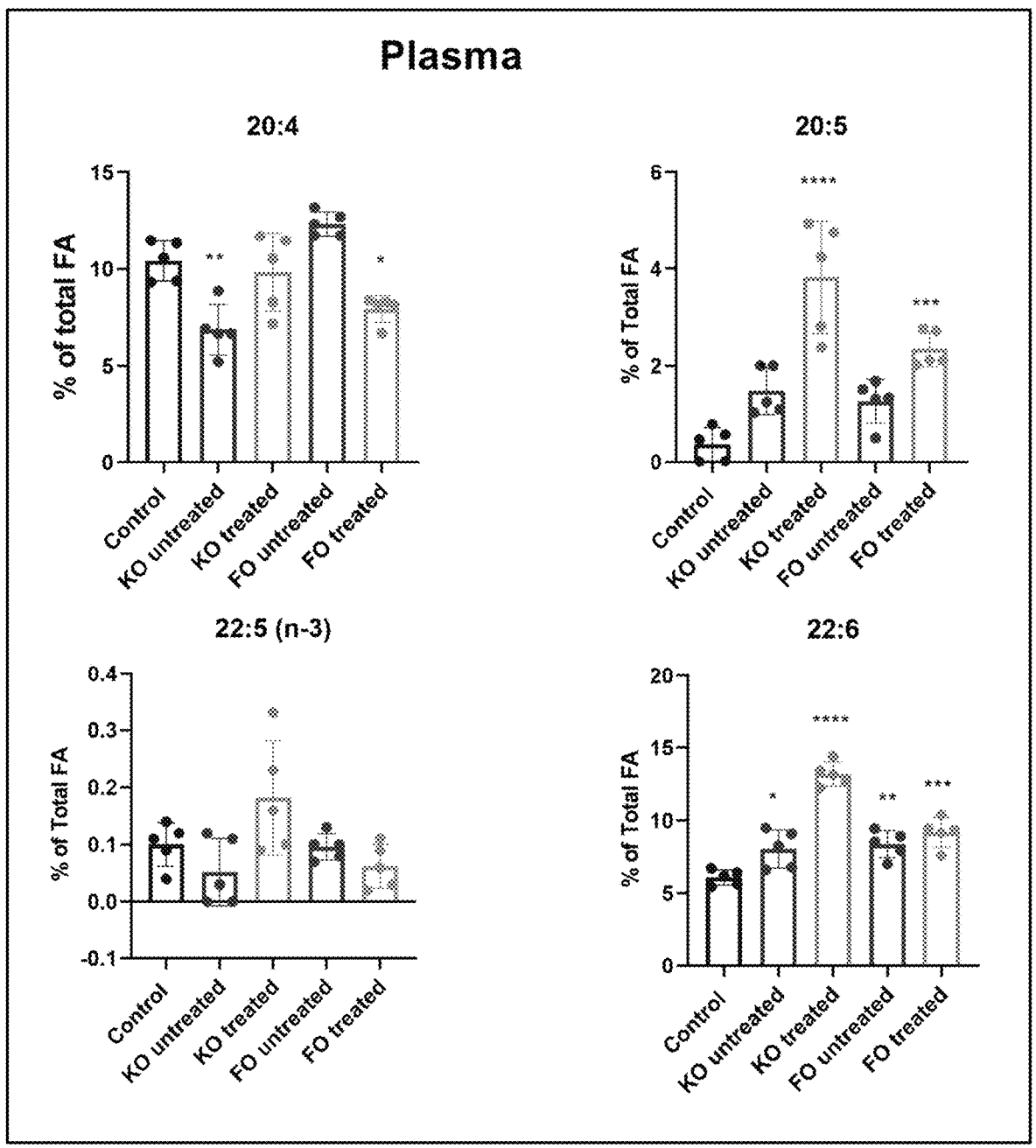
FIG. 12 shows the effect of dietary treatments on plasma levels of long chain PUFA. Total lipids of fasting plasma were extracted, transmethylated and analyzed for the fatty acid composition by GC/MS, as described in the text. The values shown are mean±SD of 5 animals for each group. Statistical significance was determined by one-way ANOVA, with post-hoc Tukey multiple comparison correction (Graphpad 8.0 software). *$p<0.05$; $p<0.01$; *$p<0.001$; ****$p<0.0001$ compared to control group.

Plasma The percentage composition of ARA (20:4), EPA (20:5), DPA (22:5) and DHA (22:6) are shown in FIG. 12. Although there was only a modest increase in EPA and DHA with untreated fish oil and krill oil, the lipase treatment of fish oil, as well as krill oil, resulted in higher accumulation of EPA and DHA in the plasma. Lipase treatment increased the efficacy of krill oil more than that of fish oil with respect to the increases in plasma EPA and DHA (9-fold increase in EPA and 3-fold increase in DHA in the case of krill oil, versus 2.2-fold increase in EPA and 70% increase in DHA in the case of fish oil). These results suggest that lipase treatment increases the overall absorption of krill oil more than that of fish oil. The arachidonate content was decreased significantly only in the mice fed untreated krill oil, or lipase-treated fish oil.

Figure 13:
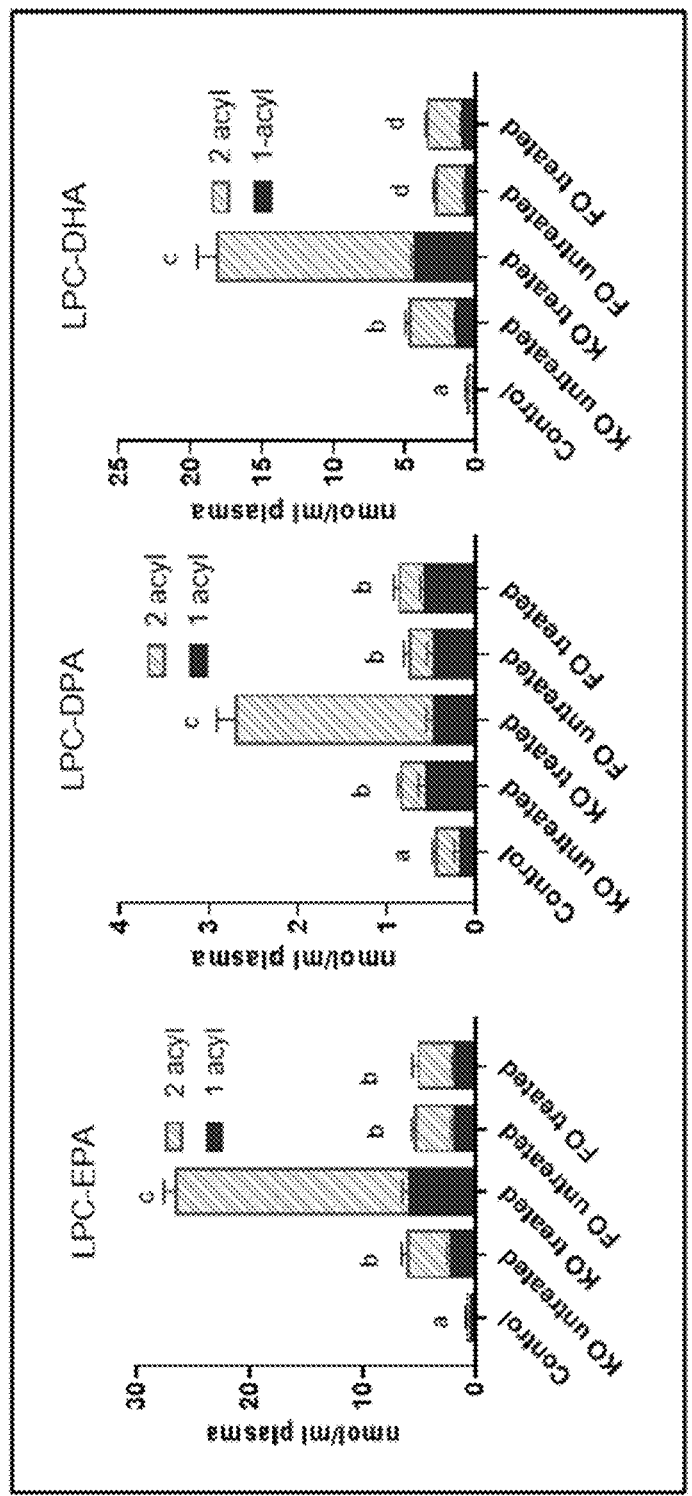
FIG. 13 shows the effect of feeding native and lipase-treated krill oil and fish oil on the plasma LPC species. Plasma samples were extracted with acidified methanol and analyzed by LC/MS using HILIC column, for the concentration, as well as the isomer composition of the omega 3 LPC species as described in the text. The LPC concentrations were determined using 17:0 LPC as the internal standard. A correction factor (x 0.233) was applied to calculate the values, since the intensity values of the standards of 17:0-LPC and 22:6 LPC differed by this amount under the conditions used. Bars with non-identical superscripts are significantly different from each other, as determined by one-way ANOVA with Tukey multiple comparison correction (total LPC).

The concentration and isomer composition of LPC species containing EPA, DPA, and DHA were measured by LC/MS (FIG. 13). Although the three LPC's were increased by all diets, the increase after feeding lipase-treated krill oil was 4-5 fold greater than the other diets. Furthermore, most of the increase was due to the sn-2 acyl isomer in all cases. Although the lipase-treated krill oil contained the sn-2 acyl LPC isomers, the LPC found in the plasma may not be all due to the recently absorbed LPC because plasma sn-2 acyl LPC was also increased slightly after feeding fish oil which did not contain any LPC. Furthermore, the ratio of LPC-DHA/LPC-EPA is much higher in the plasma, compared to that in the diets, suggesting some conversion of EPA to DHA occurred, perhaps in the liver. Whereas the lipase treatment of krill oil resulted in a 4-fold increase in plasma levels of omega-3 LPC's compared to the untreated krill oil, there was no increase by lipase treatment of the fish oil.

Figure 14:
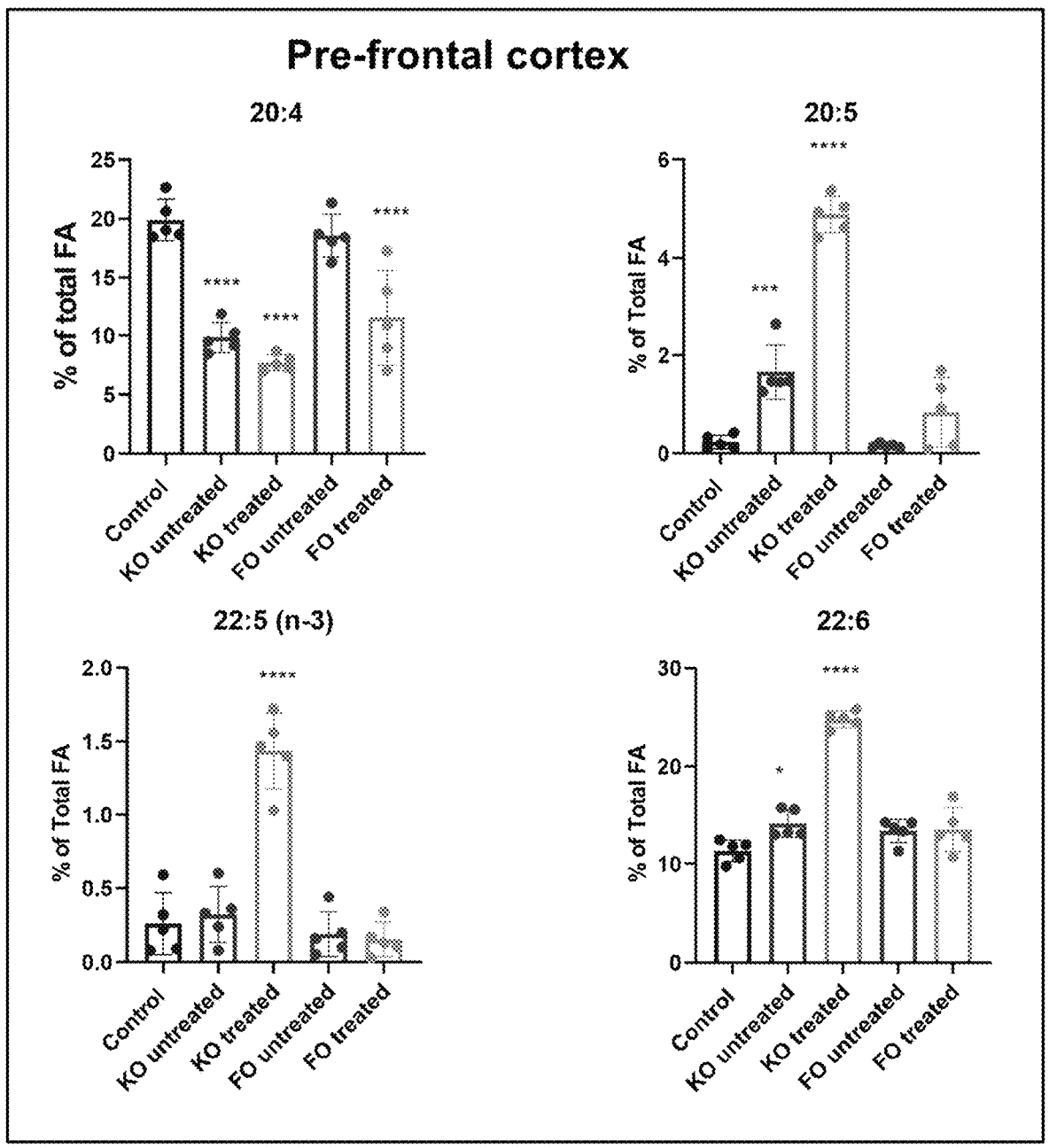
FIG. 14 shows the PUFA composition of pre-frontal cortex. The total fatty acid composition was analyzed by GC/MS, and the percentage composition of only 20:4 (ARA), 20:5 (EPA), 22:5 (DPA), and 22:6 (DHA) are shown. The values shown are mean±SD of 5 animals for each group. Statistical significance was determined by one-way ANOVA, and the symbols are the same as under FIG. 12.

PUFA in Brain regions Four separate regions of the brain were analyzed for the fatty acid composition. In pre-frontal cortex (FIG. 14), the EPA content was significantly increased by untreated krill oil (from 0.23% to 1.66% of total FA). However, lipase-treatment of krill oil resulted in a further 3-fold increase in cortex EPA, compared to the untreated krill oil. In contrast, fish oil had no effect on EPA content either with or without treatment with lipase. The DHA content of the cortex was increased by 25% after feeding untreated krill oil, but lipase treatment of krill oil resulted in an increase of 118%, showing a 4.7-fold stimulation by the lipase treatment. Fish oil had no effect on DHA content of cortex either before or after lipase treatment. DPA (22:5) was increased 4.5-fold by the lipase-treated krill oil, but not by any other preparation. There was a significant decrease in ARA (20:4) content of cortex by both the preparations of krill oil, as well as by the lipase-treated fish oil, but not by untreated fish oil. The decrease in ARA is apparently because of its replacement by EPA or DHA, although in the case of lipase-treated fish oil there was no net increase in the omega 3 fatty acids.

In the hippocampus (FIG. 15), the EPA content was significantly increased only by lipase-treated krill oil (12.5-fold increase compared to control). The DHA content was increased 15% by untreated krill oil, whereas lipase treatment resulted in an increase of 46% (3-fold stimulation by lipase treatment). The ARA content was decreased significantly by all the preparations, although untreated fish oil showed less decrease than other preparations. There were no changes in DPA by any of the diets.

Figure 16:
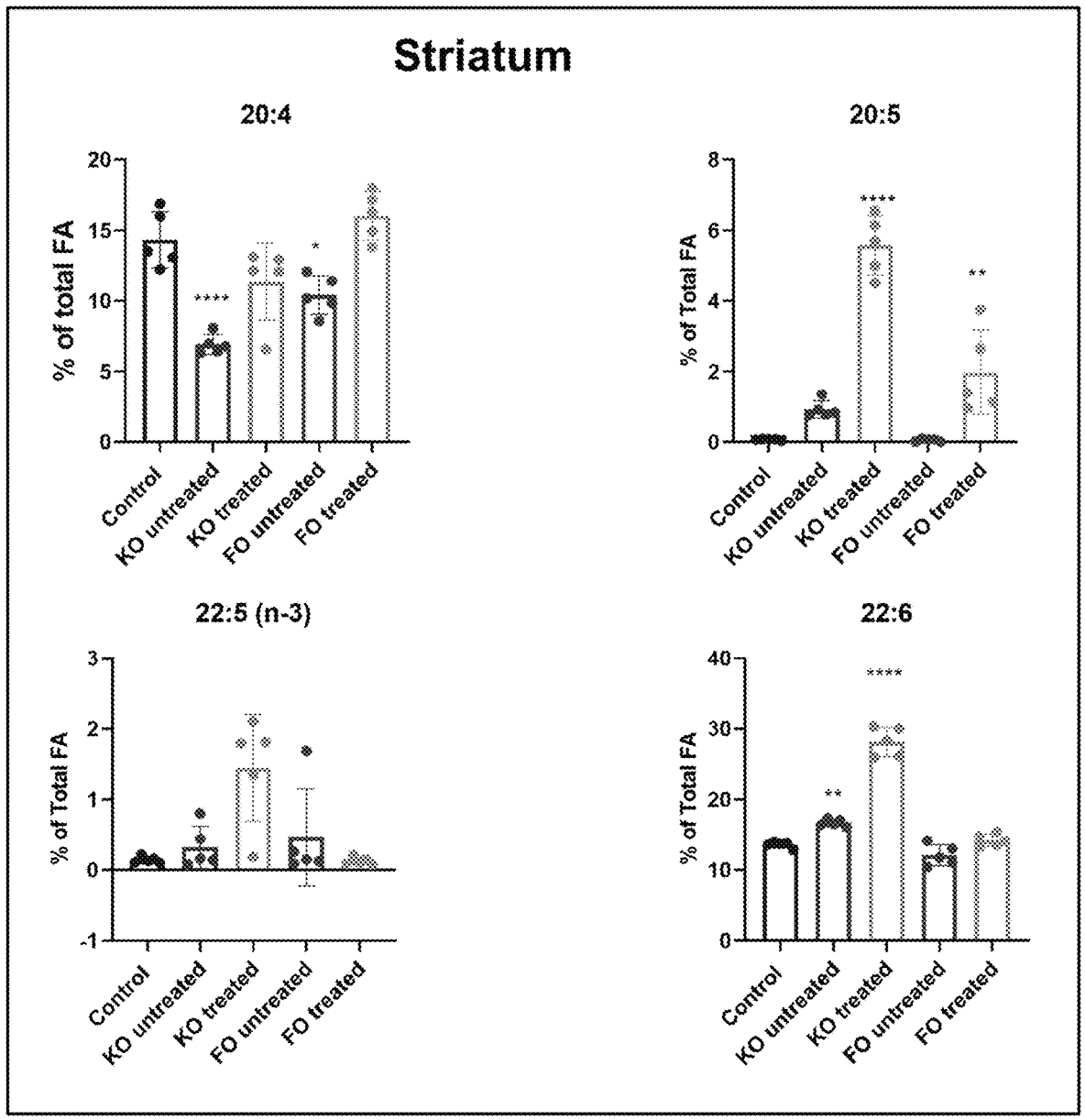
FIG. 16 shows the PUFA composition of striatum. The PUFA composition was analyzed as described in the text. The values shown are mean±SD of 5 mice in each group. Statistical significance between control and experimental diets was determined by one-way ANOVA, with post-hoc Tukey multiple comparison test. The symbols for significance are the same as under FIG. 12.

In the striatum (FIG. 16), the EPA content was increased by lipase-treated krill oil (70-fold), but not by untreated krill oil. Interestingly, the lipase-treated fish oil also increased the EPA content (12-fold), although untreated fish oil had no effect. The DHA content was increased 23% by untreated krill oil, and by 107% by lipase treated krill oil (4.7-fold stimulation by lipase treatment). There was no effect by either untreated or treated fish oil on the DHA content of striatum. DPA percentage was increased significantly only by the lipase-treated krill oil (from 0.14% to 1.45%). The ARA content was decreased significantly only by untreated krill (−51%) oil and untreated fish oil (−27%).

Figure 17:
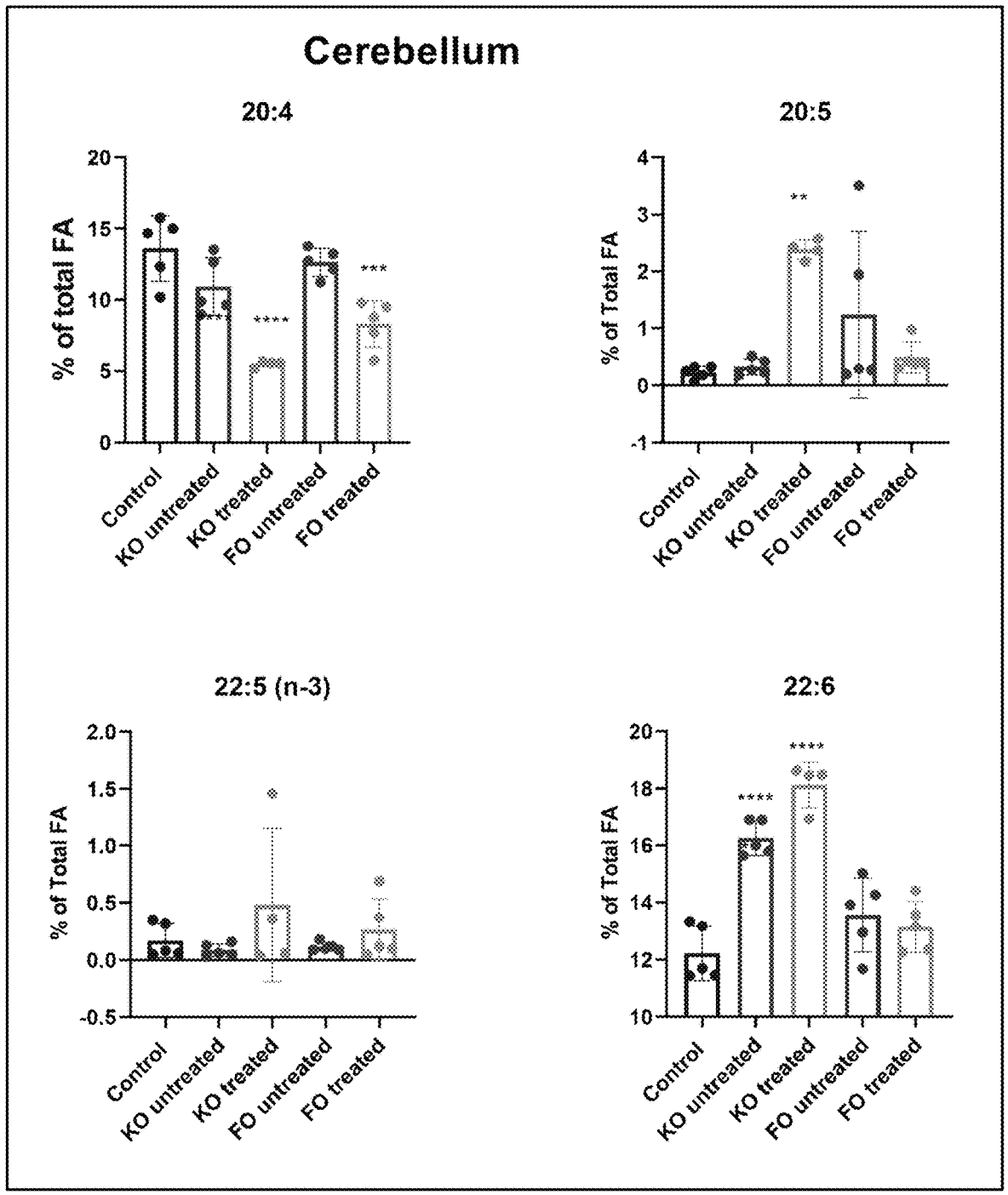
FIG. 17 shows the PUA composition in cerebellum. The fatty acid composition was analyzed by GC/MS as described in the text. The values shown are mean±SD of 6 mice in each group. Statistical significance between control and experimental diets was determined by one-way ANOVA, with post-hoc Tukey multiple comparison test. The symbols for significance are the same as under FIG. 12.

In the cerebellum, only the lipase-treated krill oil significantly increased the EPA content (11-fold) (FIG. 17). The DHA content was increased by both untreated and lipase-treated krill oils, but the increase was greater after lipase treatment (12% stimulation by lipase treatment). Fish oil had no significant effect, whether lipase-treated or not. Significant decrease in ARA content occurred with lipase-treated krill oil. The ARA was also decreased by lipase-treated fish oil, although there was no significant increase in the omega 3 fatty acids.

These results show that in all brain regions, the accretion of EPA and DHA was increased up to several fold by the partial lipolysis of krill oil, whereas the effect of fish oil was minimal even after lipase treatment. These results support the conclusion that the generation of LPC-EPA and LPC-DHA is essential for the accretion of omega 3 fatty acids by the brain. Although the amount of LPC-EPA was higher than that of LPC-DHA in the plasma, the increase in brain DHA was greater than that of EPA, suggesting that EPA is converted to DHA in the brain or was converted to LPC-DHA before entering the brain.

Figure 18:
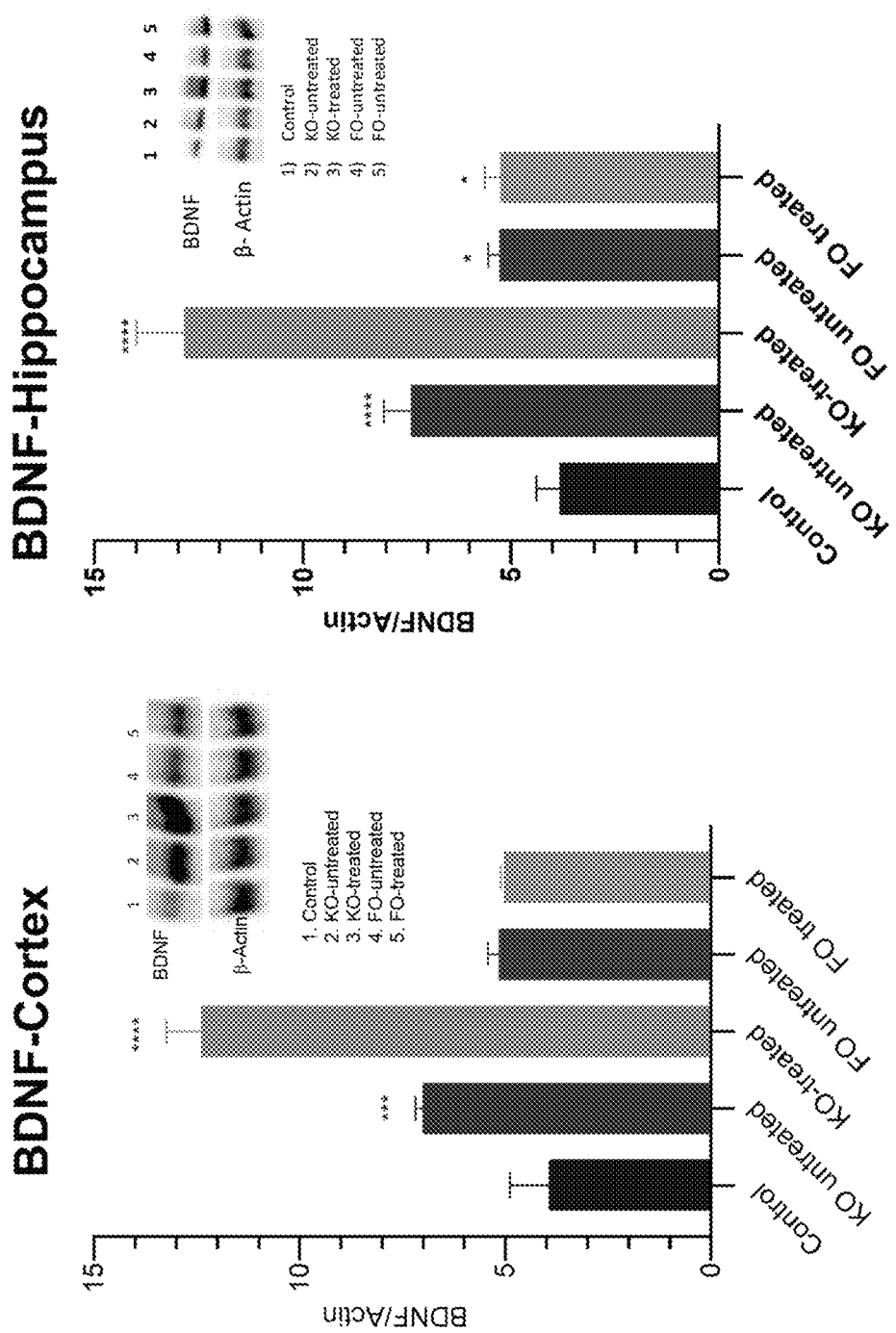
FIG. 18 shows the effect of dietary treatments on BDNF levels in pre-frontal cortex and hippocampus. Immunoassay of BDNF levels was carried out as described in the text with β-actin as the internal standard. The BDNF/β-actin ratios shown are mean±SD of 3 mice for each group. The insets show representative immunoblots. The statistical significance between the control and the experimental diets was determined by one-way ANOVA, with post-hoc Tukey multiple comparison test. * $p<0.001$ vs control; ** $p<0.0001$ vs control.

BDNF in the brain: Our previous studies showed that increasing brain DHA or EPA by LPC-DHA and LPC-EPA results in an increase in brain BDNF (16, 26), the neurotrophin essential for neuronal survival and cognitive function. In order to determine whether similar changes occurred after feeding krill oil and fish oil, we determined the levels of BDNF in pre-frontal cortex and hippocampus by Western blot. As shown in FIG. 18, the BDNF levels of both brain regions were significantly increased by both untreated and treated krill oil, but the increase in the case of lipase-treated krill oil was 3-fold greater than with untreated krill oil. There was a small but significant increase of BDNF in hippocampus, but not in cortex, by the fish oil diet, but the lipase treatment did not show further increase.

Figure 19:
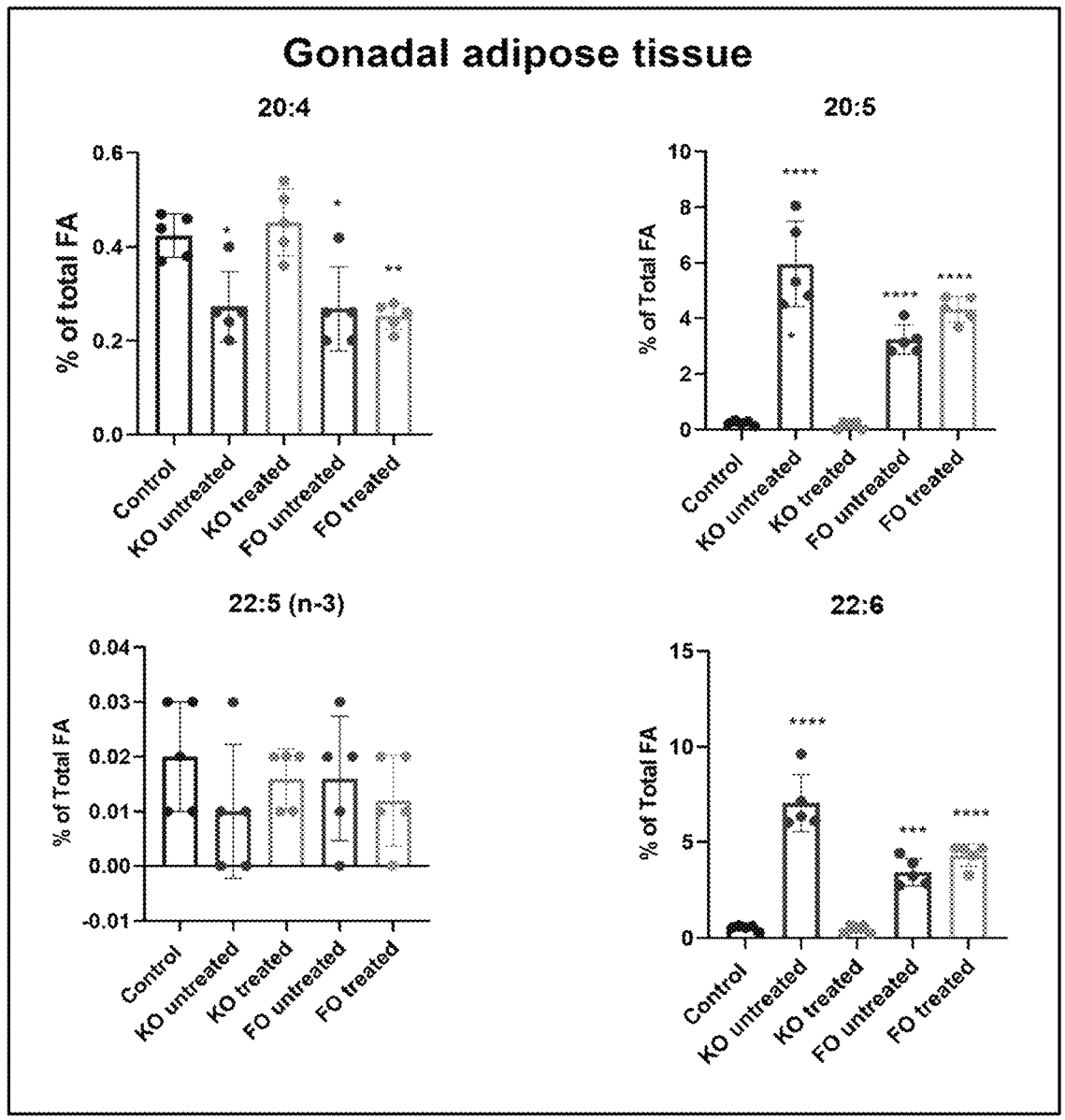
FIG. 19 shows the PUFA composition of peri-gonadal adipose tissue. The percentage values shown are mean±SD of 5 mice for each group. The statistical significance values (one-way ANOVA) are between control and the experimental diets, and the symbols are the same as under FIG. 12.
Figure 20:
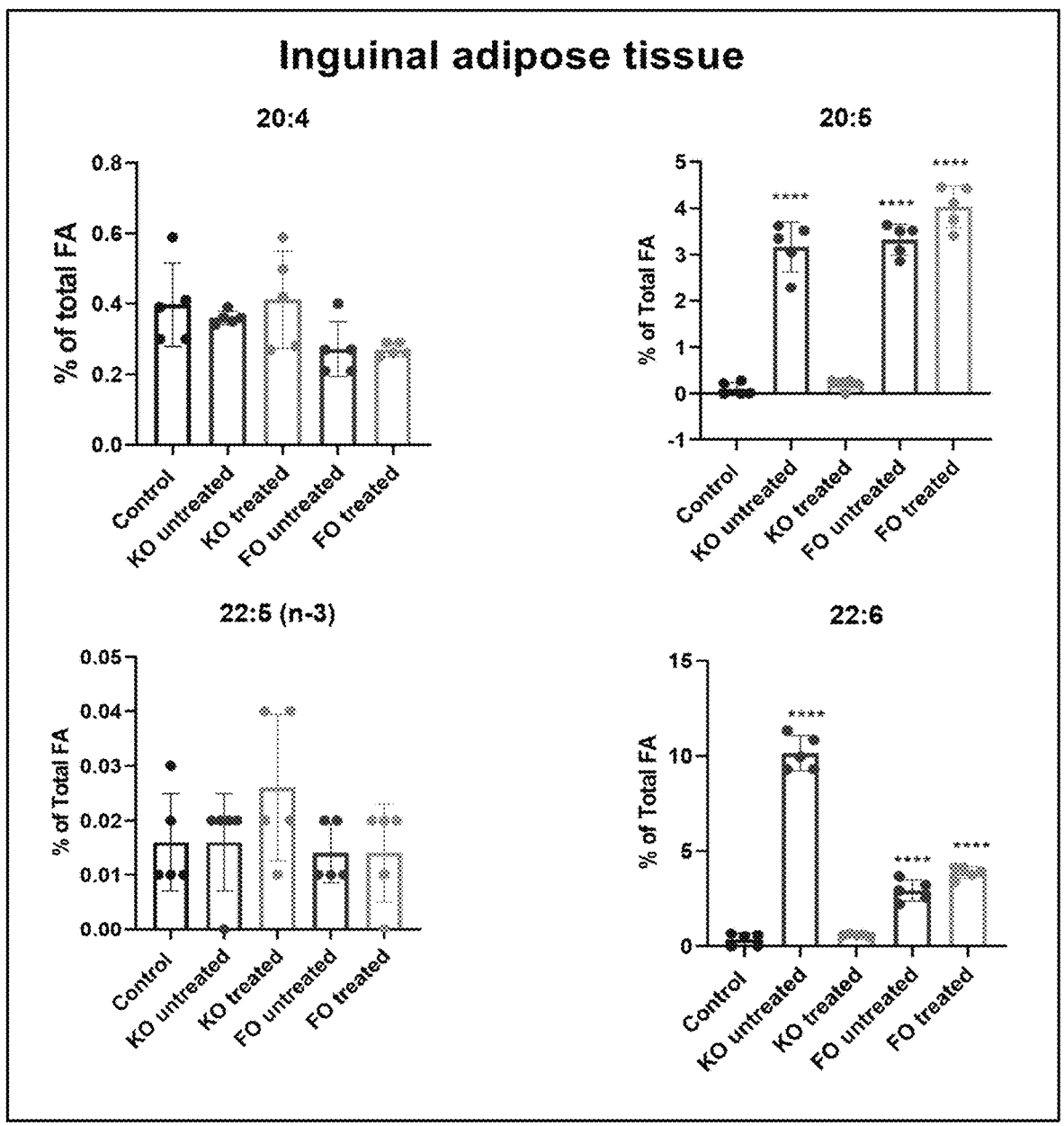
FIG. 20 shows the PUFA composition of inguinal adipose tissue. The percentage values shown are mean±SD of 5 mice for each group. The statistical significance values (one-way ANOVA) are between control and the experimental diets, and the symbols are the same as under FIG. 12.

Adipose tissue In contrast to the brain regions, lipase-treated krill oil had no effect on the EPA or DHA content of the either peri-gonadal (FIG. 19) or inguinal adipose tissue (FIG. 20). However, the untreated and treated fish oil, as well as the untreated krill oil, all increased the EPA and DHA content of both types of adipose tissue. There was no effect on the ARA levels of inguinal adipose tissue by any of the preparations. Here the increase in the omega 3 fatty acids occurred at the expense of 18:1 and 18:2 (not shown), rather than replacing ARA, as occurred in the brain regions. In the peri-gonadal adipose tissue, however, all preparations except the lipase-treated krill oil decreased the ARA content, corresponding to the increase in omega 3 fatty acids.

Figure 21:
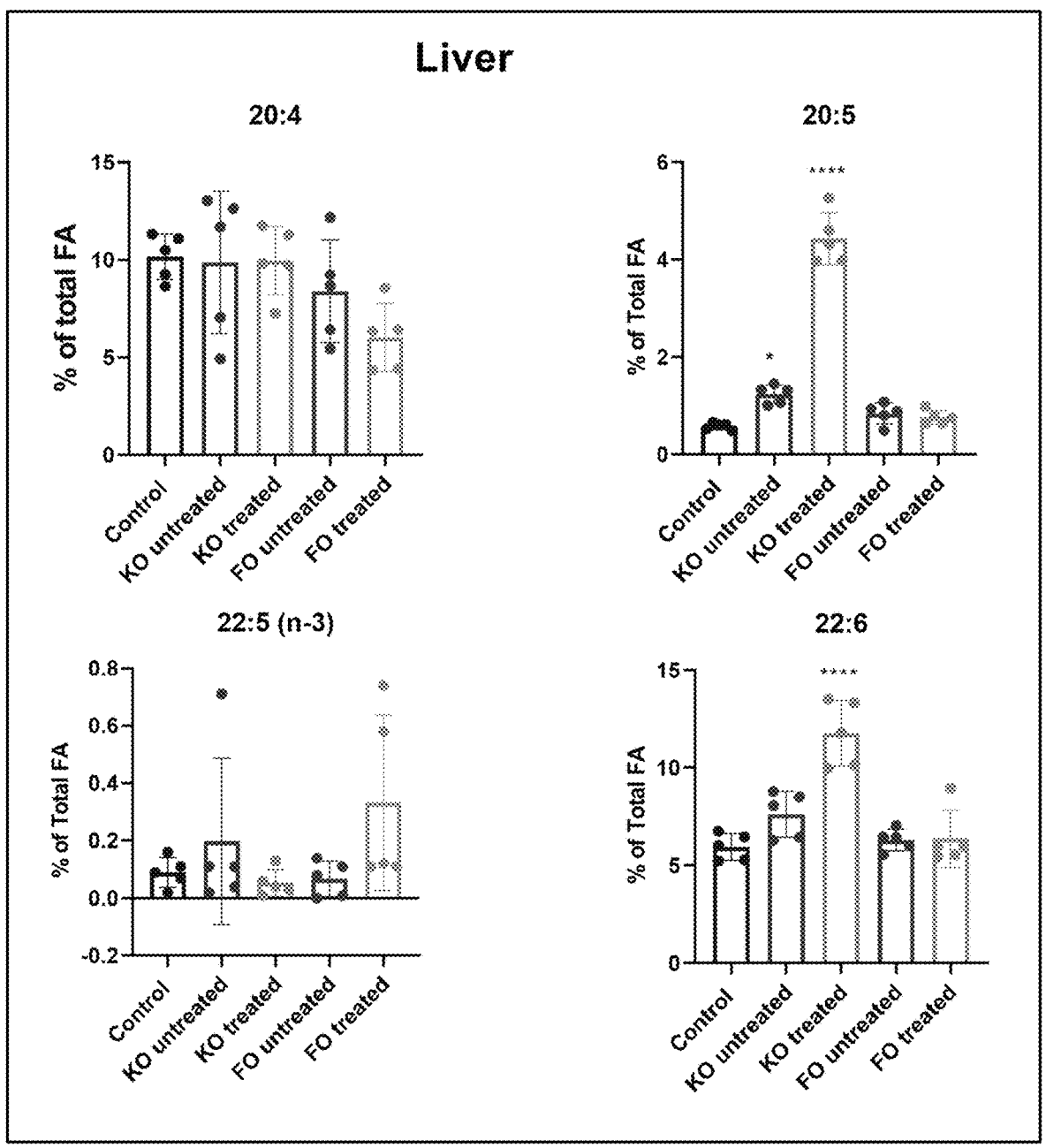
FIG. 21 shows the effect of dietary fat on the fatty acid composition of liver. The fatty acid analysis of total lipids by GC/MS was as described in the text. The values shown are mean±SD of 5 mice in each group. Statistical significance between control and experimental diets was determined by one-way ANOVA, with post-hoc Tukey multiple comparison test. The symbols for significance are the same as under FIG. 12.

Liver In the liver the EPA content was significantly increased by both untreated and lipase-treated krill oil (FIG. 21). However, the increase was 6-fold greater after lipase treatment. The DHA level was increased significantly only by the lipase-treated krill oil. The increase in EPA and DHA occurred at the expense of 16:0, which was reduced from 28.8% in control to 25.5% in the lipase-treated krill oil group. Fish oil had no effect on either EPA or DHA whether treated with lipase or not. However, there was a reduction in 18:0 in the lipase-treated fish oil group (8.3% vs 10.6% in control). No significant changes occurred in either ARA or DPA contents of the liver with any of the preparations.

Figure 22:
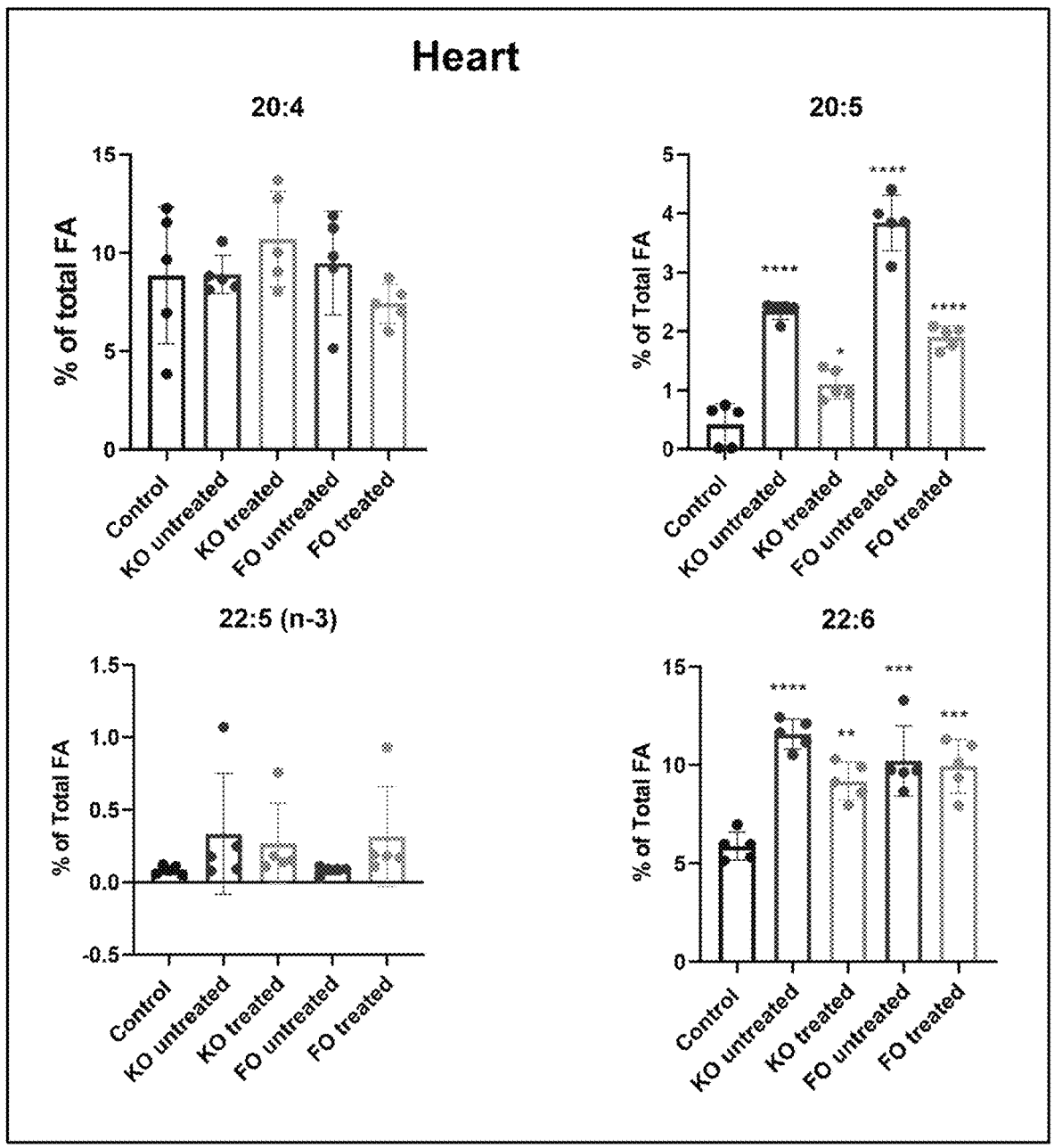
FIG. 22 shows the effect of dietary fat on the fatty acid composition of heart. Total lipids of heart were extracted and analyzed for the fatty acid composition by GC/MS as described in the text. The values shown are mean±SD of 5 mice in each group. Statistical significance between control and experimental diets was determined by one-way ANOVA, with post-hoc Tukey multiple comparison test. The symbols for significance are the same as under FIG. 12.

Heart In the heart, all the preparations increased both EPA and DHA (FIG. 22) Interestingly, however, lipase-treatment of fish oil or krill oil resulted in a decrease in their ability to enrich heart omega 3 fatty acids. No changes were observed in the ARA or DPA levels with any of the dietary supplements. No significant changes occurred in other major fatty acids, including 16:0, 18:0, 18:1, or 18:2 (not shown).

Discussion

Dietary EPA and DHA occur most commonly in the form of TAG (fish oil, algal oil) or phospholipid (krill oil). Currently supplements are also available as the ethyl ester (ex: Lovaza, Vascepa) and free fatty acid (ex: Epanova) forms of EPA and DHA. However, none of these preparations significantly enrich brain EPA or DHA at the recommended doses, although they enrich most other tissues. This is apparently because these supplements are absorbed predominantly as TAG (16, 31), whereas the transporter at the BBB is specific for the LPC form of EPA or DHA (15). Although krill oil has about 40% phospholipids by weight, the EPA and DHA in the phospholipids are present in the sn-2 position, and are released as free fatty acids during digestion by the pancreatic $PLA_2$. The released EPA and DHA are subsequently absorbed as TAG, and therefore will not enrich brain omega 3 fatty acids. The aim of the current study is to demonstrate that one can increase the efficacy of krill oil to enrich brain EPA and DHA by predigesting the PC of krill oil with a lipase that is specific for the sn-1 position, and thus generating LPC-EPA and LPC-DHA, which will then be absorbed as phospholipids and preferentially enrich brain omega 3 fatty acids. For comparison, we have also treated fish oil, which contains no phospholipid, with the lipase and therefore does not generate LPC, but will generate MAG and free fatty acids. The results presented here show that lipase-treatment of krill oil enhances its ability to enrich brain EPA by 10-70 fold, and brain DHA by 15-83%, compared to the untreated krill oil, whereas fish oil had no effect on brain omega 3 fatty acids either with or without lipase treatment. It should be pointed out that there was also a small but significant increase in brain DHA by the untreated krill oil, apparently because of the small amounts of LPC-EPA and LPC-DHA present in it, and therefore the stimulation by lipase treatment appears less striking. Furthermore, since the lipase treatment did not convert all of PC to LPC under the conditions employed, the potential to increase the brain omega 3 fatty acids by lipase treatment of krill oil is even higher than shown here.

Although the lipase-treated krill oil was highly efficient in increasing brain EPA and DHA, it had no effect on the adipose tissue omega 3 fatty acids. Similarly, in the heart, all other preparations increased EPA and DHA more efficiently than the lipase-treated krill oil, whereas in the liver, the lipase-treated krill oil was more efficient than all other preparations. These results show the differential metabolic fates of omega 3 fatty acids absorbed as either TAG or as phospholipids, as we proposed earlier (17). Since the chylomicrons first pass through the adipose tissue, muscle, and the heart before they enter the liver as remnants, the majority of the omega 3 fatty acids from the chylomicron TAG are taken up by the lipoprotein lipase-mediated uptake in the adipose tissue, muscle, and heart. The omega 3 fatty acids from the phospholipids, on the other hand, are predominantly taken up by the liver in the form of chylomicron remnants. The EPA and DHA are hydrolyzed and incorporated into membranes or lipoproteins, and partly secreted by the liver in the form of LPC (32-34), which are then taken up by the brain through the Mfsd2a pathway (15). It is also possible that part of LPC-EPA and LPC-DHA in the lipase-treated krill oil are absorbed into circulation as LPC, bypassing the liver, and transported directly to the brain, although we do not have direct evidence for this.

There is some controversy regarding the relative bioavailability of omega 3 fatty acids of fish oil and krill oil. While many studies have claimed higher bioavailability for the krill oil fatty acids (35, 36), others have questioned this conclusion due to the methodology used for the comparison (37). Based on the fasting plasma values of EPA and DHA in our study, the untreated fish oil and krill oil showed similar bioavailability. However, pre-treatment of the oils with lipase increased the plasma EPA and DHA in both cases, but the krill oil showed greater increase after the lipase treatment compared to fish oil. These results suggest that partial hydrolysis with lipase would not only increase the brain omega 3 fatty acids but may be beneficial for the overall bioavailability of omega 3 fatty acids from fish oil and krill oil to all tissues, and this could be especially important in patients with compromised pancreatic function.

Our studies also show that the lipase-treated krill oil significantly increased the BDNF levels in the brain, showing the functional effect of increasing the omega 3 fatty acids in the brain. The increase in BDNF by krill oil corresponded with the increase in brain DHA and EPA, indicating a direct effect of these fatty acids on the expression of BDNF, as reported by other studies (38, 39). Interestingly, fish oil also showed some increase in BDNF of hippocampus, although there was no increase in DHA. BDNF plays a vital role in neurogenesis, neuroplasticity, and neuroprotection. It is known to be decreased in aging, and low levels of BDNF are associated with various psychiatric and neurodegenerative diseases (40). Therefore, the increase in brain BDNF by the lipase-treated krill oil could potentially provide a safe and effective nutraceutical approach for the prevention and treatment for these diseases.

The fatty acid analysis of the oils used was performed by GC/MS. The values (% of total fatty acids) shown are for the final oil mixture (corn oil and either fish oil or krill oil). The analysis of fatty acids of LPC was performed after TLC separation of the chloroform extract of the krill oil mixtures.

TABLE 6

Percentage composition of fatty acids in the diets

|  | Corn oil (control) | Fish oil | Krill oil | Lipase-treated fish oil | Lipase-treated krill oil | LPC in untreated krill oil | LPC in lipase-treated krill oil |
|---|---|---|---|---|---|---|---|
| Total SFA | 14.6 | 20.7 | 21.3 | 19.6 | 20.5 | 58.4 | 2.8 |
| Total MUFA | 28.9 | 28.0 | 27.6 | 28.3 | 28.2 | 20.4 | 11.7 |
| Total n-6 | 55.8 | 41.8 | 41.0 | 43.0 | 41.2 | 2.6 | 2.6 |
| Total n-3 | 0.5 | 9.3 | 9.8 | 8.9 | 9.9 | 18.0 | 82.7 |
| EPA | — | 5.0 | 5.3 | 4.8 | 5.3 | 12.8 | 58.6 |
| DHA | — | 3.0 | 3.1 | 2.9 | 3.2 | 5.2 | 23.9 |

SFA: saturated fatty acids
MUFA: monounsaturated fatty acids

The oils used for diet preparation (including the corn oil filler) were extracted and separated by TLC, using the phospholipid solvent system (chloroform:methanol: water, 65:25:4, by vol.) for krill oil, or neutral lipid solvent system (hexane:diethyl ether:acetic acid, 70:30:1 by vol.) for fish oil. The spots of the lipids shown below were scraped and their fatty acid composition determined by GC/MS as described in the text. The values shown are the percentage of total EPA+DPA recovered in the given lipid, and are from one representative preparation. The small amounts of DAG present in the fish oil samples, and the PE present in the krill samples are not shown here.

TABLE 7

Distribution of omega 3 fatty acids (EPA + DHA) among the major dietary lipids (% of total)

| | % of total EPA + DHA | | | | |
|---|---|---|---|---|---|
|  | LPC | PC | TAG | FFA | MAG |
| Untreated krill oil | 4.1 | 40.0 | 37.5 | 5.0 | * |
| Lipase-treated krill oil | 44.7 | 17.0 | 2.2 | 30.9 | * |
| Untreated fish oil | — | — | 51.2 | 21.8 | 11.7 |
| Lipase-treated fish oil | — | — | 11.5 | 38.2 | 45.8 |

*Not determined

Example 5: Use of Krill Oil LPC Composition to Increase DHA Content in the Retina Materials and Methods Animals and dietary treatments: All studies in animals described here were approved by the Institutional Animal Care and Use Committee of the University of Illinois at Chicago. The retina samples were obtained from our previous studies on the brain accretion of DHA in mice and rats, which were published previously [16, 17, 67]. Male Sprague-Dawley rats (8-week-old) were purchased from Harlan laboratories (Indianapolis, Ind., USA). Male C57 BL/J6 mice (2-4-months-old) were purchased from Jackson Laboratories (Bar Harbor. Me.).

In the first study, male Sprague-Dawley rats (n=5 per group, 8-week-old) were gavaged daily with 10 mg of DHA (40 mg DHA/kg body weight) in the form of TAG-DHA (DHASCO algal oil, DSM Nutritional Products, Columbia, Md., USA), synthetic di-DHA PC (phosphatidylcholine), or synthetic LPC-DHA (sn-1 acyl) for 30 days [17]. The DHA was distributed equally among the three positions of TAG-DHA [17]. In this study we have also included another group of rats which were gavaged with a half dose of LPC-DHA (20 mg DHA/kg) to be comparable with the expected amount of LPC-DHA generated from di-DHA PC during digestion. In the second study, 4-month-old male C57 BL/J6 mice (n=8 per group) were gavaged daily with 40 mg DHA/kg body weight in the form of free (unesterified) DHA, sn-1 acyl LPC-DHA, or sn-2 acyl LPC-DHA for 30 days as described previously [16]. In the third study, male C57 BL/J6 mice (2-months-old, n=5 per group) were fed diets enriched with natural or lipase-treated fish oil or krill oil for 30 days. The total amount of omega-3 FA (eicosapentaenoic acid (EPA)+DHA) was 2.64 g/kg diet in all the diets. The untreated krill oil contained 18% of total omega-3 FA as LPC, whereas the lipase-treated krill oil contained >80% of the total omega-3 FA as LPC. The fish oil diets contained no LPC-EPA or LPC-DHA. The animals were trans-cardially perfused with ice cold phosphate buffered saline under anesthesia and the retinas were collected and kept frozen at −80° C. until the analysis.

Analytical procedures: The total lipids of retina were extracted by Bligh and Dyer procedure [30] and the fatty acids were methylated using methanolic HCl. The fatty acid analysis was carried out by GC/MS (gas chromatography/mass spectroscopy) using Shimadzu QP2010SE equipped with Supelco Omegawax column, as described previously [16]. Total ion current in the range of 50-400 m/z was used for quantification of the methyl esters. For LC/MS/MS (liquid chromatography/tandem mass spectroscopy) analysis, the lipids were extracted by the procedure of Ivanova et al. [27]. The analysis of molecular species of phospholipids was performed on an ABSciex QTRAP mass spectrometer (Redwood City, Calif., USA) coupled with Agilent 2600 UPLC system (Santa Clara, Calif., USA), by multiple reaction monitoring [31]. The internal standards 17:0 LPC, di 17:0 PC, and di 17:0 PE (phosphatidylethanolamine) were used for the quantification of the corresponding molecular species, without applying any correction factors for the differences in the ion intensity of different molecular species.

Statistics and correlations: The significance of differences between treatment groups was determined by a one-way ANOVA, with Tukey post-hoc multiple comparison corrections or unpaired t-test between control and treated samples adjusted with Holm-Sidak method (Graphpad Prism 8.0, San Diego, Calif., USA).

Results

Comparative Effects of Dietary DHA in the Form of PC, TAG, and LPC in Rats

Figure 23:
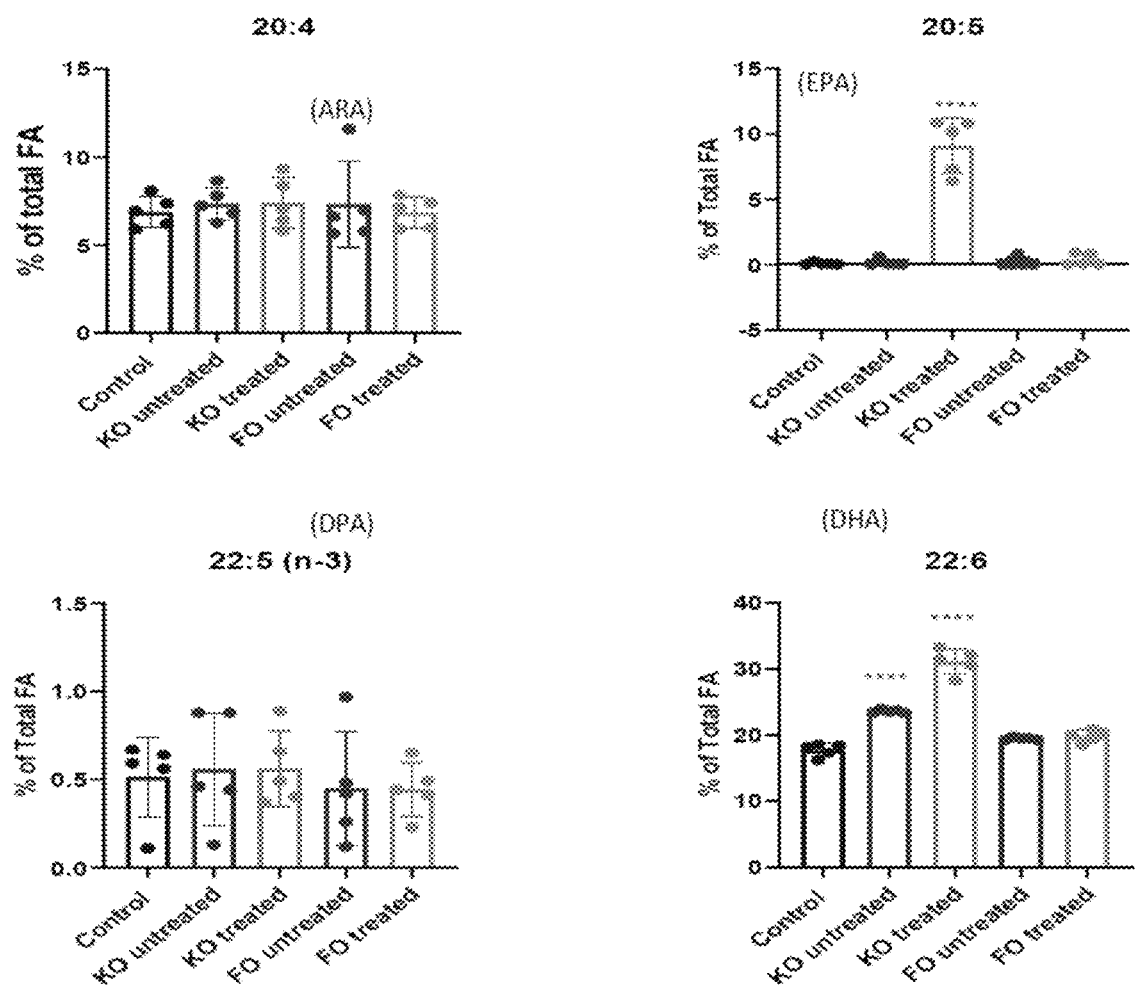
FIG. 23 shows that krill oil, which contains EPA and DHA at sn-2 position of PC treated with a lipase which specifically hydrolyzes sn-1 fatty acid, generating LPC-EPA and LPC-DHA. Feeding this preparation to normal mice resulted in significant increase in retinal EPA and DHA. Similar treatment of fish oil, which contains EPA and DHA only in triglyceride form, had no effect on retinal EPA or DHA.
Figure 24:
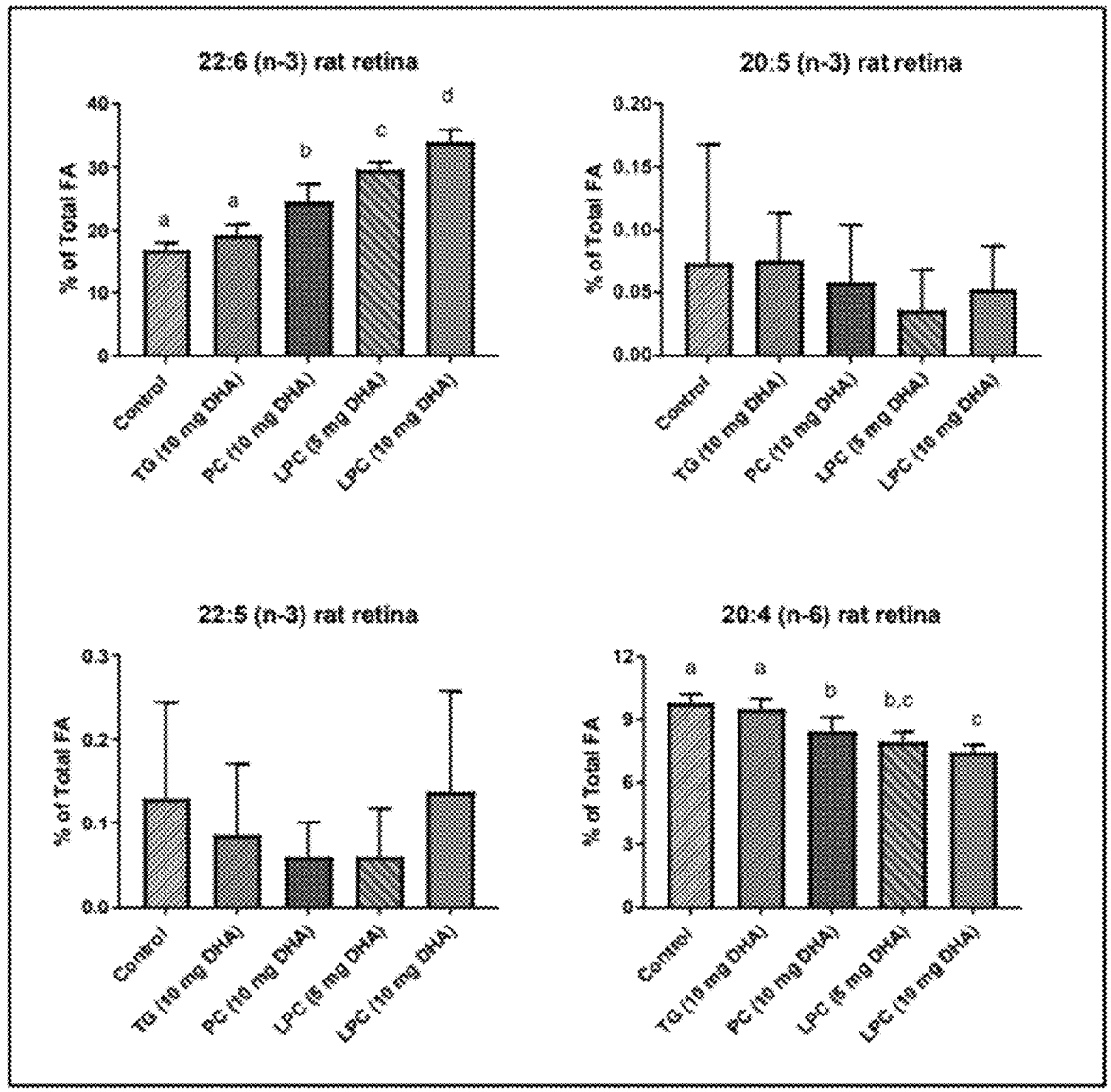
FIG. 24 shows incorporation of dietary DHA fed in the form of PC, TAG, or LPC into rat retinal lipids. Normal male Sprague-Dawley rats (8-week-old; n=5 per group) were gavaged daily with 10 mg DHA in 250 µL corn oil in the form of TAG-DHA, di-DHA PC, or LPC-DHA for 30 days. In addition, a half-dose of LPC-DHA (5 mg DHA) was used to be comparable to the amount of LPC-DHA expected to be generated by di-DHA PC during digestion. All animals were on regular rodent chow that contained no DHA, but contained 17.4 mg α-linolenic acid (18:3, n-3) per g of chow. Retinal FA were analyzed by GC/MS as described in the text. The percent composition of 20:4 (n-6), 20:5 (n-3), 22:5 (n-3), and 22:6 (n-3) are shown here. The total FA composition is shown in Table 1. The significance of differences between the treatment groups was determined by a one-way ANOVA, with Tukey multiple post-hoc test (Graphpad Prism 8.0). Bars without common superscripts are significantly different from each other (p<0.05). TG: triacylglycerol; PC: phosphatidylcholine; LPC: lysophosphatidylcholine; FA: fatty acid; GC/MS: gas chromatography/mass spectroscopy.

We have previously demonstrated that rat brain DHA is efficiently enriched by dietary LPC-DHA and di-DHA PC, but not by TAG-DHA [17]. Since the mechanism of DHA uptake appears to be similar for brain and retina [66], we determined the enrichment of retinal DHA in the same groups of animals. Normal rats were gavaged with 10 mg DHA/day (40 mg DHA/kg) in the form of TAG-DHA, di-DHA PC, or LPC-DHA (sn-1 acyl) for 30 days, and the retinal FA composition was determined by GC/MS. In addition, a half dose of LPC-DHA (20 mg/kg) was used, in order to be equivalent to the expected generation of LPC-DHA by the digestion of di-DHA PC in the intestine by pancreatic phospholipase $A_2$ ($PLA_2$). The concentrations of omega-3 FA and arachidonic acid are shown in FIG. 23, while the total FA composition is shown in Table 8. As shown in FIG. 24, the percentage of DHA in retina was significantly increased by di-DHA PC (+45%) and by LPC-DHA (+101%), but not by TAG-DHA (+13%, not significant). The half dose of LPC-DHA (5 mg/rat) was more efficient (+75%) than the full dose of di-DHA PC (+45%), indicating that the hydrolysis of di-DHA PC by the pancreatic $PLA_2$ (phospholipase A2) may not be efficient. Remarkably, although the DHA content of normal rat retina is very high (16.88% of total FA), it was doubled by feeding the full dose of LPC-DHA (to 33.98% of total FA), indicating the wide range of retinal membrane DHA content that can be achieved through diet. The increase in DHA occurred largely at the expense of arachidonic acid as we found in the brain [17], but the DHA also replaced saturated FA (16:0 and 18:0) in the retina (Table 8). There were no changes in either EPA (20:5 (n-3)) or DPA (22:5 (n-3)) of retina by any of the treatments.

Comparative Effects of Free DHA and Isomers of LPC-DHA in Mice

Figure 25:
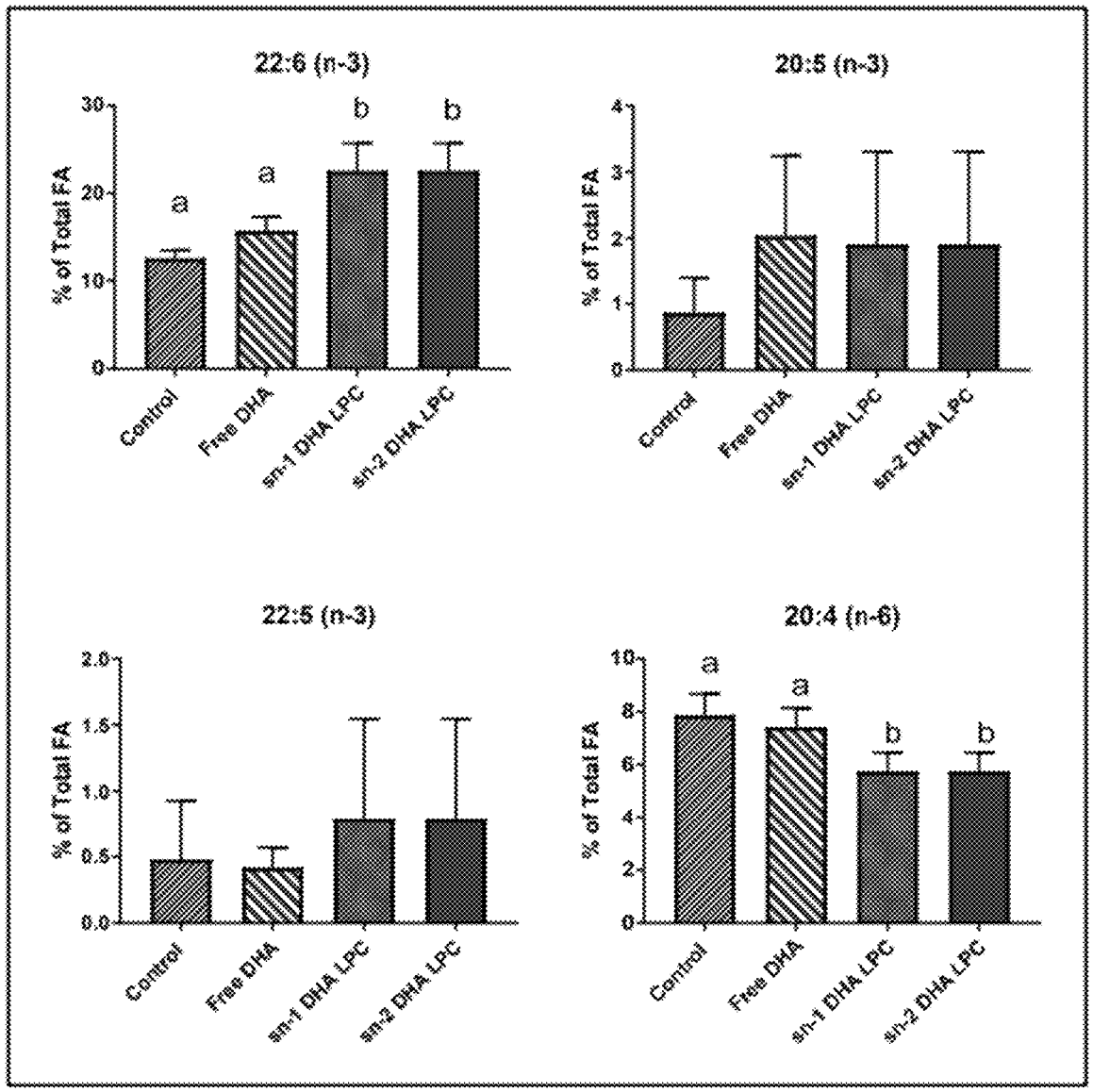
FIG. 25 shows effect of dietary free (unesterified) DHA, sn-1 DHA-LPC, and sn-2 DHA LPC on mouse retinal FA. Normal male mice (C57 BL/J6, 16-week-old) were gavaged daily with 1 mg DHA in the form of free DHA, sn-1 DHA LPC, or sn-2 DHA LPC in 80 µL corn oil for 30 days. Retinal FA composition was analyzed by GC/MS. Only the values for arachidonic acid and the omega-3 FA are shown here (mean±SD, 8 animals/group). The total FA composition is shown in Table 2. Bars without common superscripts are significantly different from each other (p<0.05) by a one-way ANOVA with Tukey post-hoc correction. SD: standard deviation; sn-1 and sn-2: stereospecific numbering 1 and 2 respectively; LPC: lysophosphatidylcholine; DHA: docosahexaenoic acid.

Previous studies suggested that for the uptake of DHA by the brain, the DHA has to be in the sn-2 position of LPC, since that is the natural position in phospholipids in vivo [68, 69]. However, our recent studies showed that sn-1 DHA LPC and sn-2 DHA LPC were equally effective in enriching mouse brain DHA and in improving brain function [16]. We analyzed the retinal FA composition in mice fed free (unesterified) DHA, sn-1 DHA LPC, and sn-2 DHA LPC, to determine whether there is a preference for the sn-2 acyl isomer of LPC for transport through blood-retina barrier. As shown in FIG. 25 and Table 9, free DHA had no effect on retinal DHA, similar to the effect of TAG-DHA in rats. However, both isomers of LPC-DHA increased the retinal DHA by 80%, showing that the uptake of DHA by retina is similar to that of brain, and involves the Mfsd2a transporter as shown by others [66]. Furthermore, the transporter at the blood-retina barrier did not distinguish between the two isomers of LPC-DHA, as we found for the brain [16]. There was no effect on either EPA (20:5, n-3) or DPA (22:5, n-3) content by any of the DHA treatments. There was a significant decrease in arachidonate by the two isomers of LPC-DHA, but not by free DHA. In addition, there were significant decreases in saturated fatty acids (16:0 and 18:0) as well as in 18:1 by LPC-DHA, but not by free DHA. These results suggest that, similar to the results in rats, the increase in mouse retinal DHA occurred by the replacement of not only arachidonate but also the saturated FA and 18:1.

Figures 26A, 26B:
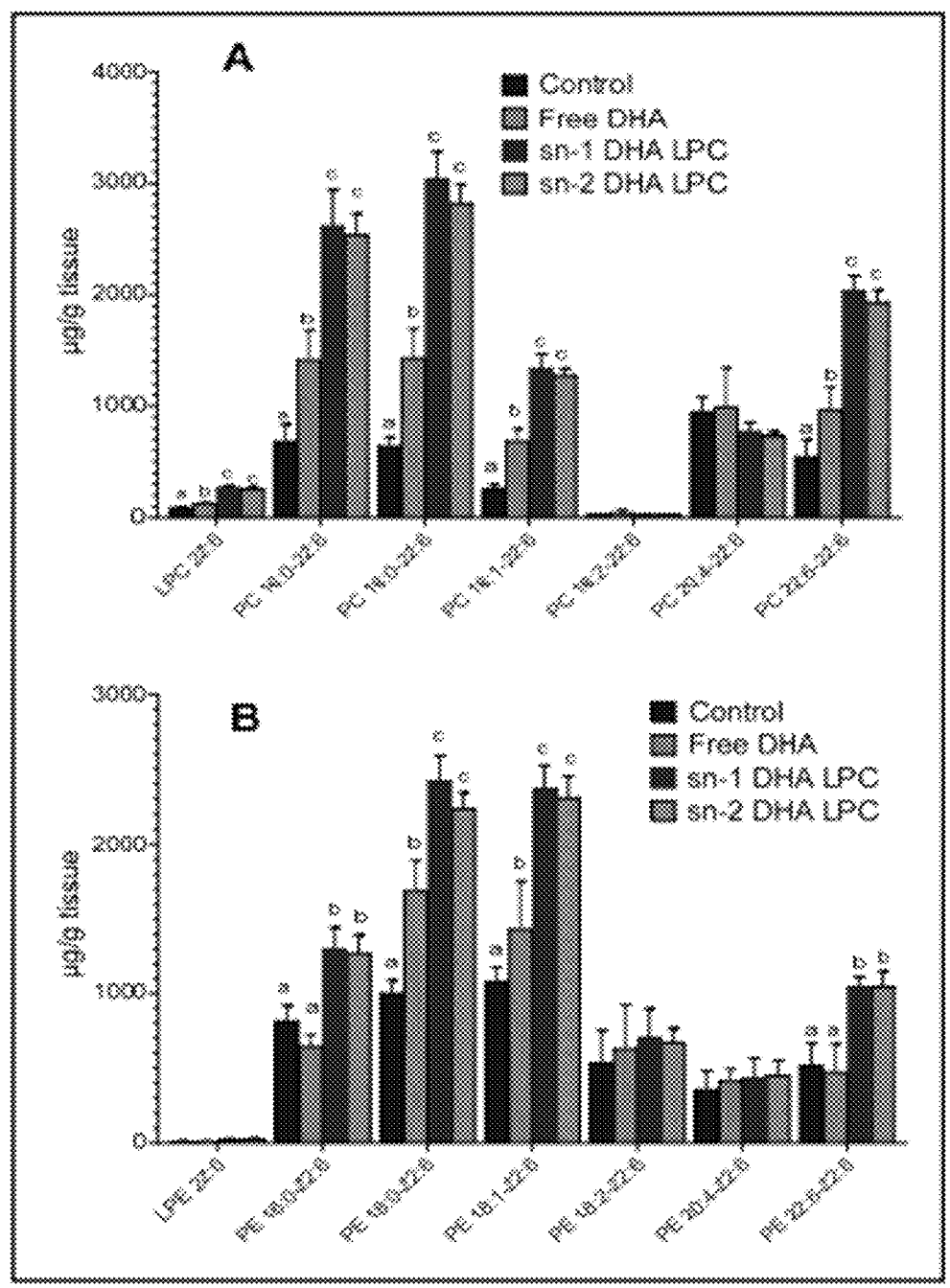
FIG. 26A-B shows molecular species of mouse retinal phospholipids containing DHA. The animals were gavaged with free (unesterified) DHA or two isomers of LPC-DHA as described under FIG. 2. The molecular species of PC (A) and PE (B) which contain DHA were analyzed using multiple reaction monitoring by LC/MS/MS, as described in the text, using 17:0 LPC, 17:0-17:0 PC, and 17:0-17:0 PE as internal standards. Bars without common superscripts are significantly different from each other by a one-way ANOVA, and Tukey post-hoc analysis (mean±SD), 6 animals/group). PE: phosphatidylethanolamine; PC: phosphatidylcholine; sn-1 and sn-2: stereospecific numbering 1 and 2 respectively; DHA: docosahexaenoic acid; LC/MS/MS: liquid chromatography/tandem mass spectroscopy; SD: standard deviation; LPC: lysophosphatidylcholine; DHA: docosahexaenoic acid.

The molecular species of PC and PE, which contain DHA, were analyzed by LC/MS/MS, in order to determine whether the metabolic fate of the two LPC-isomers in retina differ from each other. As shown in FIG. 26, both isomers of LPC-DHA increased most of the major DHA-containing PCs and PEs, except 20:4-22:6 PC and 20:4-22:6 PE, possibly because of the decrease in retinal 20:4 by the LPC treatment. There were no significant differences between the effects of the two isomers of LPC on molecular species composition of PC or PE. Although the total DHA content of retina was not significantly increased by free DHA (FIG. 27), a few individual species of PC and PE containing DHA were increased, but at much lower levels compared to LPC-DHA. Retinal LPC-DHA, but not LPE-DHA was increased after the treatment with dietary LPC-DHA. Unlike the brain, in which DHA was more prevalent in the PE species [16], retina contained more DHA in the PC species. PE: phosphatidylethanolamine.

Effect of Fish Oil and Krill Oil on Mouse Retinal Omega-3 FA

Although previous studies with fish oil showed no significant enrichment of retinal DHA or EPA in the adult animals [49], we recently demonstrated that pre-treatment of krill oil with a lipase, which generates LPC-EPA and LPC-DHA, enables significant enrichment of both DHA and EPA in the brains of adult mice [67]. On the other hand, similar treatment of fish oil, which generates free EPA and DHA or monoacylglycerol EPA and DHA, did not have any effect on brain omega-3 FA. In order to determine whether lipase-treated krill oil can also be used for enriching retinal DHA and EPA, we analyzed the FA composition of retina in mice treated with fish oil and krill oil, which have been treated with lipase or not.

Figure 27:
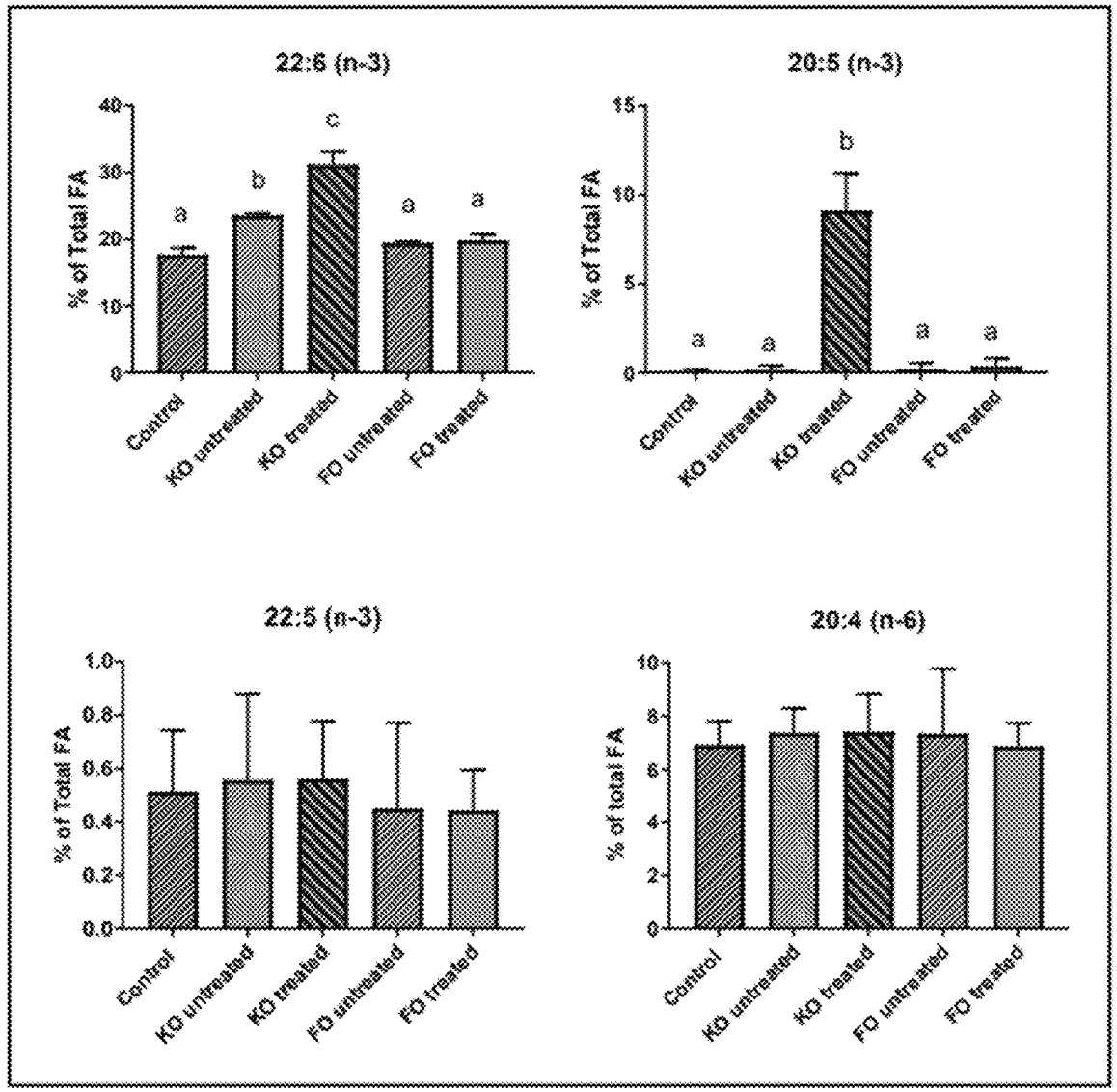
FIG. 27 shows the effect of feeding untreated or lipase-treated fish oil and krill oil on mouse retinal FA. Normal male mice (8-week-old) were fed diets (AIN93G) containing 7% total fat and supplemented with 0.264% EPA+DHA in the form of fish oil or krill oil, which have been treated (or not) with Mucor lipase. The mice were fed the diets ad lib for 30 days and the retinal FA were analyzed by GC/MS. The percentages of 20:4 (n-6), 20:5 (n-3), 22:5 (n-3) and 22:6 (n-3) are shown here (mean±SD, 5 mice/group. The total FA composition is shown in Table 3. Bars without common superscripts are significantly different from each other by a one-way ANOVA and Tukey post-hoc analysis. KO: krill oil; FO: fish oil; FA: fatty acid; EPA: eicosapentaenoic acid; GC/MS: gas chromatography/mass spectroscopy; DHA: docosahexaenoic acid.

As shown in FIG. 27 and Table 10, retinal DHA was increased above the control value by 33% after feeding untreated krill oil, possibly because of the presence of small amounts of LPC-DHA in the krill oil preparation [67]. However, feeding lipase-treated krill oil increased the retinal DHA by 76%, showing a 2.3-fold stimulation of DHA enrichment by lipase treatment. Furthermore, there was a 100-fold increase in retinal EPA by the lipase-treated krill oil, but no increase with untreated krill oil or the fish oil. This supports our previous observation that feeding LPC-EPA does increase EPA levels in the brain and retina, contrary to the previous reports of the lack of EPA enrichment in these tissues by omega-3 FA-enriched diets [18, 19, 20]. In contrast to the results with pure LPC-DHA, we did not find a significant displacement of retinal arachidonate by DHA after treatment with lipase-treated krill oil. Instead, DHA and EPA appeared to replace saturated FA and oleic acid (18:1, n-9). There was also some decrease in saturated FA and 18:1 in the animals fed untreated krill oil, but these decreases did not reach statistical significance (Table 10).

Discussion

Retinal DHA is known to decline with age [54] as well as in diabetes [57, 58, 59]. Furthermore, the reduced DHA levels have been associated with several retinal diseases, the most prominent being diabetic retinopathy (DR) [54, 56, 44]. DR affects almost 100 million people world-wide and is the most common cause of blindness in the adult population [70]. It is believed that the oxidative stress and chronic inflammation induced by hyperglycemia are the major underlying causes of DR [71]. DHA, which is uniquely concentrated in retina, has been shown to have both anti-oxidant and anti-inflammatory properties [54, 72, 73]. In addition to DR, DHA deficiency has also been implicated in other diseases of the eye, including retinitis pigmentosa [74], glaucoma [75, 76], age-related macular degeneration [55], dry eye disease [77], and Alzheimer's related blindness [41]. A common element of all of these diseases is chronic inflammation.

Therefore, it is important to investigate whether the retinal DHA levels can be increased through diet in adult mammals and thereby prevent or treat these diseases. The results presented here show, that despite the very high initial levels of DHA in the normal retina, it can be further increased by up to 100% through dietary LPC-DHA, but not by dietary free DHA or TAG-DHA. To our knowledge, this is the highest enrichment achieved in retinal DHA with dietary supplementation in normal adult animals. Previous studies found no or marginal increases in retinal omega-3 levels even after treatment with very high concentrations of dietary omega-3 FA. For example, Prokopiou et al. [78] fed aged (2-year-old) mice 200 mg omega-3 FA/day in the form of fish oil for 60 days, and found actually a decrease in retinal DHA (−21%), although retinal EPA, which is a minor constituent, increased by 42%. Similarly, gavaging ABCA4−/− mice (Stargardt disease) with 206 mg/day of omega-3 FA (172 mg EPA+34 mg DHA) for three months resulted in no change in retinal DHA, although a 67% increase in retinal EPA (from 0.93% to 1.56% of total) was observed [79]. A study by Schnebelen et al. [80] showed that feeding 3-week-old rats with 5% fat diet containing 20% omega-3 FA for three months resulted only in an 8% increase in retinal DHA. In contrast to these studies, using transgenic mice carrying fat-1 gene, which converts endogenous omega-6 FA to omega-3 FA, Suh et al. [82] and Tanito et al. [81] reported a near doubling of retinal DHA compared to the wild type controls. However, the increase in retinal DHA by genetic manipulation rather than through diet appears to cause abnormal electroretinograms and susceptibility to oxidative stress, as reported by these workers. On the other hand, Connor et al. [83] reported that increasing the DHA content of retina in neonatal mice through diet prevents retinopathy of prematurity by inhibiting the pathological neovascularization. Furthermore, Sapieha et al. [56] showed that supplementation of diet with high concentration of omega-3 FA (2% of diet) preserved retinal function in a mouse model of type 2 diabetes and enhanced glucose tolerance, although changes in retinal DHA levels were not reported. Similar benefits on diabetic retinopathy were shown in rats by Tikhonenko et al. [44] who fed 5% calories as menhaden oil. However, the dose of omega-3 FA required to achieve these beneficial effects is impractical in clinical setting, since the equivalent dose in humans, using allometric calculations [84], would be about 14 g of omega-3 FA/day in a 70 kg human, based on the Sapieha et al. study, or about 16 mL fish oil/day according to the Tikhonenko et al. study. In contrast, the dose of LPC-DHA required to nearly double the retinal DHA is about 50 times lower than the above studies and is therefore easily applicable to clinical conditions.

Unlike the brain which acquires DHA predominantly through the Mfsd2a pathway, retina appears to acquire DHA through multiple pathways, since a deficiency of Mfs2a results in only a 45% reduction in retinal DHA, and a 57% reduction in VLCFA [85]. Thus, the studies by Bazan [41] showed the importance of Adiponectin receptor for maintaining the DHA levels of retina, whereas the role of FA-binding proteins and lipoprotein receptors have been proposed by others [54, 65]. These pathways may account for the small increase in retinal DHA by dietary free DHA and TAG. Retina also has an efficient recycling mechanism to retain DHA by the phagocytosis of retinal pigment epithelial cells [52, 41], possibly accounting for the milder effects of congenital Mfsd2a deficiency on retinal function [66, 85], compared to the brain function [15]. Another difference between the brain and retina was that whereas DHA replaced mostly arachidonic acid in the brain [16, 17, 67], it replaced more saturated fatty acids and oleic acid than arachidonic acid in retina. While the decrease in arachidonic acid is believed to be beneficial because of its role in the generation of pro-inflammatory eicosanoids, the physiological effects of decreasing the saturated fatty acids and oleic acid in retina are not clear.

In contrast to DHA, the EPA content of retina is very low, and is not increased substantially even after feeding EPA-rich supplements, although DHA levels are increased by these treatments [80, 83]. Therefore, it has been assumed that either EPA does not enter the brain and retina, convert rapidly to DHA, or oxidized without net accumulation [25, 86]. In the current study, although EPA levels of retina were not increased after feeding pure LPC-DHA, marked increases occurred after feeding lipase-treated krill oil which contained both LPC-EPA and LPC-DHA. Therefore, we suggest that the failure of previous studies to show an increase in brain or retinal EPA was due to the inability of the supplements to generate LPC-EPA in vivo. We have previously shown that similar enrichment of brain EPA and retinal EPA occurred after feeding pure LPC-EPA [26]. Increasing retinal EPA in addition to DHA may be more beneficial than increasing only its DHA content, because EPA is the preferred substrate for the synthesis of VLCFA [87, 88], which have unique functional significance in retina [89]. EPA is also known to compete more effectively than DHA against arachidonate and thereby inhibit synthesis of pro-inflammatory prostaglandins.

Most studies on omega-3 FA focus on increasing only the EPA and DHA levels of the tissues, but an ancillary benefit of dietary LPC-EPA/DHA, in comparison to fish oil or ethyl esters, is that for each molecule of DHA or EPA taken up by the retina and brain through the Mfsd2a pathway, a molecule of choline is simultaneously taken up. Choline is an essential component of acetyl choline as well as membrane phospholipids, and plays a critical role in vision [90]. In fact, citicholine, (CDP-choline), a precursor of choline phospholipids, is used clinically for treatment of retinopathies and glaucoma [90]. Therefore, LPC-EPA/DHA could provide the combined benefits of omega-3 FA and citicholine in a single effective preparation.

TABLE 8

Effect of dietary TG-DHA, di-DHA PC, and LPC-DHA on rat retinal fatty acid composition.

| F.A. | Control Mean S.D. | TG-DHA Mean S.D. | PC-DHA Mean S.D. | LPC-DHA 5 mg Mean S.D. | LPC-DHA 10 mg Mean S.D |
|---|---|---|---|---|---|
| 12:0 | 4.39 ± 1.19 | 4.71 ± 2.09 | 4.57 ± 1.49 | 3.10 ± 0.08 | 3.10 ± 0.60 |
| 14:0 | 0.08 ± 0.04 | 0.17 ± 0.18 | 0.97 ± 1.97 | 0.52 ± 0.90 | 0.11 ± 0.13 |
| 16:0 | 22.14 ± 0.65 | 21.52 ± 1.37 | 19.06 ± 0.76** | 18.05 ± 0.84** | 17.27 ± 0.94** |
| 16:1 (n-7) | 0.73 ± 0.06 | 0.74 ± 0.09 | 0.65 ± 0.04 | 0.66 ± 0.08 | 0.68 ± 0.05 |
| 17:1 (n-7) | 0.02 ± 0.02 | 0.12 ± 0.03* | 0.03 ± 0.02 | 0.01 ± 0.00 | 0.02 ± 0.02 |
| 18:0 | 20.26 ± 0.92 | 19.09 ± 1.30 | 17.79 ± 0.97 | 16.84 ± 0.43 | 15.62 ± 0.85** |
| 18:1 (n-9) | 18.9 ± 0.90 | 18.21 ± 1.57 | 17.70 ± 1.26 | 17.07 ± 0.94 | 15.81 ± 1.46 |
| 18:1 (n-7) | 4.40 ± 0.28 | 4.09 ± 0.16 | 3.91 ± 0.25 | 3.79 ± 0.16 | 3.43 ± 0.28* |
| 18:2 (n-6) | 0.97 ± 0.05 | 1.05 ± 0.36 | 0.95 ± 0.22 | 0.93 ± 0.26 | 0.97 ± 0.26 |
| 18:3 (n-6) | 0.39 ± 0.02 | 0.38 ± 0.11 | 0.49 ± 0.13 | 0.50 ± 0.11 | 0.37 ± 0.08 |
| 18:3 (n-3) | 0.03 ± 0.02 | 0.09 ± 0.10 | 0.07 ± 0.07 | 0.08 ± 0.05 | 0.04 ± 0.04 |
| 20:0 | 0.05 ± 0.04 | 0.08 ± 0.05 | 0.05 ± 0.03 | 0.04 ± 0.03 | 0.04 ± 0.03 |
| 20:1 (n-9) | 0.05 ± 0.05 | 0.06 ± 0.05 | 0.07 ± 0.03 | 0.05 ± 0.03 | 0.03 ± 0.02 |
| 20:2 (n-6) | 0.08 ± 0.04 | 0.04 ± 0.01 | 0.06 ± 0.05 | 0.05 ± 0.04 | 0.06 ± 0.04 |
| 20:3 (n-6) | 0.08 ± 0.10 | 0.16 ± 0.18 | 0.06 ± 0.04 | 0.09 ± 0.13 | 0.13 ± 0.15 |
| 20:4 (n-6) | 9.77 ± 0.44 | 9.49 ± 0.52 | 8.45 ± 0.67 | 7.94 ± 0.48* | 7.44 ± 0.37** |
| 22:0 | 0.04 ± 0.02 | 0.05 ± 0.04 | 0.07 ± 0.07 | 0.03 ± 0.02 | 0.04 ± 0.02 |
| 20:5 (n-3) | 0.07 ± 0.09 | 0.08 ± 0.04 | 0.06 ± 0.05 | 0.04 ± 0.03 | 0.05 ± 0.04 |
| 22:2 (n-6) | 0.11 ± 0.08 | 0.13 ± 0.06 | 0.12 ± 0.05 | 0.12 ± 0.04 | 0.13 ± 0.03 |
| 22:4 (n-6) | 0.05 ± 0.03 | 0.31 ± 0.17 | 0.07 ± 0.05 | 0.24 ± 0.45 | 0.32 ± 0.62 |
| 22:5 (n-6) | 0.02 ± 0.01 | 0.03 ± 0.04 | 0.02 ± 0.01 | 0.02 ± 0.03 | 0.03 ± 0.02 |
| 22:5 (n-3) | 0.13 ± 0.11 | 0.09 ± 0.09 | 0.06 ± 0.04 | 0.06 ± 0.06 | 0.14 ± 0.12 |
| 22:6 (n-3) | 16.88 ± 1.15 | 19.20 ± 1.67 | 24.53 ± 2.73* | 29.56 ± 1.23** | 33.98 ± 1.91** |
| 24:1 (n-9) | 0.06 ± 0.04 | 0.07 ± 0.04 | 0.05 ± 0.02 | 0.03 ± 0.02 | 0.03 ± 0.02 |
| 16:0 DMA | 0.03 ± 0.03 | 0.09 ± 0.08 | 0.05 ± 0.08 | 0.12 ± 0.12 | 0.08 ± 0.10 |
| 18:0 DMA | 0.16 ± 0.30 | 0.05 ± 0.03 | 0.03 ± 0.02 | 0.03 ± 0.02 | 0.02 ± 0.01 |
| 18:1 DMA | 0.06 ± 0.05 | 0.08 ± 0.08 | 0.06 ± 0.04 | 0.05 ± 0.02 | 0.06 ± 0.06 |

*$p < 0.05$ compared to control,

**$p < 0.005$ compared to control, unpaired t-test adjusted with Holm-Sidak method.

TG: triacylglycerol;

PC: phosphatidylcholine;

LPC: lysophosphatidylcholine;

DMA: dimethylacetal;

DHA: docosahexaenoic acid;

F.A.: fatty acid;

S.D.: standard deviation.

TABLE 9

Effect of free DHA, sn-1 DHA LPC, and sn-2 DHA LPC on fatty acid composition of mouse retina.

| F.A. | Control Mean ± S.D. | Free DHA Mean ± S.D. | sn-1 DHA LPC Mean ± S.D. | sn-2 DHA LPC Mean ± S.D. |
|---|---|---|---|---|
| 12:0 | 0.26 ± 0.14 | 0.60 ± 0.35 | 0.73 ± 0.47 | 0.73 ± 0.47 |
| 14:0 | 0.50 ± 0.25 | 0.20 ± 0.17 | 0.30 ± 0.17 | 0.30 ± 0.17 |
| 16:0 | 17.92 ± 1.41 | 16.11 ± 1.56 | 14.62 ± 1.22** | 14.62 ± 1.22** |
| 16:1 (n-7) | 0.38 ± 0.17 | 0.55 ± 0.28 | 0.47 ± 0.34 | 0.47 ± 0.34 |
| 17:1 (n-7) | 0.29 ± 0.13 | 0.43 ± 0.16 | 0.48 ± 0.38 | 0.48 ± 0.38 |
| 18:0 | 18.90 ± 1.05 | 17.32 ± 0.66 | 15.44 ± 1.50** | 15.44 ± 1.50** |
| 18:1 (n-9) | 18.23 ± 0.82 | 17.14 ± 0.78 | 15.56 ± 1.16** | 15.56 ± 1.16** |
| 18:1(n-7) | 4.64 ± 0.48 | 4.18 ± 0.34 | 3.82 ± 0.62 | 3.82 ± 0.62 |
| 18:2 (n-6) | 0.69 ± 0.45 | 0.99 ± 0.65 | 1.38 ± 0.49 | 1.38 ± 0.49 |
| 18:3 (n-6) | 0.36 ± 0.19 | 0.49 ± 0.36 | 0.60 ± 0.47 | 0.60 ± 0.47 |
| 18:3 (n-3) | 0.54 ± 0.43 | 0.49 ± 0.15 | 0.51 ± 0.42 | 0.51 ± 0.42 |
| 20:0 | 1.86 ± 0.69 | 1.90 ± 0.64 | 1.18 ± 0.72 | 1.18 ± 0.72 |
| 20:1 (n-9) | 3.71 ± 0.42 | 3.42 ± 0.59 | 2.87 ± 0.60 | 2.87 ± 0.60 |
| 20:2 (n-6) | 1.28 ± 0.84 | 0.71 ± 0.50 | 0.88 ± 0.95 | 0.88 ± 0.95 |
| 20:3 (n-6) | 0.69 ± 0.54 | 1.30 ± 0.66 | 1.44 ± 0.35 | 1.44 ± 0.35 |
| 20:4 (n-6) | 7.86 ± 0.81 | 7.42 ± 0.72 | 5.75 ± 0.71** | 5.75 ± 0.71** |
| 22:0 | 1.20 ± 0.41 | 1.08 ± 0.59 | 1.24 ± 0.95 | 1.24 ± 0.95 |
| 20:5 (n-3) | 0.86 ± 0.53 | 2.03 ± 1.21 | 1.91 ± 1.40 | 1.91 ± 1.40 |
| 22:2 (n-6) | 0.80 ± 0.34 | 0.77 ± 0.51 | 1.00 ± 0.76 | 1.00 ± 0.76 |
| 22:4 (n-6) | 2.03 ± 0.91 | 2.51 ± 0.85 | 2.23 ± 0.87 | 2.23 ± 0.87 |
| 22:5 (n-3) | 0.48 ± 0.44 | 0.42 ± 0.15 | 0.79 ± 0.76 | 0.79 ± 0.76 |
| 22:6 (n-3) | 12.61 ± 0.91 | 15.74 ± 1.57 | 22.57 ± 3.12** | 22.57 ± 3.12** |
| 24:1 (n-9) | 0.78 ± 0.48 | 0.51 ± 0.25 | 0.49 ± 0.17 | 0.49 ± 0.17 |
| 16:0 DMA | 1.16 ± 0.96 | 0.75 ± 0.56 | 1.02 ± 0.32 | 1.02 ± 0.32 |
| 18:0 DMA | 1.25 ± 1.04 | 2.10 ± 0.88 | 1.96 ± 0.30 | 1.96 ± 0.30 |
| 18:1 DMA | 0.73 ± 0.75 | 0.85 ± 0.56 | 0.78 ± 0.64 | 0.78 ± 0.64 |

**p < 0.005 compared to control, unpaired t-test adjusted with Holm-Sidak method.
DMA: dimethylacetal;
sn-1 and sn-2: stereospecific numbering 1 and 2 respectively;
LPC: lysophosphatidylcholine;
DHA: docosahexaenoic acid;
F.A.: fatty acid;
S.D.: standard deviation

TABLE 10

Effect of feeding unmodified, and lipase-treated krill oil and fish oil on mouse retina fatty acid composition.

| F.A. | Control Mean S.D. | KO Untreated Mean S.D. | KO Treated Mean S.D. | FO Untreated Mean S.D. | FO Treated Mean S.D |
|---|---|---|---|---|---|
| 12:0 | 0.02 ± 0.03 | 0.06 ± 0.06 | 0.07 ± 0.05 | 0.02 ± 0.01 | 0.06 ± 0.05 |
| 14:0 | 0.17 ± 0.27 | 0.38 ± 0.44 | 0.09 ± 0.04 | 0.20 ± 0.33 | 0.03 ± 0.04 |
| 16:0 | 22.07 ± 1.84 | 20.34 ± 1.94 | 12.51 ± 7.01 | 22.20 ± 1.90 | 22.67 ± 2.12 |
| 16:1 (n-7) | 0.20 ± 0.31 | 0.19 ± 0.17 | 0.10 ± 0.13 | 0.06 ± 0.07 | 0.04 ± 0.04 |
| 18:0 | 18.69 ± 0.42 | 17.20 ± 1.25 | 14.20 ± 1.62* | 17.84 ± 0.88 | 18.03 ± 0.13 |
| 18:1 (n-9) | 20.04 ± 0.64 | 14.99 ± 5.59 | 14.75 ± 1.50** | 19.51 ± 0.76 | 19.32 ± 0.99 |
| 18:1 (n-7) | 4.79 ± 0.21 | 4.36 ± 0.42 | 2.35 ± 2.08 | 4.46 ± 0.14 | 3.72 ± 2.09 |
| 18:2 (n-6) | 0.88 ± 0.46 | 0.99 ± 0.51 | 1.10 ± 0.34 | 1.22 ± 0.19 | 0.87 ± 0.69 |
| 18:3 (n-6) | 0.06 ± 0.04 | 0.06 ± 0.06 | 0.18 ± 0.16 | 0.06 ± 0.05 | 0.05 ± 0.01 |
| 18:3 (n-3) | 0.81 ± 0.53 | 0.82 ± 0.74 | 0.29 ± 0.24 | 0.79 ± 0.68 | 0.41 ± 0.31 |
| 20:0 | 0.05 ± 0.03 | 0.03 ± 0.03 | 0.04 ± 0.04 | 0.05 ± 0.03 | 0.02 ± 0.01 |
| 20:1 (n-9) | 2.17 ± 1.17 | 2.00 ± 1.41 | 0.78 ± 0.44 | 2.13 ± 0.55 | 1.12 ± 0.92 |
| 20:2 (n-6) | 0.22 ± 0.19 | 0.38 ± 0.25 | 0.19 ± 0.15 | 0.56 ± 0.39 | 0.21 ± 0.10 |
| 20:3 (n-6) | 0.03 ± 0.02 | 0.11 ± 0.13 | 0.44 ± 0.41 | 0.05 ± 0.02 | 0.23 ± 0.41 |
| 20:4 (n-6) | 6.92 ± 0.88 | 7.37 ± 0.92 | 7.41 ± 1.43 | 7.34 ± 2.44 | 6.87 ± 0.86 |
| 22:0 | 0.10 ± 0.10 | 0.37 ± 0.32 | 0.09 ± 0.10 | 0.14 ± 0.25 | 0.06 ± 0.06 |
| 20:5 (n-3) | 0.09 ± 0.10 | 0.15 ± 0.26 | 9.12 ± 2.09** | 0.18 ± 0.36 | 0.36 ± 0.45 |
| 22:2 (n-6) | 0.09 ± 0.09 | 0.20 ± 0.18 | 0.15 ± 0.16 | 0.12 ± 0.13 | 0.14 ± 0.15 |
| 22:4 (n-6) | 1.11 ± 1.40 | 2.56 ± 1.44 | 1.79 ± 1.55 | 0.55 ± 1.10 | 2.76 ± 0.53 |
| 22:5 (n-6) | 0.06 ± 0.04 | 0.15 ± 0.09 | 0.24 ± 0.20 | 0.17 ± 0.19 | 0.06 ± 0.03 |
| 22:5 (n-3) | 0.51 ± 0.23 | 0.56 ± 0.32 | 0.56 ± 0.22 | 0.45 ± 0.32 | 0.44 ± 0.15 |
| 22:6 (n-3) | 17.76 ± 1.00 | 23.62 ± 0.26 | 31.18 ± 1.89** | 19.52 ± 0.18 | 19.89 ± 0.91 |
| 24:1 (n-9) | 0.04 ± 0.03 | 0.11 ± 0.13 | 0.09 ± 0.06 | 0.04 ± 0.01 | 0.03 ± 0.03 |
| 16:0 DMA | 0.05 ± 0.02 | 0.05 ± 0.03 | 0.06 ± 0.04 | 0.13 ± 0.17 | 0.03 ± 0.02 |
| 18:0 DMA | 2.96 ± 0.467 | 2.642 ± 0.95 | 2.126 ± 0.56 | 1.97 ± 0.67 | 2.48 ± 0.47 |
| 18:1 DMA | 0.02 ± 0.02 | 0.05 ± 0.05 | 0.04 ± 0.04 | 0.02 ± 0.02 | 0.03 ± 0.03 |

*p < 0.05 compared to control,
**p < 0.005 compared to control, unpaired t-test adjusted with Holm-Sidak method.
KO: krill oil;
FO: fish oil;
FA: fatty acid;
S.D.: standard deviation.

REFERENCES

1. Cunnane, S. C., Chouinard-Watkins, R., Castellano, C. A., and Barberger-Gateau, P. (2013) Docosahexaenoic acid homeostasis, brain aging and Alzheimer's disease: Can we reconcile the evidence? *Prostaglandins Leukotrienes & Essential Fatty Acids* 88, 61-70.
2. Sethom, M. M., Fares, S., Bouaziz, N., Melki, W., Jemaa, R., Feki, M., Hechmi, Z., and Kaabachi, N. (2010) Polyunsaturated fatty acids deficits are associated with psychotic state and negative symptoms in patients with schizophrenia. *Prostaglandins Leukotrienes & Essential Fatty Acids* 83, 131-136.
3. Bazan, N. G., Molina, M. F., and Gordon, W. C. (2011) Docosahexaenoic acid signalolipidomics in nutrition: significance in aging, neuroinflammation, macular degeneration, Alzheimer's, and other neurodegenerative diseases. *Annu. Rev. Nutr* 31, 321-351.
4. Hong, S. H., Belayev, L., Khoutorova, L., Obenaus, A., and Bazan, N. G. (2014) Docosahexaenoic acid confers enduring neuroprotection in experimental stroke. *J Neurol. Sci* 338, 135-141.
5. Barrett, E. C., McBurney, M. I., and Ciappio, E. D. (2014) Omega-3 Fatty Acid Supplementation as a Potential Therapeutic Aid for the Recovery from Mild Traumatic Brain Injury/Concussion. *Advances in Nutrition: An International Review Journal* 5, 268-277.
6. Arsenault, D., Julien, C., Tremblay, C., and Calon, F. (2011) DHA Improves Cognition and Prevents Dysfunction of Entorhinal Cortex Neurons in 3xTg-AD Mice. *PLoS ONE* 6, e17397.
7. Perez, S. E., Berg, B. M., Moore, K. A., He, B., Counts, S. E., Fritz, J. J., Hu, Y. S., Lazarov, O., Lah, J. J., and Mufson, E. J. (2010) DHA diet reduces AD pathology in young APPswe/PS1delta E9 transgenic mice: Possible Gender Effects. *J Neurosci Res* 88, 1026-1040.
8. Lim, S. Y., and Suzuki, H. (2001) Changes in Maze Behavior of Mice Occur after Sufficient Accumulation of Docosahexaenoic Acid in Brain. *Journal of Nutrition* 131, 319-324.
9. Petursdottir, A. L., Farr, S. A., Morley, J. E., Banks, W. A., and Skuladottir, G. V. (2008) Effect of Dietary n-3 Polyunsaturated Fatty Acids on Brain Lipid Fatty Acid Composition, Learning Ability, and Memory of Senescence-Accelerated Mouse. *Journals of Gerontology. Series A, Biological Sciences and Medical Sciences* 63, 1153-1160.
10. Quinn, J. F., Raman, R., and Thomas, R. G. (2010) Docosahexaenoic acid supplementation and cognitive decline in alzheimer disease: A randomized trial. *JAMA* 304, 1903-1911.
11. Chiu, C. C., Su, K. P., Cheng, T. C., Liu, H. C., Chang, C. J., Dewey, M. E., Stewart, R., and Huang, S. Y. (2008) The effects of omega-3 fatty acids monotherapy in Alzheimer's disease and mild cognitive impairment: A preliminary randomized double-blind placebo-controlled study. *Progress in Neuro-Psychopharmacology and Biological Psychiatry* 32, 1538-1544.
12. Phillips, M. A., Childs, C. E., Calder, P. C., and Rogers, P. J. (2015) No Effect of Omega-3 Fatty Acid Supplementation on Cognition and Mood in Individuals with Cognitive Impairment and Probable Alzheimer's Disease: A Randomised Controlled Trial. *International Journal of Molecular Sciences* 16, 24600-24613.
13. Ferreira, J. J., Rosser, A., Craufurd, D., Squitieri, F., Mallard, N., and Landwehrmeyer, B. (2015) Ethyl-eicosapentaenoic acid treatment in Huntington's disease: A placebo-controlled clinical trial. *Movement Disorders* 30, 1426-1429.
14. Chen, A. T., Chibnall, J. T., and Nasrallah, H. A. (2015) A meta-analysis of placebo-controlled trials of omega-3 fatty acid augmentation in schizophrenia: Possible stage-specific effects. *Ann Clin Psychiatry* 27, 289-296.
15. Nguyen, L. N., Ma, D., Shui, G., Wong, P., Cazenave-Gassiot, A., Zhang, X., Wenk, M. R., Goh, E. L. K., and Silver, D. L. (2014) Mfsd2a is a transporter for the essential omega-3 fatty acid docosahexaenoic acid. *Nature* 509, 503-506.
16. Sugasini, D., Thomas, R., Yalagala, P. C. R., Tai, L. M., and Subbaiah, P. V. (2017) Dietary docosahexaenoic acid (DHA) as lysophosphatidylcholine, but not as free acid, enriches brain DHA and improves memory in adult mice. *Scientific Reports* 7, 11263.
17. Sugasini, D., Yalagala, P. C. R., Goggin, A., Tai, L. M., and Subbaiah, P. V. (2019) Enrichment of brain docosahexaenoic acid (DHA) is highly dependent upon the molecular carrier of dietary DHA: Lysophosphatidylcholine is more efficient than either phosphatidylcholine or triacylglycerol. *The Journal of Nutritional Biochemistry*, 108231.
18. Rodrigues, P. O., Martins, S. V., Lopes, P. A., Miguueis, S., Alfaia, C. M., Pinto, R. M. A., Rolo, E. A., Bispo, P., Batista, I., Bandarra, N. M., and Prates, J. A. M. (2014) Influence of feeding graded levels of canned sardines on the inflammatory markers and tissue fatty acid composition of Wistar rats. *British Journal of Nutrition* 112, 309-319.
19. Kaur, G., Begg, D. P., Barr, D., Garg, M., Cameron-Smith, D., and Sinclair, A. J. (2010) Short-term docosapentaenoic acid (22:5 n-3) supplementation increases tissue docosapentaenoic acid, DHA and EPA concentrations in rats. *Br J Nutr* 103, 32-37.
20. Tou, J., Altman, S., Gigliotti, J., Benedito, V., and Cordonier, E. (2011) Different sources of omega-3 polyunsaturated fatty acids affects apparent digestibility, tissue deposition, and tissue oxidative stability in growing female rats. *Lipids in Health and Disease* 10, 179.
21. Cruz-Hernandez, C., Thakkar, S. K., Moulin, J., Oliveira, M., Masserey-Elmelegy, I., Dionisi, F., and Destaillats, F. (2012) Benefits of structured and free monoacylglycerols to deliver eicosapentaeroic (EPA) in a model of lipid malabsorption. *Nutrients* 4, 1781-1793.
22. Martins, J. G. (2009) EPA but not DHA appears to be responsible for the efficacy of omega-3 long chain polyunsaturated fatty acid supplementation in depression: evidence from a meta-analysis of randomized controlled trials. *J Am Coll. Nutr* 28, 525-542.
23. Song, C., Shieh, C. H., Wu, Y. S., Kalueff, A., Gaikwad, S., and Su, K. P. (2016) The role of omega-3 polyunsaturated fatty acids eicosapentaenoic and docosahexaenoic acids in the treatment of major depression and Alzheimer's disease: Acting separately or synergistically? *Prog Lipid Res* 62, 41-54.
24. Ross, B. M. (2008) The Emerging Role of Eicosapentaenoic Acid as an Important Psychoactive Natural Product: Some Answers but a Lot more Questions. *Lipid Insights* 2, 89-97.
25. Chen, C. T., and Bazinet, R. P. (2015) b-oxidation and rapid metabolism, but not uptake regulate brain eicosapentaenoic acid levels. *Prostaglandins Leukotrienes & Essential Fatty Acids* 92, 33-40.
26. Yalagala, P. C., Sugasini, D., Dasarathi, S., Pahan, K., and Subbaiah, P. V. (2019) Dietary lysophosphatidylcholine-EPA enriches both EPA and DHA in the brain: Potential treatment for depression. *Journal of Lipid Research.*
27. Ivanova, P. T., Milne, S. B., Byrne, M. O., Xiang, Y., and Brown, H. A. (2007) Glycerophospholipid identification and quantitation by electrospray ionization mass spectrometry. *Methods Enzymol* 432, 21-57.
28. Sugasini, D., and Subbaiah, P. V. (2017) Rate of acyl migration in lysophosphatidylcholine (LPC) is dependent upon the nature of the acyl group. Greater stability of sn-2 docosahexaenoyl LPC compared to the more saturated LPC species. *PLoS ONE* 12, e0187826.
29. Yalagala, P. C. R., Sugasini, D., Dasarathi, S., Pahan, K., and Subbaiah, P. V. (2019) Dietary lysophosphatidylcholine-EPA enriches both EPA and DHA in the brain: potential treatment for depression. *Journal of Lipid Research* 60, 566-578.
30. Bligh, E. G., and Dyer, W. J. (1959) A rapid method of total lipid extraction and purification. *Can. J. Biochem. Physiol* 37, 911-917.
31. Subbaiah, P. V., Dammanahalli, K. J., Yang, P., Bi, J., and O'Donnell, J. M. (2016) Enhanced incorporation of dietary DHA into lymph phospholipids by altering its molecular carrier. *Biochim Biophys Acta* 1861, 723-729.
32. Croset, M., Brossard, N., Polette, A., and Lagarde, M. (2000) Characterization of plasma unsaturated lysophosphatidylcholines in human and rat. *Biochemical Journal* 345, 61-67.
33. Brindley, D. N. (1993) Hepatic secretion of lysophosphatidylcholine: A novel transport system for polyunsaturated fatty acids and choline. *J. Nutr. Biochem* 4, 442-449.
34. Sekas, G., Patton, G. M., Lincoln, E. C., and Robins, S. J. (1985) Origin of plasma lysophosphatidylcholine: evidence for direct hepatic secretion in the rat. *J Lab Clin Med* 105, 190-194.
35. Ramprasath, V. R., Eyal, I., Zchut, S., and Jones, P. J. H. (2013) Enhanced increase of omega-3 index in healthy individuals with response to 4-week n-3 fatty acid supplementation from krill oil versus fish oil. *Lipids in Health and Disease* 12, 178.
36. Schuchardt, J. P., Schneider, I., Meyer, H., Neubronner, J., von Schacky, C., and Hahn, A. (2011) Incorporation of EPA and DHA into plasma phospholipids in response to different omega-3 fatty acid formulations—a comparative bioavailability study of fish oil vs. krill oil. *Lipids Health Dis* 10, 145-145.
37. Salem, N., and Kuratko, C. N. (2014) A reexamination of krill oil bioavailability studies. *Lipids in Health and Disease* 13, 137.
38. Sona, C., Kumar, A., Dogra, S., Kumar, B. A., Umrao, D., and Yadav, P. N. (2018) Docosahexaenoic acid modulates brain-derived neurotrophic factor via GPR40 in the brain and alleviates diabesity-associated learning and memory deficits in mice. *Neurobiol Dis* 118, 94-107.
39. Sun, G. Y., Simonyi, A., Fritsche, K. L., Chuang, D. Y., Hannink, M., Gu, Z., Greenlief, C. M., Yao, J. K., Lee, J. C., and Beversdorf, D. Q. (2018) Docosahexaenoic acid (DHA): An essential nutrient and a nutraceutical for brain health and diseases. *Prostaglandins Leukotrienes & Essential Fatty Acids* 136, 3-13.
40. Lima Giacobbo, B., Doorduin, J., Klein, H. C., Dierckx, R. A. J. O., Bromberg, E., and de Vries, E. F. J. (2019) Brain-Derived Neurotrophic Factor in Brain Disorders: Focus on Neuroinflammation. *Molecular Neurobiology* 56, 3295-3312.
41. Bazan, N. G. (2018) Docosanoids and elovanoids from omega-3 fatty acids are pro-homeostatic modulators of inflammatory responses, cell damage and neuroprotection. *Molecular Aspects of Medicine* 64, 18-33.
42. Querques, G. F., R. and Souied, E. H. (2011) Retina and Omega-3. *Journal of Nutrition and Metabolism* 2011.
43. Souied, E. H., Aslam, T., Garcia-Layana, A., Holz, F. G., Leys, A., Silva, R., and Delcourt, C. (2016) Omega-3 Fatty Acids and Age-Related Macular Degeneration. *Ophthalmic Research* 55, 62-69.
44. Tikhonenko, M., Lydic, T. A., Opreanu, M., Li Calzi, S., Bozack, S., McSorley, K. M., Sochacki, A. L., Faber, M. S., Hazra, S., Duclos, S., Guberski, D., Reid, G. E., Grant, M. B., and Busik, J. V. (2013) N-3 Polyunsaturated Fatty Acids Prevent Diabetic Retinopathy by Inhibition of Retinal Vascular Damage and Enhanced Endothelial Progenitor Cell Reparative Function. *PLOS ONE* 8, e55177.
45. Harauma, A., Saito, J., Watanabe, Y., and Moriguchi, T. (2014) Potential for daily supplementation of n-3 fatty acids to reverse symptoms of dry eye in mice. *Prostaglandins, Leukotrienes and Essential Fatty Acids* 90, 207-213.
46. Qiu, S., Wei, Y., Zhou, X., Jiang, Z., Zhang, T., Jiang, X., and Zhang, S. (2017) Intravitreal injection of docosahexaenoic acid attenuated photoreceptor cell injury in a NaIO3-induced age-related macular degeneration rat model. *Neuroscience Letters* 657, 53-61.
47. Chew, E. Y., Clemons, T. E., Agrón, E., Launer, L. J., Grodstein, F., Bernstein, P. S., and Group, f t. A.-R. E. D. S. R. (2015) Effect of Omega-3 Fatty Acids, Lutein/Zeaxanthin, or Other Nutrient Supplementation on Cognitive Function: The AREDS2 Randomized Clinical Trial. *JAMA* 314, 791-801.
48. Lee, T. K. M., Clandinin, M. T., Hébert, M., and MacDonald, I. M. (2010) Effect of docosahexaenoic acid supplementation on the macular function of patients with Best vitelliform macular dystrophy: randomized clinical trial. *Canadian Journal of Ophthalmology* 45, 514-519.
49. Nishizawa, Wang, Sekine, and Saito. (2003) Effect of Dietary DHA on DHA Levels in Retinal Rod Outer Segments in Young versus Mature Rats. *International Journal for Vitamin and Nutrition Research* 73, 259-265.
50. Jump, D. B., Depner, C. M., Tripathy, S., and Lytle, K. A. (2015) Potential for Dietary ω-3 Fatty Acids to Prevent Nonalcoholic Fatty Liver Disease and Reduce the Risk of Primary Liver Cancer. *Advances in Nutrition* 6, 694-702.
51. Kelley, N. S. (2016) Treatment of Nonalcoholic Fatty Liver Disease with Long-Chain n-3 Polyunsaturated Fatty Acids in Humans. *Metab Syndr Relat Disord* 14, 417-430.
52. Stinson A. M., Wiegand R. D., Anderson R. E. Recycling of docosahexaenoic acid in rat retinas during n-3 fatty acid deficiency. *J. Lipid Res.* 1991; 32:2009-2017.
53. Jasani B., Simmer K., Patole S. K., Rao S. C. Long chain polyunsaturated fatty acid supplementation in infants born at term. *Cochr. Database Syst. Rev.* 2017; 3:CD000376. doi: 10.1002/14651858.CD000376.pub4.
54. SanGiovanni J. P., Chew E. Y. The role of omega-3 long-chain polyunsaturated fatty acids in health and disease of the retina. *Progress Retin. Eye Res.* 2005; 24:87-138. doi: 10.1016/j.preteyeres.2004.06.002.
55. Souied E. H., Aslam T., Garcia-Layana A., Holz F. G., Leys A., Silva R., Delcourt C. Omega-3 fatty acids and age-related macular degeneration. *Ophthalmic Res.* 2016; 55:62-69. doi: 10.1159/000441359.
56. Sapieha P., Chen J., Stahl A., Seaward M. R., Favazza T. L., Juan A. M., Hatton C. J., Joyal J. S., Krah N. M., Dennison R. J., et al. Omega-3 polyunsaturated fatty acids preserve retinal function in type 2 diabetic mice. *Nutr. Diabet.* 2012; 2:e36. doi: 10.1038/nutd.2012.10.

57. Yee P., Weymouth A. E., Fletcher E. L., Vingrys A. J. A Role for Omega-3 Polyunsaturated Fatty Acid Supplements in Diabetic Neuropathy. Investig. *Ophthalmol. Vis. Sci.* 2010; 51:1755-1764. doi: 10.1167/iovs.09-3792.

58. Hegde K. R., Varma S. D. Electron impact mass spectroscopic studies on mouse retinal fatty acids: Effect of diabetes. *Ophthalmic Res.* 2009; 42:9-14. doi: 10.1159/000219679.

59. Futterman S., Sturtevant R., Kupfer C. Effect of alloxan diabetes on the fatty acid composition of the retina. *Investig. Ophtalmol. Vis. Sci.* 1969; 8:542-544.

60. Anderson R. E., Maude M. B., Bok D. Low docosahexaenoic acid levels in rod outer segment membranes of mice with rds/peripherin and P216L peripherin mutations. *Investig. Ophthalmol. Vis. Sci.* 2001; 42:1715-1720.

61. Gong J., Rosner B., Rees D. G., Berson E. L., Weigel-DiFranco C. A., Schaefer E. J. Plasma docosahexaenoic acid levels in various genetic forms of retinitis pigmentosa. Investig. *Ophthalmol. Vis. Sci.* 1992; 33:2596-2602.

62. Martinez M. Severe deficiency of docosahexaenoic acid in peroxisomal disorders: A defect of delta 4 desaturation? *Neurology.* 1990; 40:1292-1298. doi: 10.1212/WNL.40.8.1292.

63. Uauy R., Hoffman D. R., Peirano P., Birch D. G., Birch E. E. Essential fatty acids in visual and brain development. *Lipids.* 2001; 36:885-895. doi: 10.1007/s11745-001-0798-1.

64. Hoffman D. R., Hughbanks-Wheaton D. K., Pearson N. S., Fish G. E., Spencer R., Takacs A., Klein M., Locke K. G., Birch D. G. Four-year placebo-controlled trial of docosahexaenoic acid in X-linked retinitis pigmentosa (DHAX trial): A randomized clinical trial. *JAMA Ophthalmol.* 2014; 132:866-873. doi: 10.1001/jamaophthalmol.2014.1634.

65. Tachikawa M., Akanuma S. I., Imai T., Okayasu S., Tomohiro T., Hatanaka Y., Hosoya K. I. Multiple cellular transport and binding processes of unesterified docosahexaenoic acid in outer blood-retinal barrier retinal pigment epithelial cells. *Biol. Pharm. Bull.* 2018; 41:1384-1392. doi: 10.1248/bpb.b18-00185.

66. Wong B. H., Chan J. P., Cazenave-Gassiot A., Poh R. W., Foo J. C., Galam D. L., Ghosh S., Nguyen L. N., Barathi V. A., Yeo S. W., et al. Mfsd2a is a transporter for the essential omega-3 fatty acid docosahexaenoic acid (DHA) in eye and is important for photoreceptor cell development. *J Biol. Chem.* 2016; 291:10501-10514. doi: 10.1074/jbc.M116.721340.

67. Yalagala P. C. R., Sugasini D., Zaldua S. B., Tai L. M., Subbaiah P. V. Lipase treatment of dietary krill oil, but not fish oil, enables enrichment of brain eicosapentaenoic acid (EPA) and docosahexaenoic acid (DHA)*Mol. Nutr. Food Res.* 2020; 64 doi: 10.1002/mnfr.202000059.

68. Hachem M., Geloen A., Van A., Foumaux B., Fenart L Gosselet F., Da Silva P., Breton G., Lagarde M., Picq M., et al. Efficient docosahexaenoic acid uptake by the brain from a structured phospholipid. *Mol. Neurobiol.* 2015 doi: 10.1007/s12035-015-9228-9.

69. Thies F., Delachambre M. C., Bentejac M., Lagarde M., Lecerf J. Lyso-sn 1 Phosphatidylcholine Bound to Albumin: A Preferential Form for Rat Brain Uptake of Unsaturated Fatty Acids Compared to the Unesterified Form?; Proceedings of the 32nd International Conference on Biochemistry of Lipids; Granada, Spain. 18-21 Sep. 1991; p. 3.

70. Abcouwer S. F., Gardner T. W. Diabetic retinopathy: Loss of neuroretinal adaptation to the diabetic metabolic environment. *Ann. N. Y. Acad. Sci.* 2014; 1311:174-190. doi: 10.1111/nyas.12412.

71. Rossino M. G., Casini G. Nutraceuticals for the treatment of diabetic retinopathy. *Nutrients.* 2019; 11:771. doi: 10.3390/nu11040771.

72. Hashimoto M., Hossain S., Al Mamun A., Matsuzaki K., Arai H. Docosahexaenoic acid: One molecule diverse functions. *Crit. Rev. Biotechnol.* 2017; 37:579-597. doi: 10.1080/07388551.2016.1207153.

73. Green P., Glozman S., Weiner L., Yavin E. Enhanced free radical scavenging and decreased lipid peroxidation in the rat fetal brain after treatment with ethyl docosahexaenoate. *Biochim. Biophys. Acta Mol. Cell Biol. Lipids.* 2001; 1532:203-212. doi: 10.1016/S1388-1981(01)00132-9.

74. Schaefer E. J., Robins S. J., Patton G. M., Sandberg M. A., Weigel-DiFranco C. A., Rosner B., Berson E. L. Red blood cell membrane phosphatidylethanolamine fatty acid content in various forms of retinitis pigmentosa. *J. Lipid Res.* 1995; 36:1427-1433.

75. Kalogerou M., Kolovos P., Prokopiou E., Papagregoriou G., Deltas C., Malas S., Georgiou T. Omega-3 fatty acids protect retinal neurons in the DBA/2J hereditary glaucoma mouse model. *Exp. Eye Res.* 2018; 167:128-139. doi: 10.1016/j.exer.2017.12.005.

76. Yang S. P., Morita I., Murota S. I. Eicosapentaenoic acid attenuates vascular endothelial growth factor-induced proliferation via inhibiting Flk-1 receptor expression in bovine carotid artery endothelial cells. *J. Cell Physiol.* 1998; 176:342-349. doi: 10.1002/(SICI)1097-4652(199808)176:2<342::AID-JCP12>3.0.CO; 2-5.

77. McCusker M. M., Durrani K., Payette M. J., Suchecki J. An eye on nutrition: The role of vitamins, essential fatty acids, and antioxidants in age-related macular degeneration, dry eye syndrome, and cataract. *Clin. Dermatol.* 2016; 34:276-285. doi: 10.1016/j.clindermatol.2015.11.009.

78. Prokopiou E., Kolovos P., Georgiou C., Kalogerou M., Potamiti L., Sokratous K., Kyriacou K., Georgiou T. Omega-3 fatty acids supplementation protects the retina from age-associated degeneration in aged C57BL/6J mice. *BMJ Open Ophthalmol.* 2019; 4:e000326. doi: 10.1136/bmjophth-2019-000326.

79. Prokopiou E., Kolovos P., Kalogerou M., Neokleous A., Nicolaou O., Sokratous K., Kyriacou K., Georgiou T. Omega-3 fatty acids supplementation: Therapeutic potential in a mouse model of stargardt disease. *Investig. Ophtalmol. Vis. Sci.* 2018; 59:2757-2767. doi: 10.1167/iovs.17-23523.

80. Schnebelen C., Viau S., Grégoire S., Joffre C., Creuzot-Garcher C. P., Bron A. M., Bretillon L., Acar N. Nutrition for the eye: Different susceptibility of the retina and the lacrimal gland to dietary omega-6 and omega-3 polyunsaturated fatty acid incorporation. *Ophthalmic Res.* 2009; 41:216-224. doi: 10.1159/000217726.

81. Tanito M., Brush R. S., Elliott M. H., Wicker L. D., Henry K. R., Anderson R. E. High levels of retinal membrane docosahexaenoic acid increase susceptibility to stress-induced degeneration. *J. Lipid Res.* 2009; 50:807-819. doi: 10.1194/jlr.M800170-JLR200.

82. Suh M., Sauvé Y., Merrells K. J., Kang J. X., Ma D. W. L. Supranormal electroretinogram in F at-1 mice with retinas enriched in docosahexaenoic acid and n-3 very long chain fatty acids (C24-C36) *Investig. Ophthalmol. Vis. Sci.* 2009; 50:4394-4401. doi: 10.1167/iovs.08-2565.

83. Connor K. M., SanGiovanni J. P., Lofqvist C., Aderman C. M., Chen J., Higuchi A., Hong S., Pravda E. A., Majchrzak S., Carper D., et al. Increased dietary intake of -ë-3-polyunsaturated fatty acids reduces pathological retinal angiogenesis. *Nat. Med.* 2007; 13:868. doi: 10.1038/nm1591.
84. Nair A. B., Jacob S. A simple practice guide for dose conversion between animals and human. *J. Basic Clin. Pharm.* 2016; 7:27-31. doi: 10.4103/0976-0105.177703.
85. Lobanova E. S., Schuhmann K., Finkelstein S., Lewis T. R., Cady M. A., Hao Y., Keuthan C., Ash J. D., Burns M. E., Shevchenko A., et al. Disrupted blood-retina lysophosphatidylcholine transport impairs photoreceptor health but not visual signal transduction. *Neurosci.* 2019; 39:9689-9701. doi: 10.1523/JNEUROSCI.1142-19.2019.
86. Kaur G., Molero J. C., Weisinger H. S., Sinclair A. J. Orally administered [14C] DPA and [14C] DHA are metabolised differently to [14C] EPA in rats. *Br. J. Nutr.* 2013; 109:441-448. doi: 10.1017/S0007114512001419.
87. Suh M., Clandinin M. T. 20:5n-3 but not 22:6n-3 is a preferred substrate for synthesis of n-3 very-long-chain fatty acids (C24-C36) in retina. *Curr. Eye Res.* 2005; 30:959-968. doi: 10.1080/02713680500246957.
88. Yu M., Benham A., Logan S., Brush R. S., Mandal M. N., Anderson R. E., Agbaga M. P. ELOVL4 protein preferentially elongates 20:5n3 to very long chain PUFAs over 20:4n6 and 22:6n3. *J. Lipid Res.* 2012; 53:494-504. doi: 10.1194/jlr.M021386.
89. Jun B., Mukherjee P. K., Asatryan A., Kautzmann M. A., Heap J., Gordon W. C., Bhattacharjee S., Yang R., Petasis N. A., Bazan N. G. Elovanoids are novel cell-specific lipid mediators necessary for neuroprotective signaling for photoreceptor cell integrity. *Sci. Rep.* 2017; 7:5279. doi: 10.1038/s41598-017-05433-7.
90. Faiq M. A., Wollstein G., Schuman J. S., Chan K. C. Cholinergic nervous system and glaucoma: From basic science to clinical applications. *Prog. Retin. Eye Res.* 2019; 72:100767. doi: 10.1016/j.preteyeres.2019.06.003.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A method for improving, controlling, reducing, or alleviating one or more symptoms and/or signs of an eye disease or condition in a subject in need thereof comprising:
administering to the subject in need thereof an effective amount of a pharmaceutical or nutraceutical formulation comprising a lysophosphatidylcholine (LPC) composition comprising a LPC-compound selected from the group consisting of any one of formulas 1 to 8, and any combination thereof, so that the symptoms of the disease or condition are improved, controlled, reduced, or alleviated:

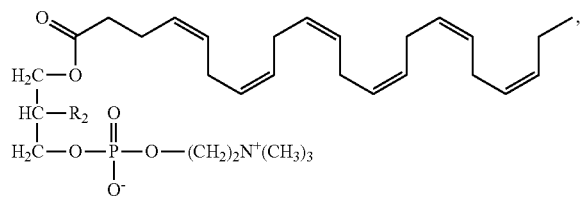

(1)

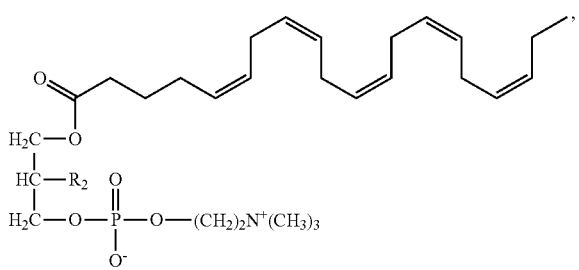

(2)

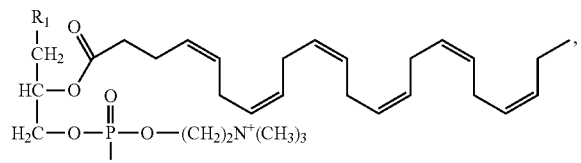

(3)

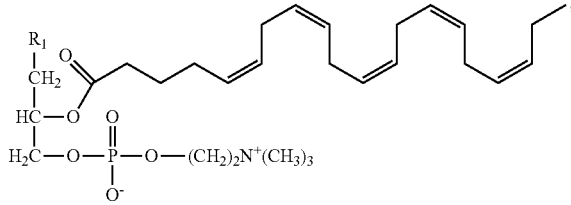

(4)

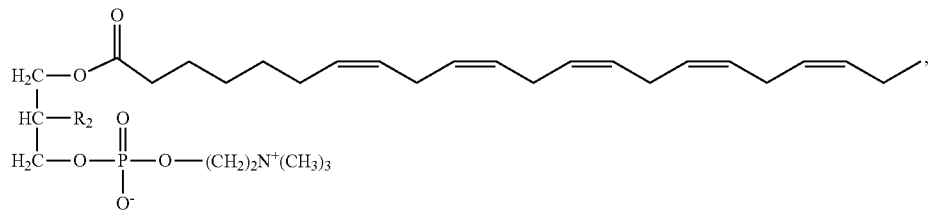

(5)

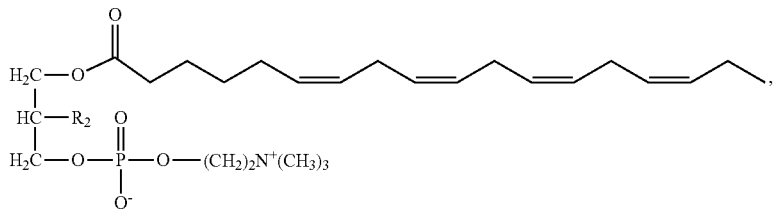

(6)

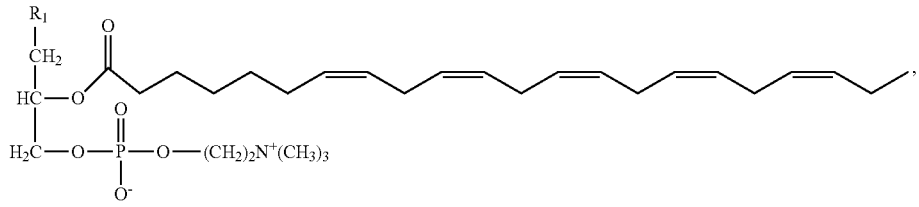

(7)

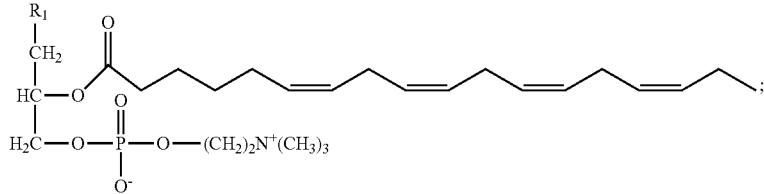

(8)

wherein:
R₁ is OH or —OC(O)(CH₂)$_n$CH₃;
R₂ is OH or —OC(O)(CH₂)$_n$CH₃; and
n is 0, 1, or 2;
and wherein the molar ratio of lysoPC-EPA:lysoPC-DHA is in the range of from 1:1 to 5:1; and further wherein
  i) the number of moles of lysoPC-EPA is the number of moles 1-lysoPC-EPA plus the number of moles 2-lysoPC-EPA; and
  ii) ii) the number of moles of lysoPC-DHA is the number of moles 1-lysoPC-DHA plus the number of moles 2-lysoPC-DHA.

2. The method of claim 1, wherein R₁ is OH and R₂ is OH.

3. The method according to claim 1, with the proviso that: if the LPC composition comprises i) a compound according to formula 1, wherein R₂ is OH; and/or ii) a compound according to formula 3, wherein R₁ is OH; then the LPC composition further comprises at least one of the other LPC-compounds referred to in claim 1.

4. The method of claim 1, wherein the one or more LPC-compound is:
  a compound according to formula 1; and/or a compound according to formula 3; and
  a compound according to formula 2; and/or a compound according to formula 4.

5. The method of claim 1, wherein
  R₁ and R₂ are OH; and
  the molar ratio of lysoPC-DHA:lysoPC-EPA is from 1:1 to 3:1 wherein i) the number of moles of lysoPC-EPA is the number of moles 1-lysoPC-EPA+the number of moles 2-lysoPC-EPA; and ii) the number of moles of lysoPC-DHA is the number of moles 1-lysoPC-DHA+the number of moles 2-lysoPC-DHA.

6. The method of claim 1, wherein the disease or condition is dry eye.

7. The method of claim 1, wherein the disease or condition is a neurodegenerative disease of the eye.

8. The method of claim 7, wherein the neurodegenerative disease of the eye is selected from the group consisting of age-related macular degeneration, diabetic retinopathy, non-proliferative retinopathy, proliferative retinopathy, diabetic macular edema, retinitis pigmentosa, central vein occlusion, and glaucoma.

9. The method of claim 1, wherein the administering is by a mode selected from the group consisting of oral administration and intravascular administration.

10. The method of claim 9, wherein the mode of administration is oral administration.

11. The method of claim 9, wherein the mode of administration is intravascular administration.

12. The method of claim 1, wherein the LPC composition in the formulation comprises an amount of total LPC from 10% to 100% by weight of the LPC composition.

13. The method of claim 1, wherein the LPC composition comprises an additional lipid different from LPC.

14. The method of claim 13, wherein the additional lipid is selected from the group consisting of triglycerides, free fatty acids, ethyl esters and phospholipids selected from the group consisting of phosphatidylethanolamine and phosphatidylcholine.

15. The method of claim 14, wherein the LPC composition comprises a predominant amount of the LPC-compound compared to an amount of phosphatidylcholine.

16. The method of claim 1, wherein the formulation further comprises a component selected from the group consisting of lutein, astaxanthin, zeaxanthin and any combinations thereof.

17. The method of claim 1, wherein the subject is a mammalian subject.

18. The method of claim 17, wherein the subject is a human subject.

19. The method of claim 6, wherein
  R₁ and R₂ are OH; and
  the molar ratio of lysoPC-EPA:lysoPC-DHA is from 1:1 to 5:1; wherein i) the number of moles of lysoPC-EPA is the number of moles 1-lysoPC-EPA+the number of moles 2-lysoPC-EPA; and ii) the number of moles of lysoPC-DHA is the number of moles 1-lysoPC-DHA+ the number of moles 2-lysoPC-DHA.

\* \* \* \* \*

UNITED STATES PATENT AND TRADEMARK OFFICE
CERTIFICATE OF CORRECTION

PATENT NO. : 11,744,864 B2
APPLICATION NO. : 17/218760
DATED : September 5, 2023
INVENTOR(S) : Myhren et al.

Page 1 of 1

It is certified that error appears in the above-identified patent and that said Letters Patent is hereby corrected as shown below:

On the Title Page

Item (73) Assignee, change "THE UNITED STATES OF AMERICA REPRESENTED BY THE DEPARTMENT OF VETERANS AFFAIRS, Washington, DC (US)" to --AKER BIOMARINE ANTARCTIC AS, Stamsund, (NO); THE BOARD OF TRUSTEES OF THE UNIVERSITY OF ILLINOIS, Urbana, IL (US); THE UNITED STATES OF AMERICA REPRESENTED BY THE DEPARTMENT OF VETERANS AFFAIRS, Washington, DC (US)--.

Signed and Sealed this
Sixteenth Day of April, 2024

Katherine Kelly Vidal
*Director of the United States Patent and Trademark Office*